(12) United States Patent
Fujita et al.

(10) Patent No.: US 10,367,148 B2
(45) Date of Patent: Jul. 30, 2019

(54) LIGHT-EMITTING DEVICE, ELECTRONIC APPARATUS, AND INSPECTION METHOD

(71) Applicant: Seiko Epson Corporation, Tokyo (JP)

(72) Inventors: Tetsuji Fujita, Chino (JP); Yuiga Hamade, Fujimi-machi (JP)

(73) Assignee: Seiko Epson Corporation (JP)

( * ) Notice: Subject to any disclaimer, the term of this patent is extended or adjusted under 35 U.S.C. 154(b) by 222 days.

(21) Appl. No.: 15/315,569

(22) PCT Filed: May 26, 2015

(86) PCT No.: PCT/JP2015/002640
§ 371 (c)(1),
(2) Date: Dec. 1, 2016

(87) PCT Pub. No.: WO2015/186311
PCT Pub. Date: Dec. 10, 2015

(65) Prior Publication Data
US 2017/0200901 A1      Jul. 13, 2017

(30) Foreign Application Priority Data

Jun. 2, 2014   (JP) ................................ 2014-114339

(51) Int. Cl.
*G01R 31/00* (2006.01)
*H01L 51/00* (2006.01)
(Continued)

(52) U.S. Cl.
CPC ........ *H01L 51/0061* (2013.01); *C07D 513/04* (2013.01); *C07F 5/022* (2013.01);
(Continued)

(58) Field of Classification Search
CPC .... G01R 31/2635; G01R 31/44; G01R 31/24; H05B 37/03
(Continued)

(56) References Cited

U.S. PATENT DOCUMENTS 6,680,131 B1    1/2004  Ishibashi et al.
2004/0183082 A1*  9/2004  Yamazaki ........... H01L 51/5036
                                                              257/79
(Continued)

FOREIGN PATENT DOCUMENTS

CN    102956841 A    3/2013
JP    2000-091073 A  3/2000
(Continued)

OTHER PUBLICATIONS

Qian, Gang et al.: "Band Gap Tunable, Donor-Acceptor-Donor Charge-Transfer Heteroquinoid-Based Chromophores: Near Infrared Photoluminescence and Electroluminescence", Chem. Mater.; vol. 20; No. 19; 2008, pp. 6208-6216 (9 pages).

(Continued)

*Primary Examiner* — Huy Q Phan
*Assistant Examiner* — Raul J Rios Russo
(74) *Attorney, Agent, or Firm* — Harness, Dickey, & Pierce, P.L.C.

(57) ABSTRACT

To provide a light-emitting element which emits light in a near-infrared region and has high efficiency and long life, and a light-emitting device, an authentication device, and an electronic apparatus, each of which includes this light-emitting element.
A light-emitting device 100 of the invention includes a light-emitting element 1A including an anode 3, a cathode 8, and a light-emitting layer 5 which is provided between the anode 3 and the cathode 8 and emits light in a near-infrared region by applying a current between the anode 3 and the cathode 8, wherein the device emits visible light with a luminance of 5 cd/m$^2$ or more when a current is applied between the anode 3 and the cathode 8 at a current density of 300 A/cm$^2$ or less.

13 Claims, 17 Drawing Sheets

(51) Int. Cl.
*C07D 513/04* (2006.01)
*C09K 11/06* (2006.01)
*H01L 51/50* (2006.01)
*C07F 5/02* (2006.01)
*C09K 11/02* (2006.01)
*G01R 31/44* (2006.01)

(52) U.S. Cl.
CPC .......... *C09K 11/025* (2013.01); *C09K 11/06* (2013.01); *G01R 31/44* (2013.01); *H01L 51/008* (2013.01); *H01L 51/0058* (2013.01); *H01L 51/0072* (2013.01); *H01L 51/50* (2013.01); *C07F 5/02* (2013.01); *C09K 2211/1007* (2013.01); *C09K 2211/1014* (2013.01); *C09K 2211/1022* (2013.01); *C09K 2211/1081* (2013.01); *H01L 51/0071* (2013.01); *H01L 51/5012* (2013.01); *H01L 51/5072* (2013.01); *H01L 2251/533* (2013.01); *H01L 2251/558* (2013.01)

(58) Field of Classification Search
USPC .................................. 324/57, 378, 403, 414
See application file for complete search history.

(56) References Cited

U.S. PATENT DOCUMENTS

| | | |
|---|---|---|
| 2009/0159817 A1 | 6/2009 | Irie et al. |
| 2012/0262057 A1 | 10/2012 | Fujita et al. |
| 2012/0267615 A1 | 10/2012 | Fujita et al. |
| 2013/0037784 A1 | 2/2013 | Yamamoto et al. |
| 2013/0037785 A1 | 2/2013 | Fujita et al. |
| 2013/0221334 A1 | 8/2013 | Yamamoto et al. |
| 2013/0313532 A1* | 11/2013 | Watanabe ........... H01L 51/0071 257/40 |
| 2014/0110686 A1 | 4/2014 | Fujita et al. |
| 2014/0291647 A1* | 10/2014 | Suzuki ............... H01L 51/0085 257/40 |
| 2014/0306206 A1* | 10/2014 | Watanabe ............ C07D 307/91 257/40 |
| 2015/0295182 A1* | 10/2015 | Fujita ................. H01L 51/0061 257/40 |
| 2018/0151815 A1* | 5/2018 | Suzuki ............... H01L 51/0085 |

FOREIGN PATENT DOCUMENTS

| | | |
|---|---|---|
| JP | 2001-110570 A | 4/2001 |
| JP | 2006-310538 A | 11/2006 |
| JP | 2009158126 A | 7/2009 |
| JP | 2010176966 A | 8/2010 |
| JP | 2011029364 A | 2/2011 |
| JP | 2012219078 A | 11/2012 |
| JP | 2012224567 A | 11/2012 |
| JP | 2013035784 A | 2/2013 |
| JP | 2013-105665 A | 5/2013 |
| JP | 2013177327 A | 9/2013 |
| JP | 2014080400 A | 5/2014 |
| JP | 2014080401 A | 5/2014 |
| JP | 2014080402 A | 5/2014 |
| JP | 2014082406 A | 5/2014 |
| WO | WO-2007-072741 A1 | 6/2007 |

OTHER PUBLICATIONS

Extended European Search Report for Application No. EP 15 80 2371 dated Jan. 4, 2018 (8 pages).

* cited by examiner

LIGHT-EMITTING DEVICE, ELECTRONIC APPARATUS, AND INSPECTION METHOD

CROSS-REFERENCE TO RELATED APPLICATIONS

This application is a U.S. National Phase Application under 35 U.S.C. 371 of International Application No. PCT/JP2015/002640, filed on May 26, 2015 and published in Japanese as WO 2015/186311 on Dec. 10, 2015. This application claims priority to Japanese Patent Application No. 2014-114339, filed on Jun. 2, 2014. The entire disclosures of the above applications are incorporated herein by reference.

TECHNICAL FIELD

The present invention relates to a light-emitting device, an electronic apparatus, and an inspection method.

BACKGROUND ART

An organic electroluminescence element (so-called organic EL element) is a light-emitting element having a structure in which at least one layer of a luminous organic layer is interposed between an anode and a cathode. In such a light-emitting element, by applying an electrical field between the cathode and the anode, an electron is injected into a light-emitting layer from the cathode side and also a hole is injected into the light-emitting layer from the anode side, and the electron and the hole are recombined in the light-emitting layer, whereby an exciton is formed, and the energy generated when this exciton is returned to a ground state is emitted as light.

As such a light-emitting element, there is known a light-emitting element which emits light in a near-infrared region exceeding 700 nm (see, for example, JP-A-2000-091073 and JP-A-2001-110570), and recently, the realization of such a light-emitting element which surface-emits light in a near-infrared region as, for example, a light-emitting device such as a light source for biometric authentication for authenticating an individual using biological information such as a vein or a fingerprint, or a near-infrared display for military purposes or the like has been studied.

On the other hand, in a pre-shipment inspection after production of such a light-emitting device, it is necessary to remove a light-emitting device in which a defect such as a dark spot, nonluminescence, or a pixel defect caused by a foreign substance, an air bubble, or the like as a defective product.

In the case of a light-emitting device which emits visible light, in a pre-shipment inspection, by observing the defect by the naked eye while turning on the light-emitting device, it is possible to remove a defective product without using a given inspection apparatus. This means that the correctness of the results of inspection using the given inspection apparatus can be confirmed by the naked eye, and the confirmation of the operation of the given inspection apparatus can be performed by people.

However, in the case of a light-emitting device which emits light in a near-infrared region, the light in a near-infrared region cannot be recognized by the naked eye, and therefore, such a method could not be applied.

One of the objects of the invention is to provide a light-emitting device which can be easily found to be a defective product or not in a pre-shipment inspection, an electronic apparatus including such a light-emitting device, and an inspection method for inspecting whether such a light-emitting device is a defective product or not.

SUMMARY

In order to solve at least one of the above problems, the invention of this application can adopt the following configuration.

A light-emitting device of the invention is characterized by including a light-emitting element including an anode, a cathode, and a light-emitting layer which is provided between the anode and the cathode and emits light in a near-infrared region by applying a current between the anode and the cathode, and emitting visible light with a luminance of 5 cd/m$^2$ or more when a current is applied between the anode and the cathode at a current density of 300 mA/cm$^2$ or less.

In this manner, the light-emitting device emits visible light with a luminance of 5 cd/m$^2$ or more, and therefore, it can be easily found whether the light-emitting device is a defective product or not by observing this visible light in a pre-shipment inspection.

In the light-emitting device of the invention, it is preferred that the light-emitting layer is constituted by including a light-emitting material and a host material which holds the light-emitting material.

According to this, by appropriately combining the light-emitting material and the host material, the light-emitting layer can be made to emit light both in a near-infrared region and in a visible light region.

In the light-emitting device of the invention, it is preferred that the light-emitting material contains at least one of a compound represented by the following general formula (IRD-1), a compound represented by the following general formula (IRD-2), a compound represented by the following general formula (IRD-3), and a compound represented by the following general formula (IRD-4).

[Chem. 1]

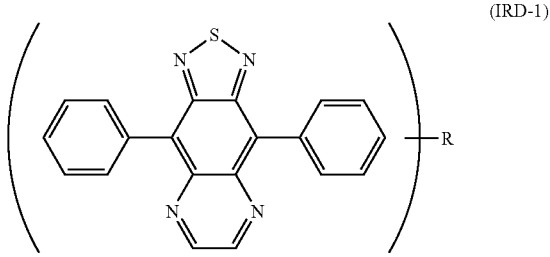

(IRD-1)

[In the general formula (IRD-1), each R independently represents an aryl group, an arylamino group, triarylamine, or a group containing at least one of the derivatives thereof.]

[Chem. 2]

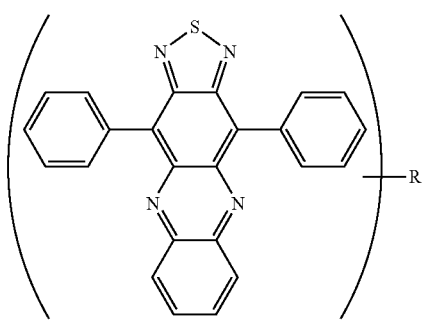

(IRD-2)

[In the general formula (IRD-2), each R independently represents an aryl group, an arylamino group, triarylamine, or a group containing at least one of the derivatives thereof.]

[Chem. 3]

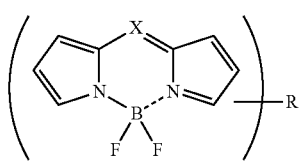

(IRD-3)

[In the general formula (IRD-3), X represents a carbon atom to which hydrogen is attached or a nitrogen atom, and R represents a hydrogen atom, an alkyl group, an aryl group which may have a substituent, an allyl group, an alkoxy group, or a heterocyclic group.]

[Chem. 4]

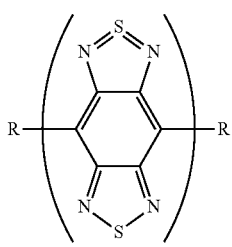

(IRD-4)

[In the general formula (IRD-4), each R independently represents a phenyl group, a thiophenyl group, a furyl group, or a group containing at least one of the derivatives thereof.]

According to this, the light-emitting layer can be made to emit light in a near-infrared region.

In the light-emitting device of the invention, it is preferred that the host material contains a compound represented by the following formula IRH-1.

[Chem. 5]

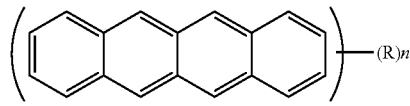

IRH-1

[In the formula IRH-1, n represents a natural number of 1 to 12, and R each independently represents a hydrogen atom, an alkyl group, an aryl group which may have a substituent, or an arylamino group.]

According to this, the light-emitting layer can be made to serve as a layer which emits visible light, and specifically, can be made to emit green light.

In the light-emitting device of the invention, it is preferred that the content of the light-emitting material in the light-emitting layer is 4.0 wt % or less.

According to this, in the light-emitting layer, a carrier injected into the light-emitting layer is not only used for recombination in the light-emitting material, but also can be used for recombination in the host material, and therefore, the light-emitting element can be made to reliably emit visible light with a luminance of 5 cd/m$^2$ or more. Further, the balance between the luminous efficiency and the life of the light-emitting element can be made excellent.

In the light-emitting device of the invention, it is preferred that the light-emitting element includes an electron transport layer which is provided between the light-emitting layer and the cathode.

According to this, the electron transport layer can be applied as a layer which emits visible light.

In the light-emitting device of the invention, it is preferred that the electron transport layer is constituted by including a compound having an anthracene skeleton.

According to this, the electron transport layer can be made to serve as a layer which emits visible light, and specifically, can be made to emit blue light In the light-emitting device of the invention, it is preferred that the thickness of the electron transport layer is 20 nm or more and 200 nm or less.

According to this, the light-emitting element reliably emits visible light with a luminance of 5 cd/m$^2$ or more.

In the light-emitting device of the invention, it is preferred that the thickness of the light-emitting layer is 5 nm or more and 100 nm or less.

According to this, the light-emitting element reliably emits visible light with a luminance of 5 cd/m$^2$ or more.

An electronic apparatus of the invention is characterized by including the light-emitting device of the invention.

Such an electronic apparatus includes the light-emitting device which is proved to be not a defective product, and therefore has high reliability.

An inspection method of the invention is characterized by including performing an inspection by observing visible light with a luminance of 5 cd/m$^2$ or more emitted by applying a current between the anode and the cathode at a current density of 300 mA/cm$^2$ or less in the light-emitting device of the invention.

According to such an inspection method, it can be easily found whether the light-emitting device is a defective product or not.

DETAILED DESCRIPTION

Hereinafter, a light-emitting device, an electronic apparatus, and an inspection method of the invention will be described with reference to preferred embodiments shown in the accompanying drawings.

First, the light-emitting device of the invention will be described.

Figure 1:
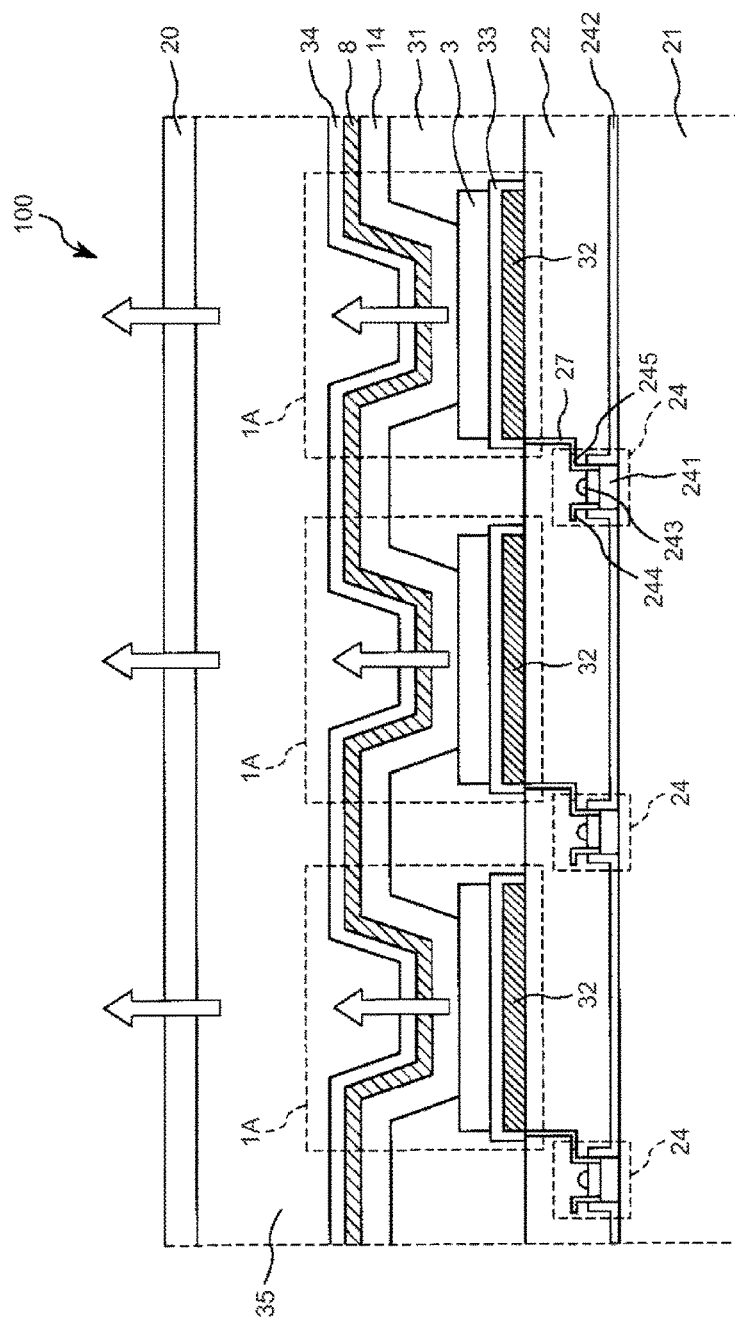
FIG. 1 is a longitudinal cross-sectional view showing an embodiment of a light-emitting device.
Figure 2:
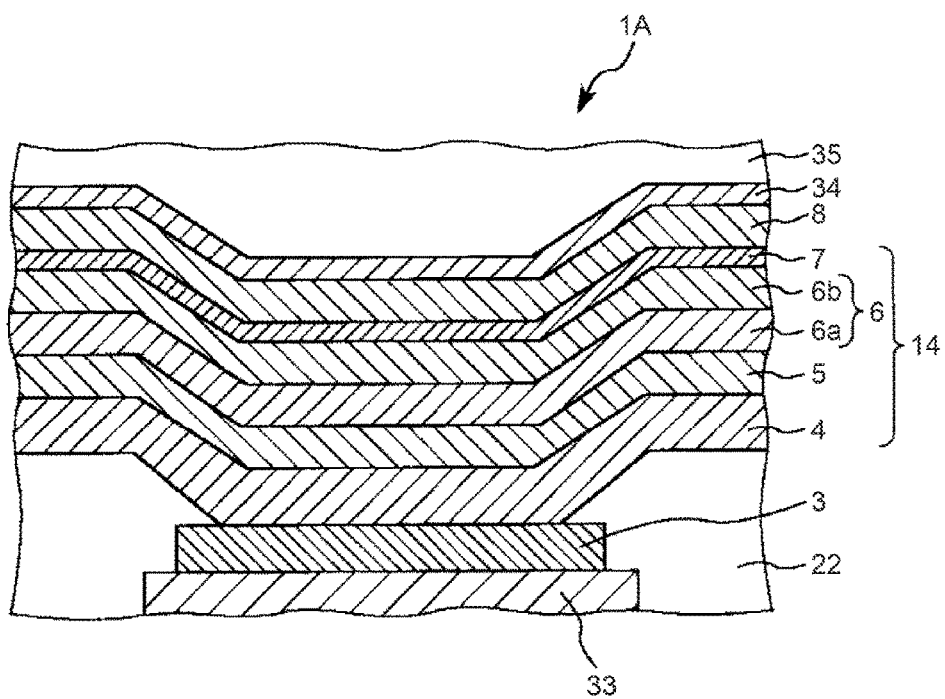
FIG. 2 is a partially enlarged cross-sectional view schematically enlarging a light-emitting element included in the light-emitting device shown in FIG. 1.

FIG. 1 is a longitudinal cross-sectional view showing an embodiment of the light-emitting device of the invention. FIG. 2 is a partially enlarged cross-sectional view schematically enlarging a light-emitting element included in the light-emitting device shown in FIG. 1. Incidentally, hereinafter, for the sake of convenience of explanation, a description will be made by referring to the upper side and the lower side in FIGS. 1 and 2 as "upper" and "lower", respectively.

A light-emitting device 100 shown in FIG. 1 includes a substrate 21, a plurality of light-emitting elements 1A, and a plurality of driving transistors 24 for driving the respective light-emitting elements 1A. Here, the light-emitting device 100 has a top emission structure in which light emitted from the opposite side of the substrate 21 (on the side of the below-mentioned sealing substrate 20) is extracted.

On the substrate 21, the plurality of driving transistors 24 are provided, and a planarization layer 22 composed of an insulating material is formed so as to cover these driving transistors 24.

Each driving transistor 24 includes a semiconductor layer 241 composed of silicon, a gate insulating layer 242 formed on the semiconductor layer 241, a gate electrode 243 formed on the gate insulating layer 242, a source electrode 244, and a drain electrode 245.

In addition, on the planarization layer, a reflective film 32 and a corrosion preventive film 33 are provided and stacked in this order corresponding to each driving transistor 24.

Further, on each corrosion preventive film 33, the light-emitting element 1A is provided corresponding thereto, that is, corresponding to the driving transistor 24.

In the light-emitting element 1A, an anode 3, a stacked body (organic EL light-emitting section) 14, a cathode 8, and a cathode cover 34 are stacked in this order on the corrosion preventive film 33, and in the stacked body 14, a hole injection layer 4, a light-emitting layer 5, a first electron transport layer 6b, a second electron transport layer 6a, an electron injection layer 7, and a cathode 8 are stacked in this order as shown in FIG. 2.

Between the adjacent light-emitting elements 1A having such a configuration, a partition wall 31 is provided. According to this, the respective light-emitting elements 1A are provided individually.

In this embodiment, in each light-emitting element 1A, the reflective film 32, the corrosion preventive film 33, and the anode 3 are provided individually by being divided with the partition wall 31, and the stacked body 14, the cathode 8, and the cathode cover 34 are integrally provided. According to such a configuration, the anode 3 of each light-emitting element 1A constitutes a pixel electrode, and further, the cathode 8 of each light-emitting element 1A constitutes a common electrode. In addition, the anode 3 of each light-emitting element 1A is electrically connected to a drain electrode 245 of each driving transistor 24 through a conductive section (wiring) 27.

In this manner, in the light-emitting device 100 including the light-emitting element 1A, by controlling the operation of the light-emitting element 1A using the driving transistor 24, that is, by controlling the application of a voltage to the light-emitting element 1A, light emission can be achieved.

The light-emitting element 1A included in the light-emitting device 100 having such a configuration emits light in a near-infrared region, however, a detailed description of the light-emitting element 1A will be made later.

Further, on the light-emitting elements 1A, an epoxy layer 35 constituted by an epoxy resin is formed so as to cover the light-emitting elements 1A.

On the epoxy layer 35, a sealing substrate 20 is provided so as to cover the epoxy layer 35. According to this, airtightness of the light-emitting elements 1A is ensured, and penetration of oxygen and water can be prevented, and therefore, the reliability of the light-emitting elements 1A can be improved.

The light-emitting device 100 having such a configuration can also be used as, for example, a near-infrared display for military purposes or the like.

In the light-emitting device 100 as described above, the light-emitting element 1A emits light in a near-infrared region as described above, however, hereinafter, this light-emitting element 1A will be described.

(Light-Emitting Element)

The light-emitting element (electroluminescence element) 1A shown in FIG. 2 includes an anode 3, a hole injection layer 4, a light-emitting layer 5, an electron transport layer 6, an electron injection layer 7, and a cathode 8, which are stacked in this order. That is, in the light-emitting element 1A, between the anode 3 and the cathode 8, a stacked body 14 in which the hole injection layer 4, the light-emitting layer 5, the electron transport layer 6, and the electron injection layer 7 are stacked in this order from the anode 3 side to the cathode 8 side is interposed.

In such a light-emitting element 1A, by applying a driving voltage to the anode 3 and the cathode 8, an electron is supplied (injected) to the light-emitting layer 5 from the cathode 8 side, and also a hole is supplied (injected) to the light-emitting layer 5 from the anode 3 side. Then, the hole and the electron are recombined in the light-emitting layer 5, and an exciton is generated by energy emitted at the time of this recombination, and when the exciton is returned to a ground state, energy (fluorescence or phosphorescence) is emitted (light emission). In this manner, the light-emitting element 1A emits light.

In particular, as described later, this light-emitting element 1A emits light in a near-infrared region such as a wavelength region of 700 nm or more by including at least one light-emitting material selected from a thiadiazole-based compound which is a compound represented by the following general formula (IRD-1), a thiadiazole-based compound which is a compound represented by the following general formula (IRD-2), a pyrromethene-based boron complex which is a compound represented by the following general formula (IRD-3), a benzo-bis-thiadiazole-based compound which is a compound represented by the following general formula (IRD-4), and the like. Incidentally, the "near-infrared region" as used herein refers to a wavelength region of 700 nm or more and 1500 nm or less, and the "light emission in a near-infrared region" as used herein refers to light emission having a peak of a light emission waveform in the range of 700 nm or more and 1500 nm or less.

Incidentally, in such a light-emitting element 1A, the distance between the anode 3 and the cathode 8 (that is, the average thickness of the stacked body 14) is preferably from 100 to 500 nm, more preferably from 100 to 300 nm, further more preferably from 100 to 250 nm. According to this, the driving voltage of the light-emitting element 1A can be easily and reliably made to fall within a practical range.

Hereinafter, the respective sections constituting the light-emitting element 1A will be sequentially described.

(Anode)

The anode 3 is an electrode which injects holes into the hole injection layer 4. As the constituent material of the anode 3, a material having a large work function and excellent electrical conductivity is preferably used.

Examples of the constituent material of the anode 3 include oxides such as ITO (Indium Tin Oxide), IZO (Indium Zinc Oxide), $In_2O_3$, $SnO_2$, Sb-containing $SnO_2$, and Al-containing ZnO, Au, Pt, Ag, Cu, and an alloy containing any of these materials, and among these, it is possible to use one type or two or more types in combination.

In particular, the anode 3 is preferably constituted by ITO. ITO is a material which is transparent, and also has a large work function and excellent electrical conductivity. According to this, holes can be efficiently injected from the anode 3 into the hole injection layer 4.

Further, it is preferred that the surface of the anode 3 on the hole injection layer 4 side (the upper surface in FIGS. 1 and 2) is subjected to a plasma treatment. According to this, the chemical and mechanical stability of the joining surface of the anode 3 and the hole injection layer 4 can be increased. As a result, the hole injection property from the anode 3 into the hole injection layer 4 can be improved.

The average thickness of such an anode 3 is not particularly limited, but is preferably from about 10 to 200 nm, more preferably from about 50 to 150 nm.

(Cathode)

On the other hand, the cathode 8 is an electrode which injects electrons into the electron transport layer 6 through the below-mentioned electron injection layer 7. As the constituent material of the cathode 8, a material having a small work function is preferably used.

Examples of the constituent material of the cathode 8 include Li, Mg, Ca, Sr, La, Ce, Er, Eu, Sc, Y, Yb, Ag, Cu, Al, Cs, Rb, and an alloy containing any of these materials, and among these, it is possible to use one type or two or more types in combination (for example, as a stacked body of a plurality of layers, a mixed layer of a plurality of types, or the like).

In particular, in the case where an alloy is used as the constituent material of the cathode 8, it is preferred to use an alloy containing a stable metal element such as Ag, Al, or Cu, specifically, an alloy such as MgAg, AlLi, or CuLi. By using such an alloy as the constituent material of the cathode 8, the electron injection efficiency and stability of the cathode 8 can be improved.

Since the light-emitting element 1A of this embodiment is a top emission type so that it is necessary to transmit light from the cathode 8 side, the average thickness of the cathode 8 is preferably from about 1 to 50 nm.

Further, in the case where the light-emitting element 1A of this embodiment is a bottom emission type, a light transmission property is not particularly required for the cathode 8, and therefore, the average thickness of the cathode 8 is preferably from about 100 to 10000 nm, more preferably from about 100 to 500 nm.

(Hole Injection Layer)

The hole injection layer 4 has a function to improve the hole injection efficiency from the anode 3 (that is, has a hole injection property). According to this, the luminous efficiency of the light-emitting element 1A can be increased. Here, the hole injection layer 4 also has a function to transport holes injected from the anode 3 to the light-emitting layer 5 (that is, has a hole transport property). Therefore, since the hole injection layer 4 has a hole transport property as described above, it can also be said that the hole injection layer 4 is a hole transport layer. Incidentally, a hole transport layer constituted by a material different from that of the hole injection layer 4 (for example, an amine-based compound such as a benzidine derivative) may be separately provided between the hole injection layer 4 and the light-emitting layer 5.

This hole injection layer 4 contains a material having a hole injection property (a hole-injecting material).

The hole-injecting material to be contained in this hole injection layer 4 is not particularly limited, and examples thereof include copper phthalocyanine and amine-based materials such as 4,4',4"-tris(N,N-phenyl-3-methylphenylamino)triphenylamine (m-MTDATA) and N,N'-bis-(4-diphenylamino-phenyl)-N,N'-diphenyl-biphenyl-4-4'-diamine.

Above all, as the hole-injecting material to be contained in the hole injection layer 4, from the viewpoint of excellent hole injection property and hole transport property, it is preferred to use an amine-based material, and it is more preferred to use a diaminobenzene derivative, a benzidine derivative (a material having a benzidine skeleton), a tri-amine-based compound and a tetraamine-based compound having both of a "diaminobenzene" unit and a "benzidine" unit in the molecule (specifically, for example, compounds represented by the following formulae HIL1 to HIL27).

[Chem. 6]
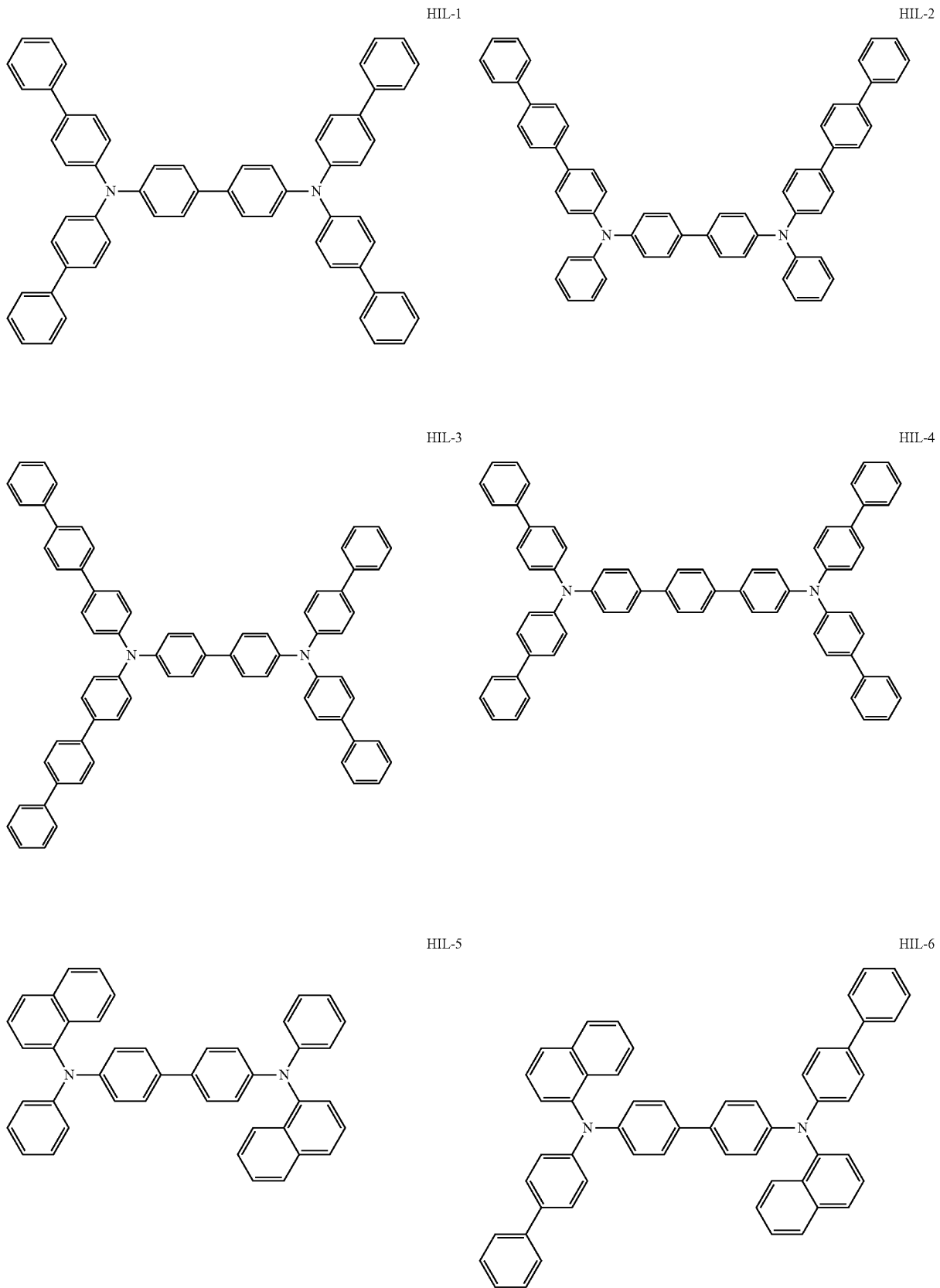

-continued
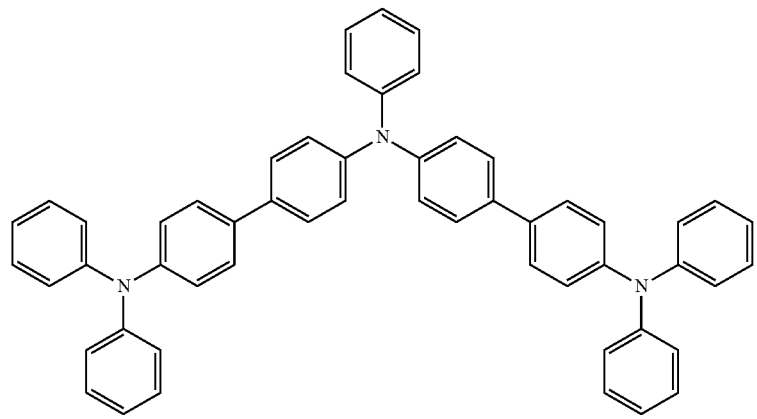
HIL-7
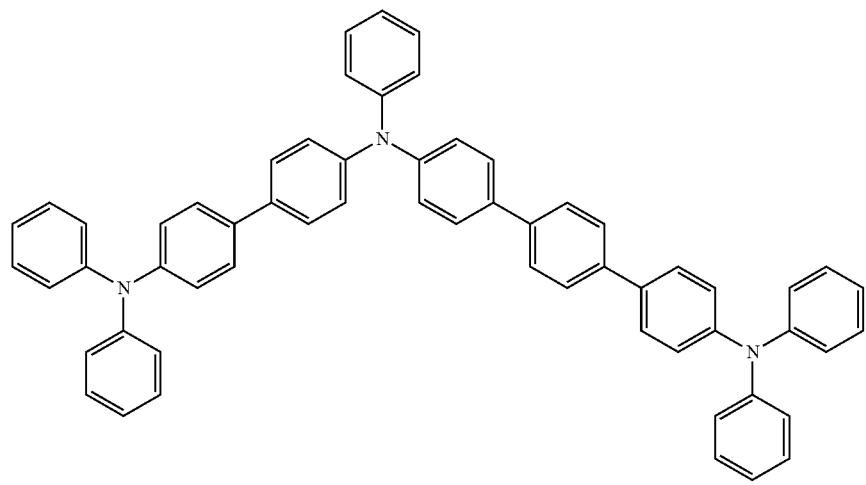
HIL-8
[Chem. 7]
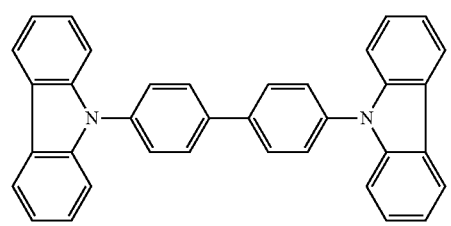
HIL-9
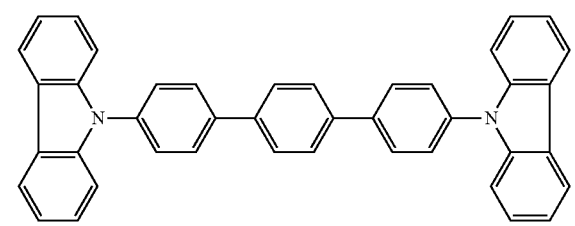
HIL-10
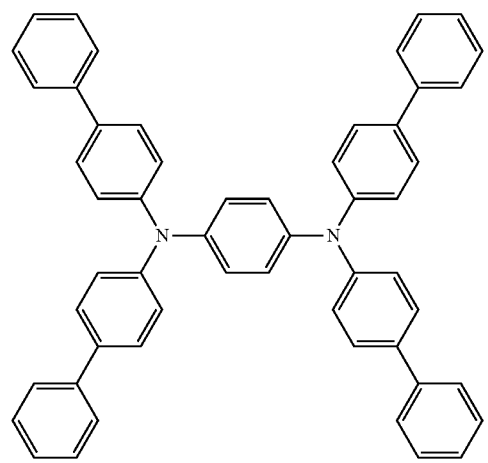
HIL-11
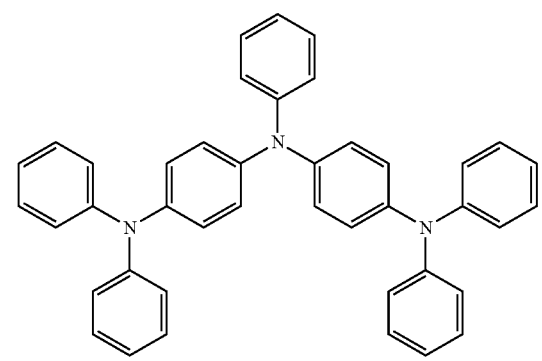
HIL-12

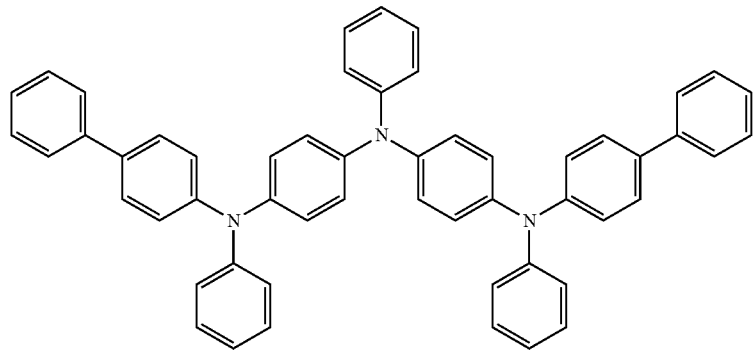
HIL-13
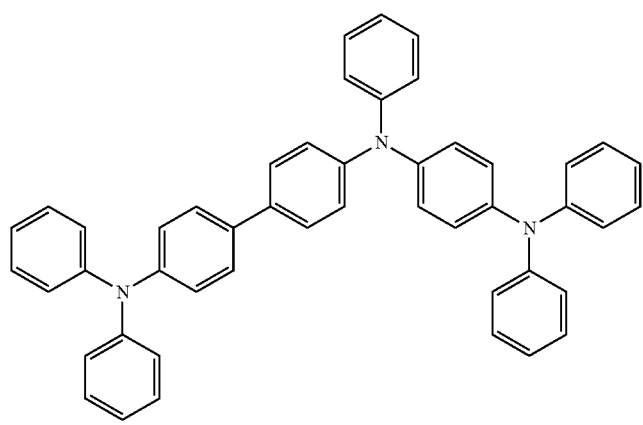
HIL-14
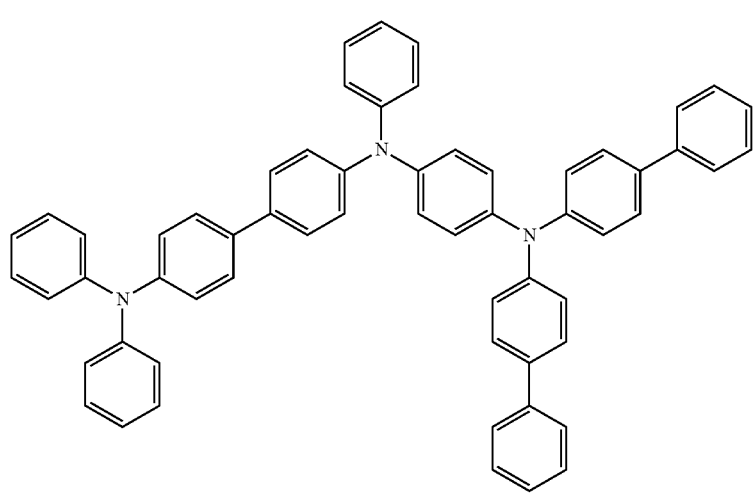
HIL-15

HIL-16
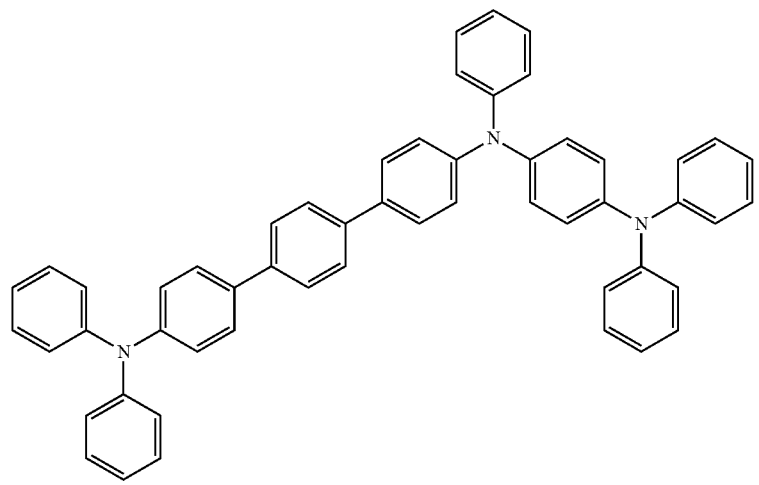
HIL-17
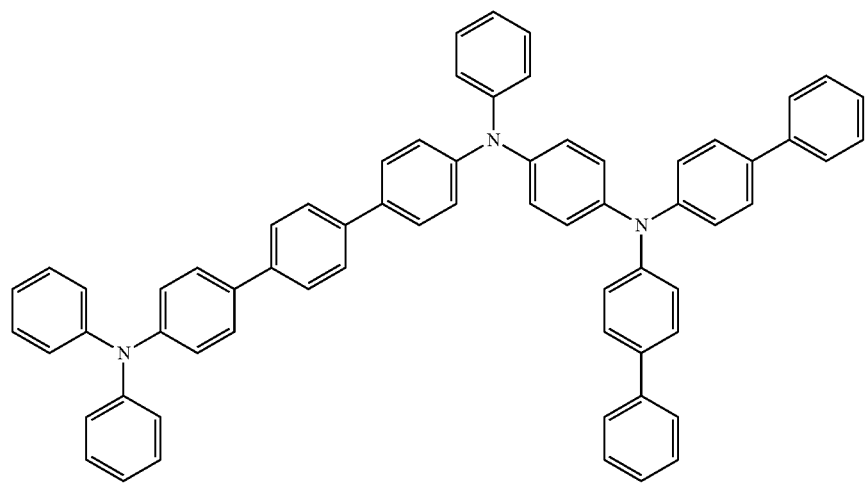
HIL-18
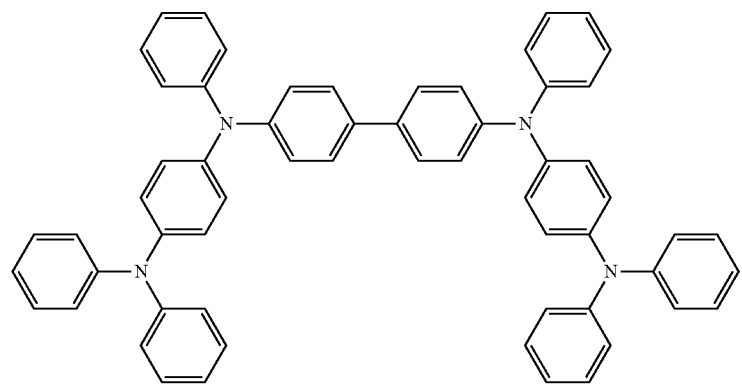

HIL-19
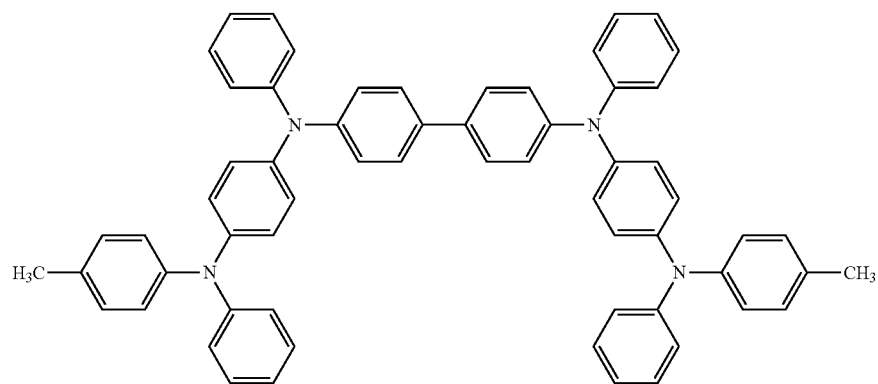
HIL-20
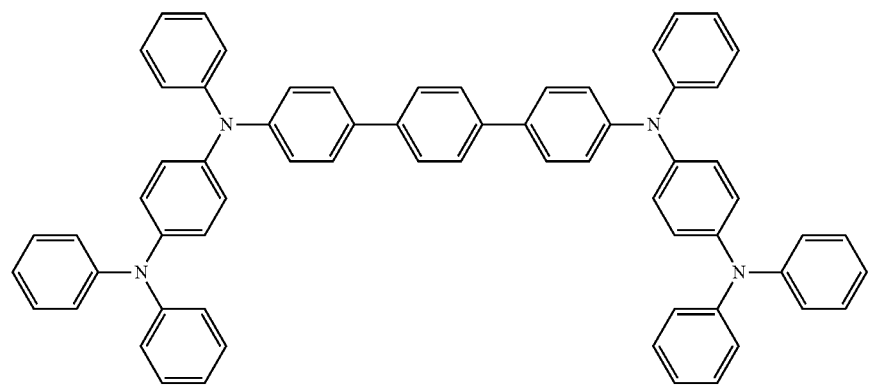
HIL-21
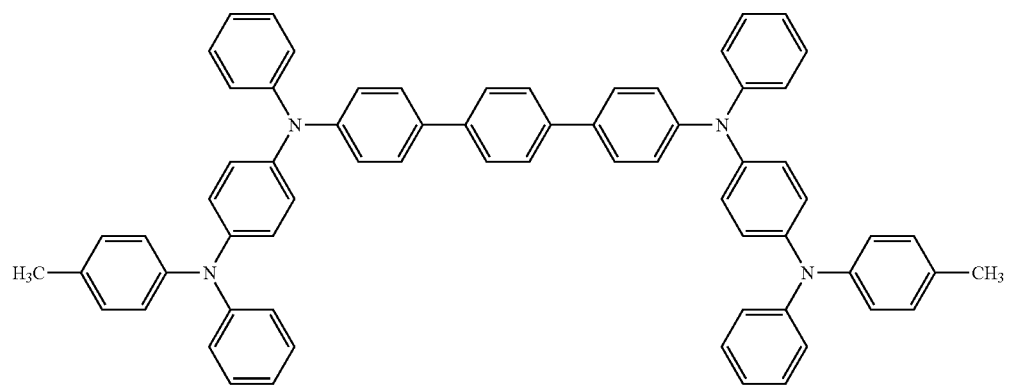

[Chem. 8]
HIL-22
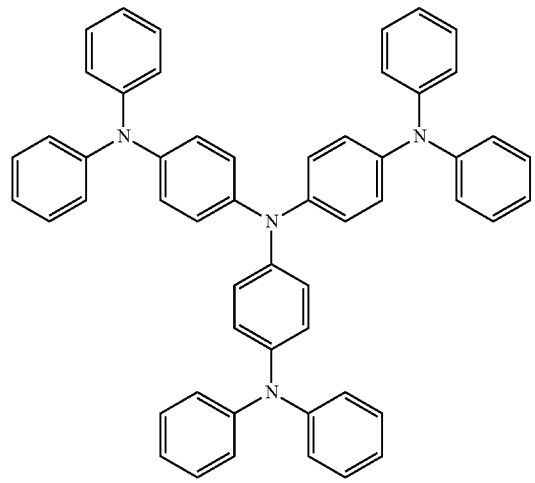
HIL-23
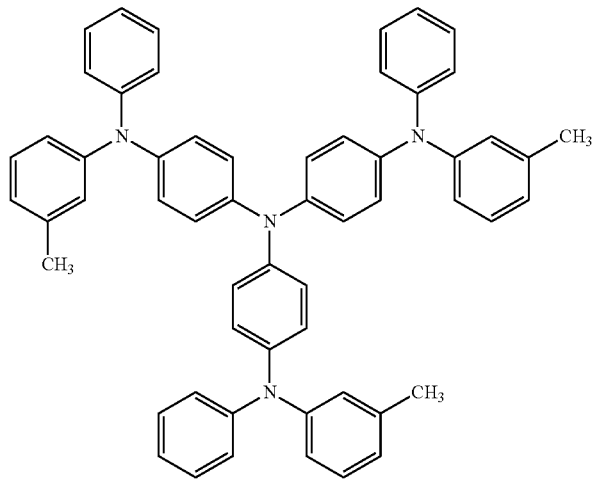
HIL-24
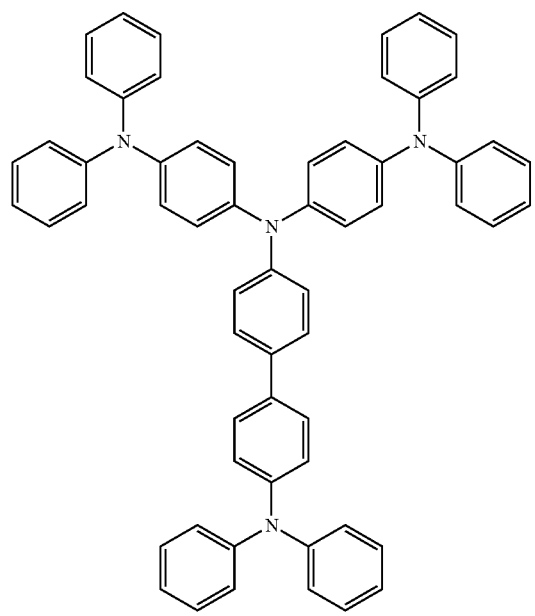
HIL-25
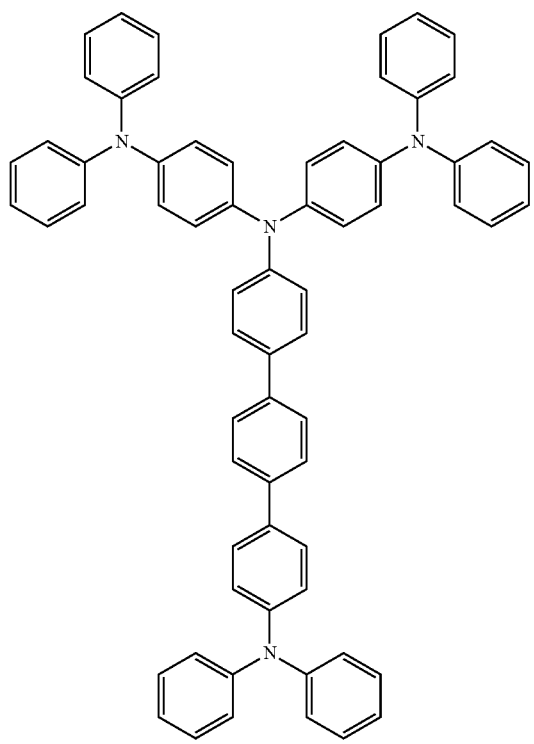

-continued

HIL-26

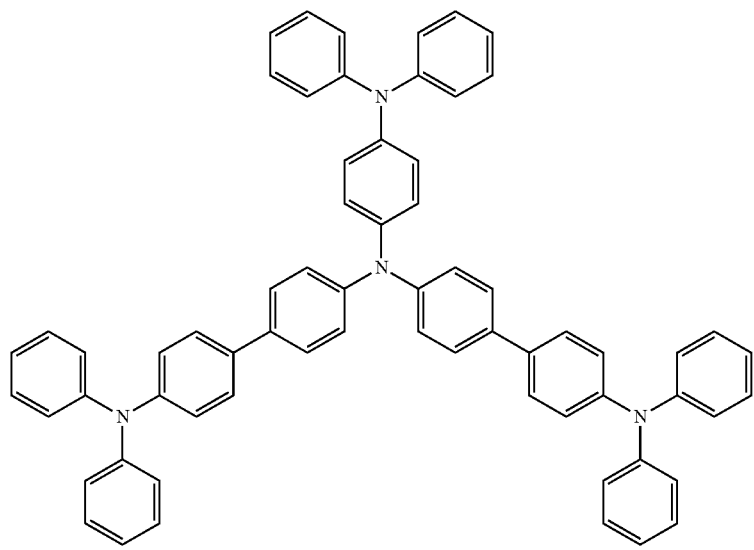

HIL-27

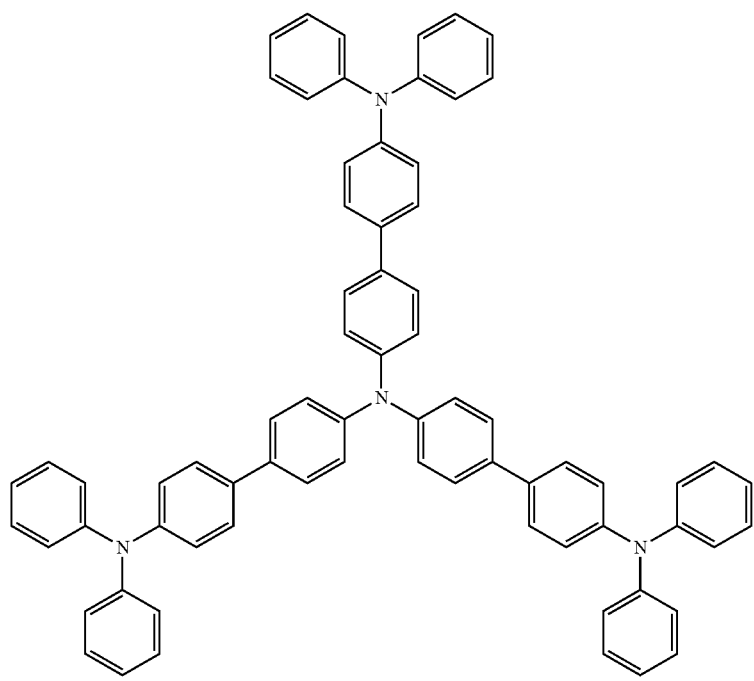

Further, it is preferred that a difference between the LUMO of the constituent material of the hole injection layer 4 and the LUMO of a host material to be used in the light-emitting layer 5 is 0.5 eV or more. According to this, electrons can be prevented from coming out from the light-emitting layer 5 to the hole injection layer 4, and thus, the luminous efficiency can be increased.

Further, the HOMO of the constituent material of the hole injection layer 4 is preferably 4.7 eV or more and 5.6 eV or less, and the LUMO of the constituent material of the hole injection layer 4 is preferably 2.2 eV or more and 3.0 eV or less.

(Light-Emitting Layer)

The light-emitting layer 5 emits light by applying a current between the anode 3 and cathode 8 described above.

The light-emitting layer 5 is not particularly limited as long as it can emit light in a near-infrared region, but is constituted by including a light-emitting material which functions as a light-emitting dopant.

Examples of the light-emitting material include a thiadiazole-based compound which is a compound represented by the following general formula (IRD-1) (hereinafter also simply referred to as "thiadiazole-based compound 1"), a thiadiazole-based compound which is a compound represented by the following general formula (IRD-2) (hereinafter also simply referred to as "thiadiazole-based compound 2"), a pyrromethene-based boron complex which is a compound represented by the following general formula (IRD-3) (hereinafter also simply referred to as "pyrromethene-based boron complex"), and a benzo-bis-thiadiazole-based compound which is a compound represented by the following general formula (IRD-4) (hereinafter also simply referred to as "benzo-bis-thiadiazole-based compound"), and among these, it is possible to use one type or two or more types in combination. According to this, the light-emitting layer 5 can be made to emit light in a near-infrared region.

[Chem. 9]

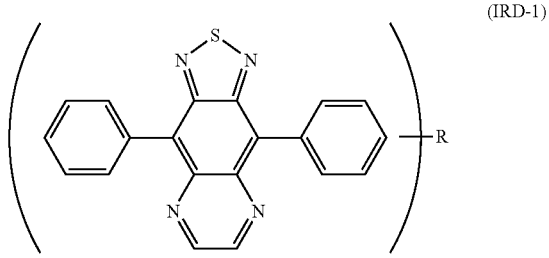

(IRD-1)

[In the general formula (IRD-1), each R independently represents an aryl group, an arylamino group, triarylamine, or a group containing at least one of the derivatives thereof.]

Examples of each group R in the general formula (IRD-1) include an aryl group, an arylamino group, triarylamine, and derivatives thereof, and among these, it is possible to use two or more types in combination. The light-emitting layer 5 containing the thiadiazole-based compound 1 including such a group R as a light-emitting dopant can obtain light emission in a near-infrared region.

Specific examples of the thiadiazole-based compound 1 including the group R as described above include compounds represented by the following formulae IRD-11 to IRD-18 and derivatives thereof.

[Chem. 10]

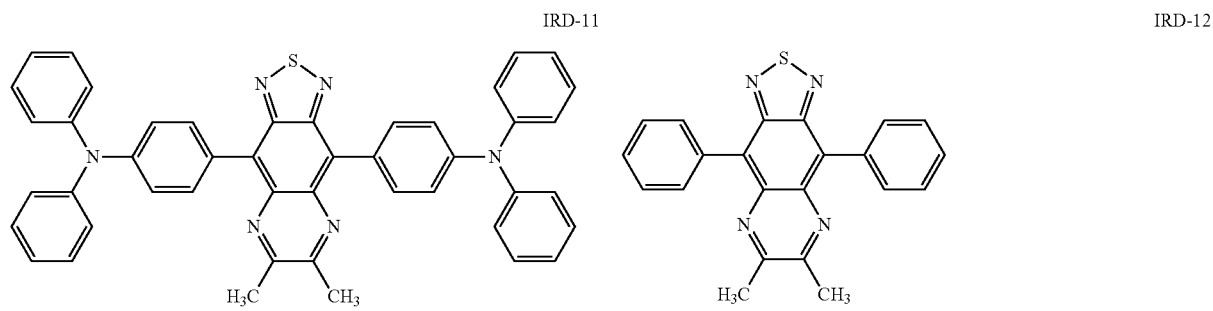

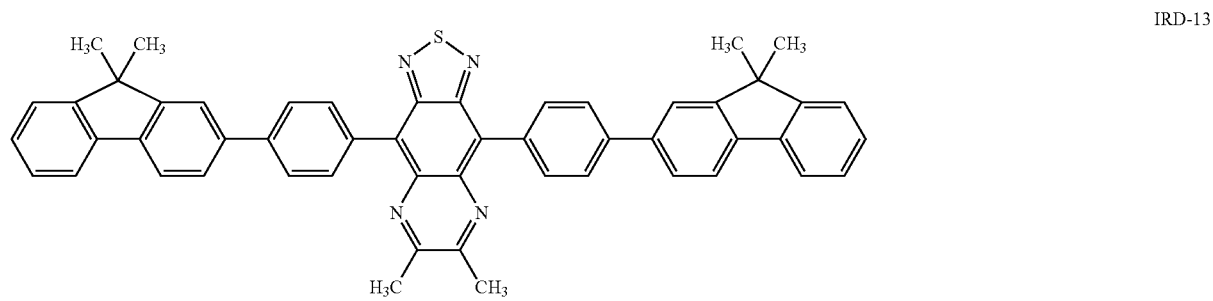

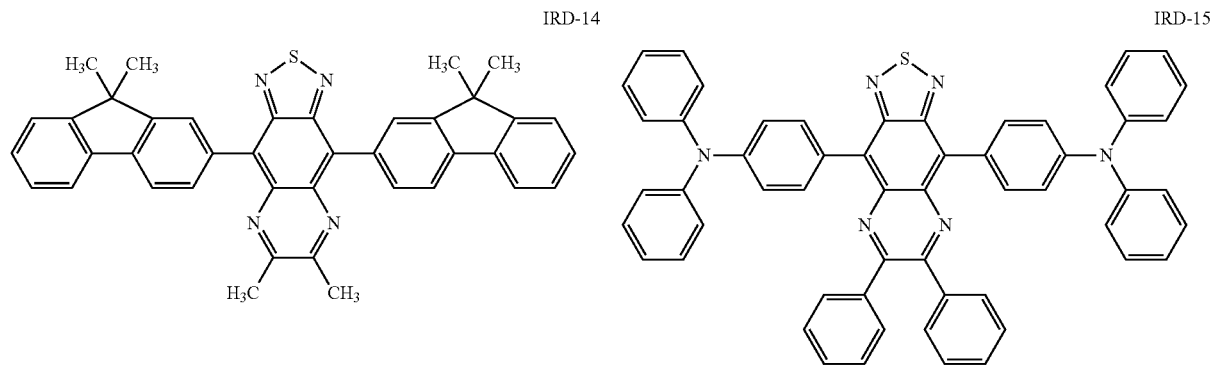

-continued

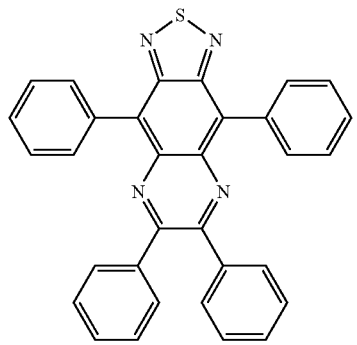
IRD-16

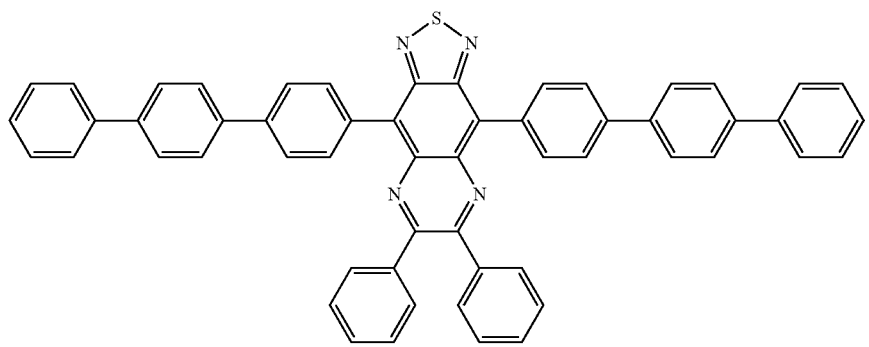
IRD-17

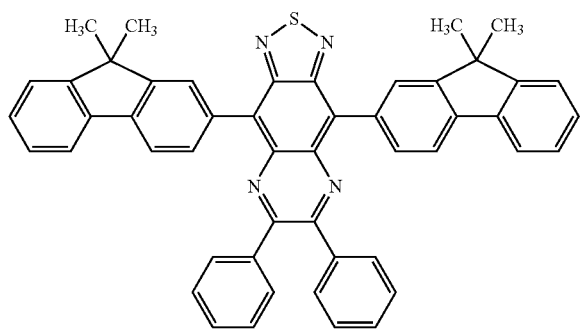
IRD-18

[Chem. 11]

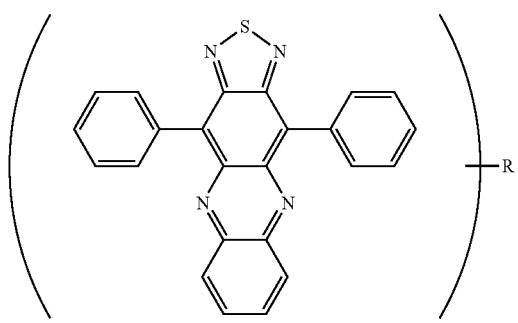
(IRD-2)

[In the general formula (IRD-2), each R independently represents an aryl group, an arylamino group, triarylamine, or a group containing at least one of the derivatives thereof.]

Examples of each group R in the general formula (IRD-2) include an aryl group, an arylamino group, triarylamine, and derivatives thereof, and among these, it is possible to use two or more types in combination. The light-emitting layer 5 containing the thiadiazole-based compound 2 including such a group R as a light-emitting dopant can obtain light emission in a near-infrared region.

Specific examples of the thiadiazole-based compound 2 including the group R as described above include compounds represented by the following formulae IRD-21 to IRD-26 and derivatives thereof.

[Chem. 12]

IRD-21
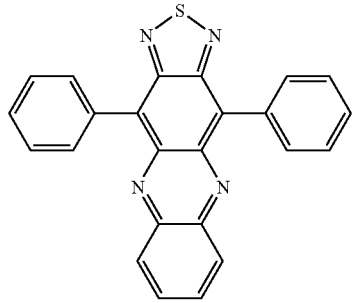

IRD-22
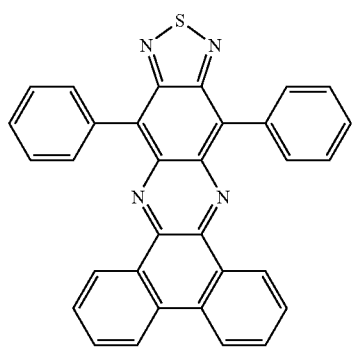

IRD-23
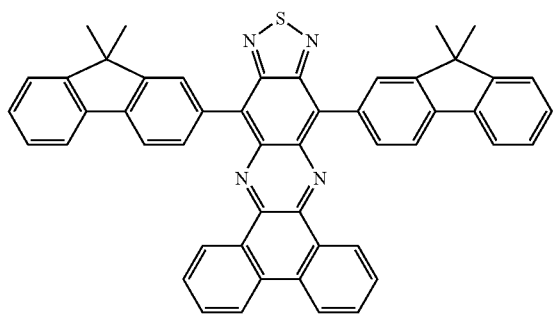

IRD-24
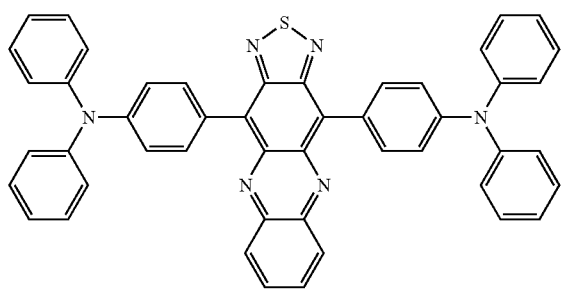

IRD-25
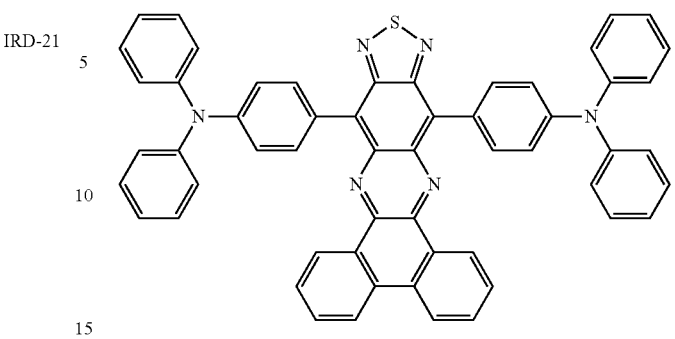

IRD-26
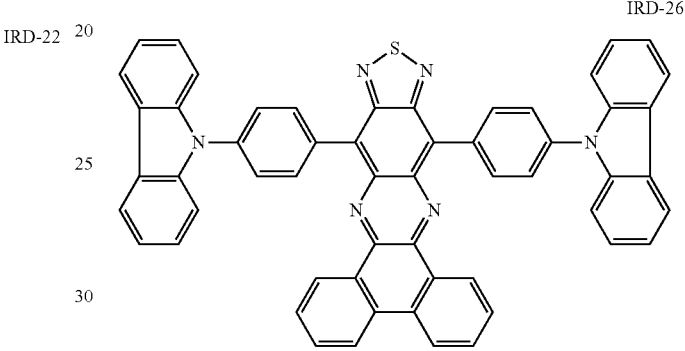

[Chem. 13]

(IRD-3)
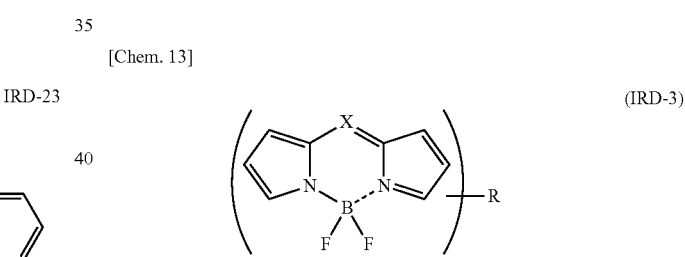

[In the general formula (IRD-3), X represents a carbon atom to which hydrogen is attached or a nitrogen atom, and R represents a hydrogen atom, an alkyl group, an aryl group which may have a substituent, an allyl group, an alkoxy group, or a heterocyclic group.]

Here, the heterocyclic group to be used as R in the general formula (IRD-3) is not particularly limited, however, it is preferred to use a 5-membered heterocyclic group such as pyrrole, furan, or thiophene, or a 6-membered heterocyclic group such as pyridine.

The light-emitting layer 5 containing such a pyrromethene-based boron complex can obtain light emission in a near-infrared region.

Further, the light-emitting material to be used in the light-emitting layer 5 may be any as long as it is a compound represented by the above general formula (IRD-3) and can emit light in a near-infrared region, however, specific examples thereof include compounds represented by the following formulae IRD-31 to IRD-35 and derivatives thereof.

[Chem. 14]

IRD-31
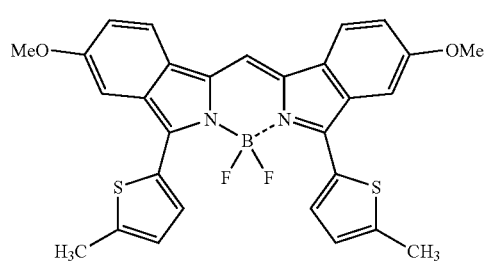

IRD-32
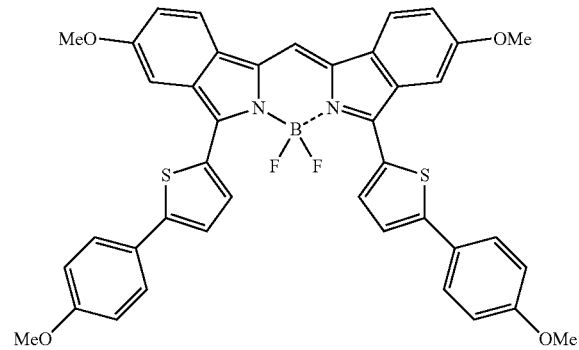

IRD-33

IRD-34
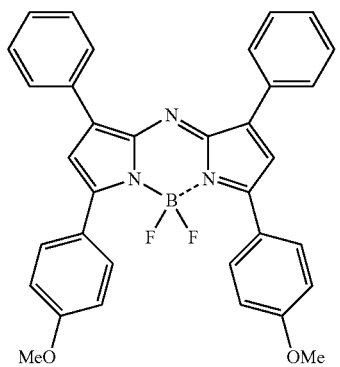

IRD-35
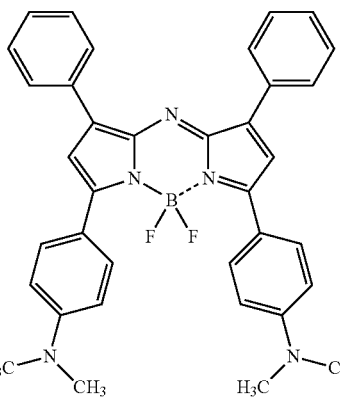

[Chem. 15]

(IRD-4)
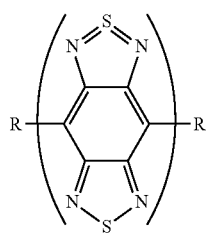

[In the general formula (IRD-4), each R independently represents a phenyl group, a thiophenyl group, a furyl group, or a group containing at least one of the derivatives thereof.]

Each group R in the general formula (IRD-4) is not particularly limited as long as it is a phenyl group, a thiophenyl group, a furyl group, or a group containing at least one of the derivatives thereof, however, examples thereof include a phenyl group, a thiophenyl group (thiophene group), a furyl group (furan group), an oxazole group, and an oxadiazole group, and among these, it is preferred to use two or more types in combination. According to this, the light-emitting layer 5 containing the benzo-bis-thiadiazole-based compound including such a group R as a light-emitting dopant obtains light emission in a near-infrared region, particularly obtains light emission in a wavelength region of 850 nm or more and 1500 nm or less.

Specific examples of the benzo-bis-thiadiazole-based compound including the group R as described above include compounds represented by the following formulae IRD-41 to IRD-45 and derivatives thereof.

[Chem. 16]

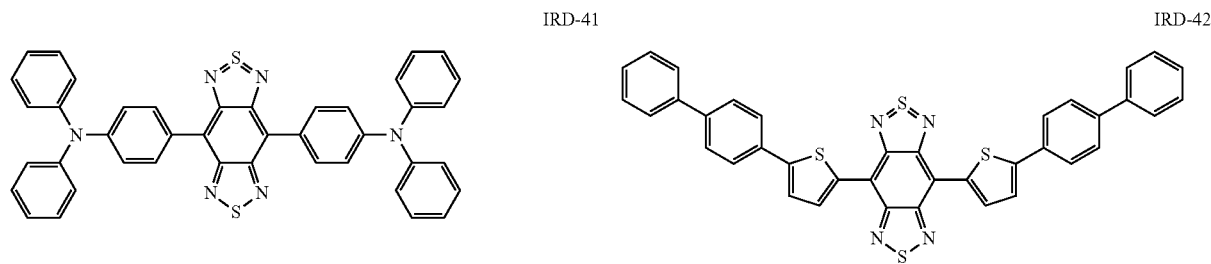

IRD-41 IRD-42

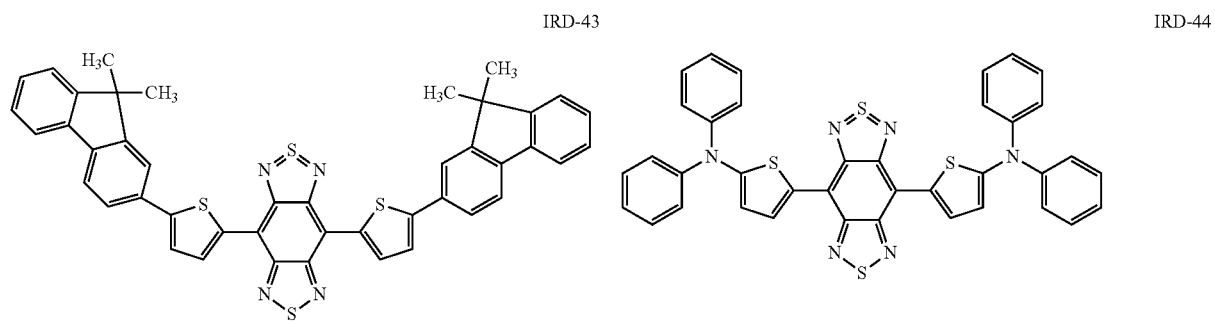

IRD-43 IRD-44

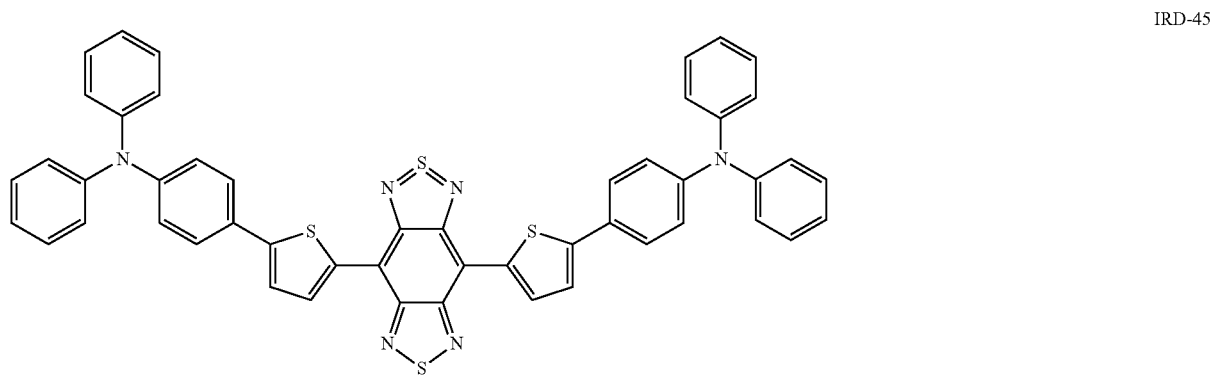

IRD-45

Incidentally, the light-emitting layer 5 may contain a light-emitting material (any of various types of fluorescent materials and various types of phosphorescent materials) other than the above-mentioned light-emitting material.

Further, the light-emitting layer 5 is constituted by including, in addition to the light-emitting material as described above, a host material to which this light-emitting material is added (held) as a guest material (dopant). This host material has a function to recombine a hole and an electron to generate an exciton, and also to transfer the energy of the exciton (Forster-transfer or Dexter-transfer) to the light-emitting material to excite the light-emitting material. Due to this, the luminous efficiency of the light-emitting element 1A can be increased. Such a host material can be used by, for example, doping the light-emitting material which is a guest material as a dopant into the host material.

The host material to be used in the light-emitting layer 5 is not particularly limited, but is particularly preferably an anthracene-based material which is a compound represented by the following formula IRH-1.

[Chem. 17]

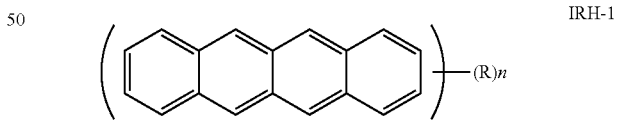

IRH-1

[In the formula IRH-1, n represents a natural number of 1 to 12, and R each independently represents a hydrogen atom, an alkyl group, an aryl group which may have a substituent, or an arylamino group.]

The various types of compounds (the benzo-bis-thiadiazole-based compounds, and the like) exemplified as the light-emitting material as described above have high polarity (large polarization), and therefore, in the case where such a compound is used as the light-emitting material, when the concentration thereof in the light-emitting layer is high, concentration quenching which is a phenomenon in which luminous efficiency is decreased due to the interaction between the molecules of the light-emitting material is likely to occur.

On the other hand, the tetracene-based material has low polarity (small polarization). Therefore, by using the tetracene-based material as the host material, the interaction between the molecules of the light-emitting material as described above is reduced, and therefore, the concentration quenching property can be reduced.

On the other hand, for example, in the case where $Alq_3$ having high polarity (large polarization) is used as the host material, the polarity of both of the host material and the light-emitting material is high (the polarization is large), and therefore, the interaction between the molecules of the light-emitting material is likely to occur, and thus, the concentration quenching property is increased.

Further, an anthracene-based material which is an acene-based material in the same manner as the tetracene-based material has an effect of reducing the concentration quenching property in the case where it is used as the host material, however, the luminous efficiency is decreased as compared with the case where the tetracene-based material is used as the host material. It is considered to be because when the anthracene-based material is used as the host material, the energy transfer from the host material to the light-emitting material is not sufficient, and the probability that an electron injected into the LUMO of the host material penetrates toward the anode side is high. Due to this, it cannot be said that the anthracene-based material is a suitable host material. Incidentally, such a phenomenon occurs in the same manner also in the case of a pentacene-based material other than the anthracene-based material.

For this reason, by using the tetracene-based material (acene-based material) as the host material, the luminous efficiency of the light-emitting element 1A can be increased, and therefore, the tetracene-based material is favorably used as the host material.

Further, the tetracene-based material has excellent resistance to electrons and holes. In addition, the tetracene-based material also has excellent thermal stability. Due to this, the life of the light-emitting element 1A can be extended. Further, since the tetracene-based material has excellent thermal stability, in the case where the light-emitting layer is formed using a gas phase deposition method, the decomposition of the host material due to heat during deposition can be prevented. Due to this, the light-emitting layer having excellent film quality can be formed. As a result, also from this point of view, the luminous efficiency of the light-emitting element 1A can be increased and also the life thereof can be extended.

In addition, the tetracene-based material hardly emits light itself, and therefore, it is also possible to prevent the host material from adversely affecting the emission spectrum of the light-emitting element 1A.

Further, the tetracene-based material to be used as the host material is not particularly limited as long as it is represented by the above formula IRH-1 and also can exhibit the function as the host material as described above, however, it is preferred to use a compound represented by the following formula IRH-2, and it is more preferred to use a compound represented by the following formula IRH-3.

[Chem. 18]

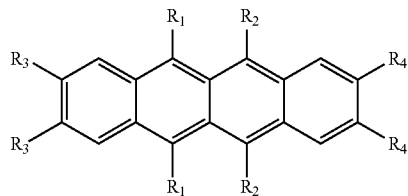

IRH-2

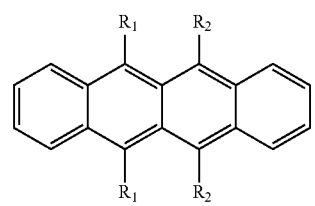

IRH-3

[In the formulae IRH-2 and IRH-3, $R_1$ to $R_4$ each independently represent a hydrogen atom, an alkyl group, an aryl group which may have a substituent, or an arylamino group, and $R_1$ to $R_4$ may be the same as or different from one another.]

Further, the tetracene-based material to be used as the host material is preferably constituted by a carbon atom and a hydrogen atom. According to this, the polarity of the host material is decreased, and thus, an undesirable interaction between the host material and the light-emitting material can be prevented from occurring. Due to this, the luminous efficiency of the light-emitting element 1A can be increased. In addition, the resistance of the host material to a electron and holes can be increased. As a result, the life of the light-emitting element 1A can be extended.

Specifically, as the tetracene-based material, for example, it is preferred to use compounds represented by the following formulae H-1 to H-27.

[Chem. 19]

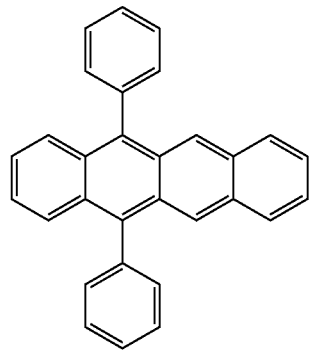

H-1

H-2
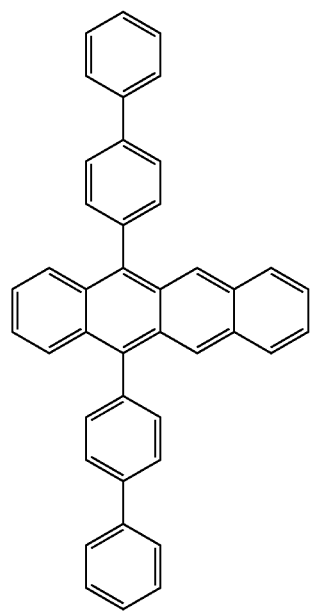
H-3
H-4
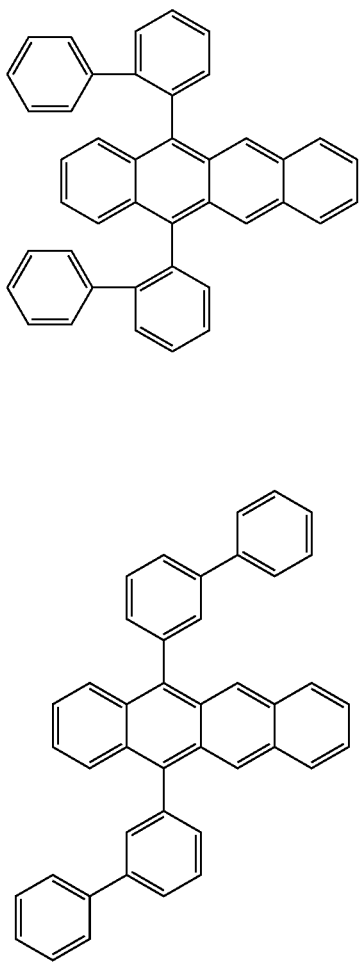
H-5
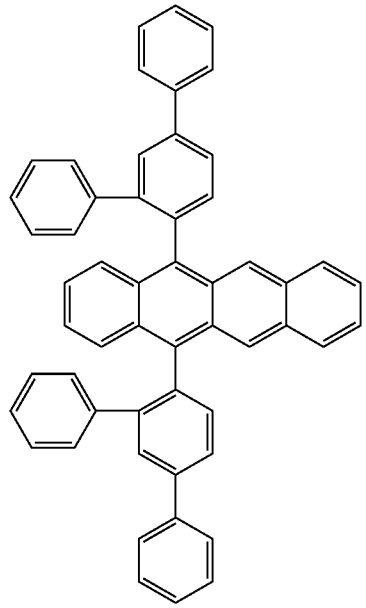
H-6
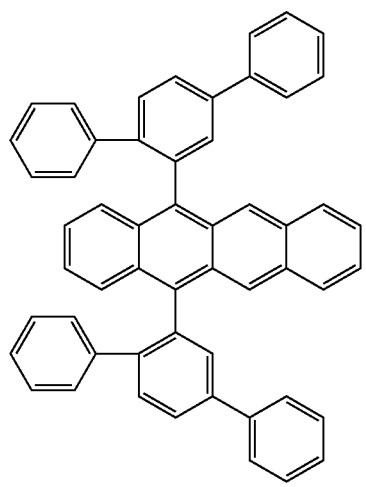
H-7

H-8
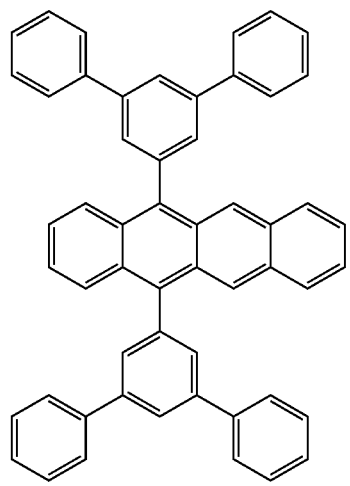
H-10
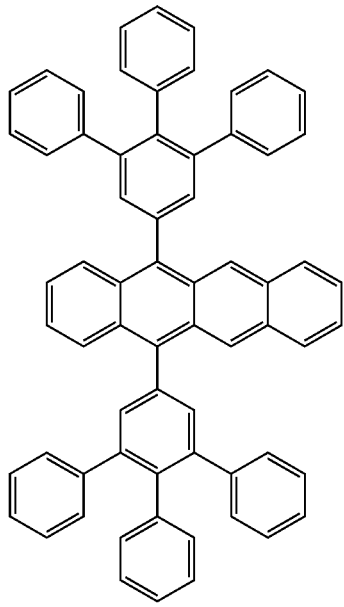
H-11
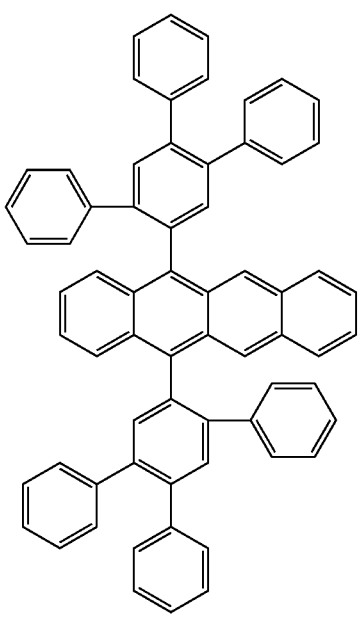
H-9
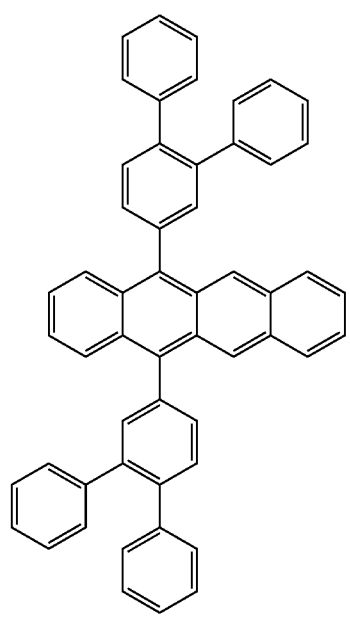
[Chem. 20]
H-12
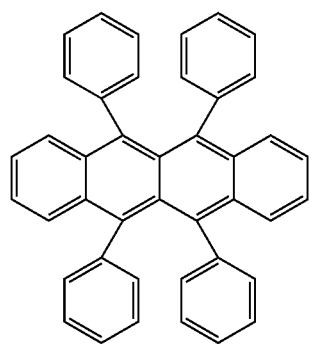

H-13
H-14
H-15
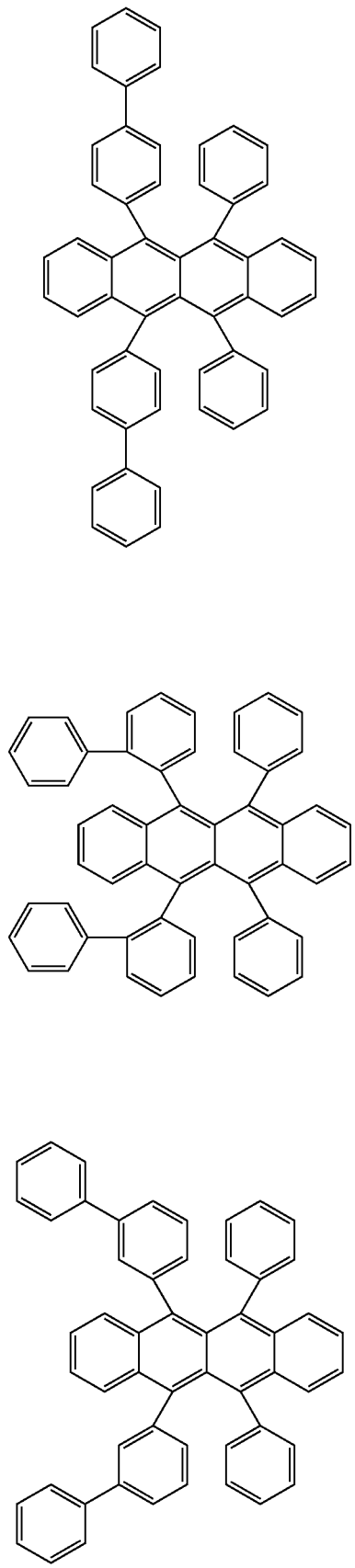
H-16
H-17
H-18
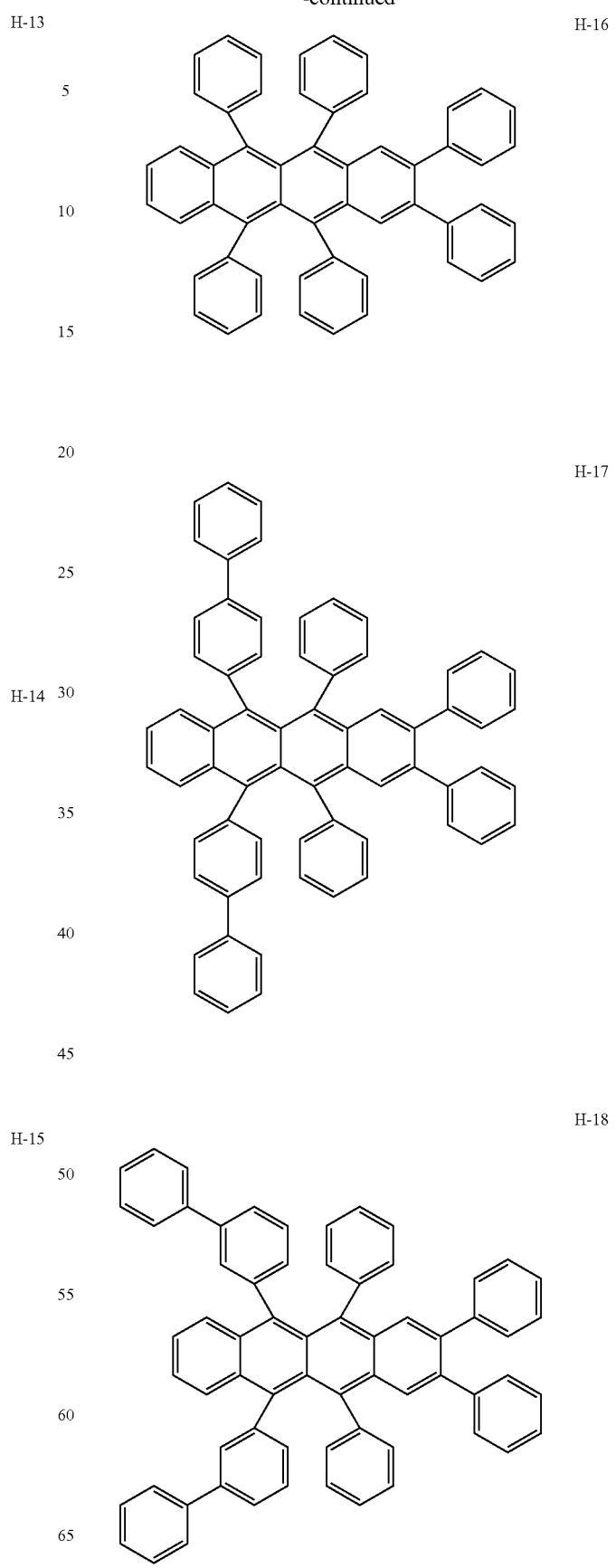

H-19
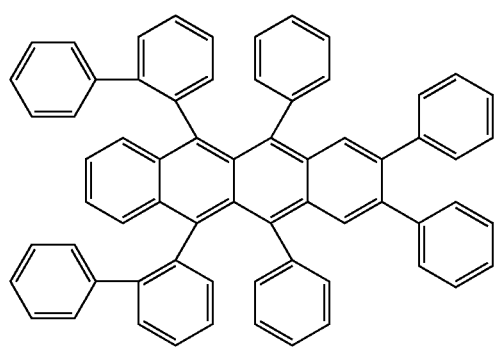
H-20
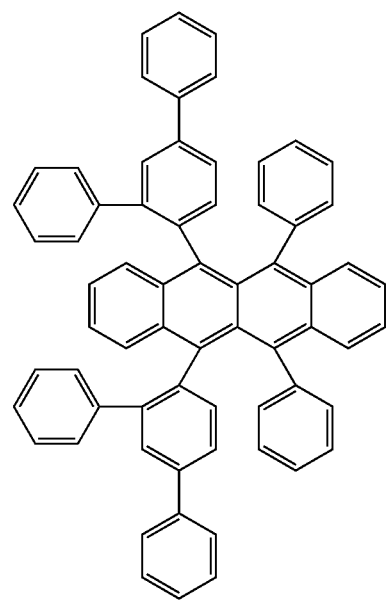
H-21
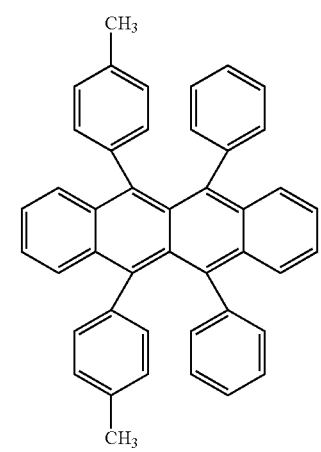
H-22
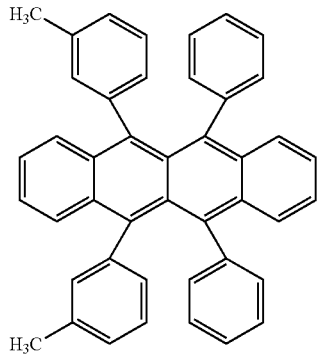
H-23
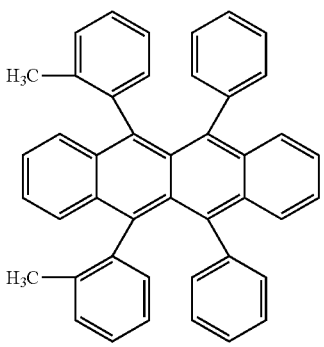
H-24
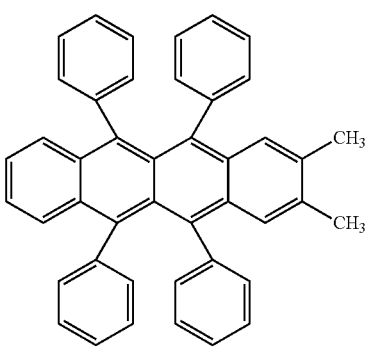
H-25
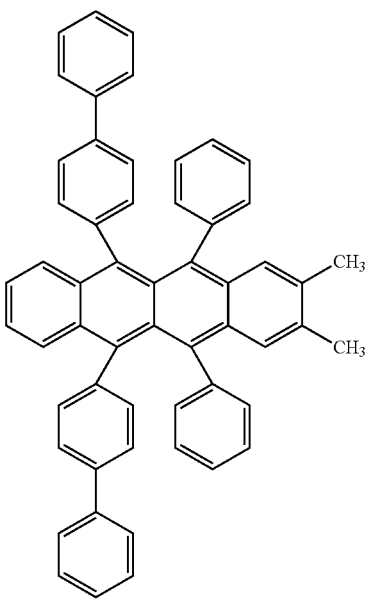

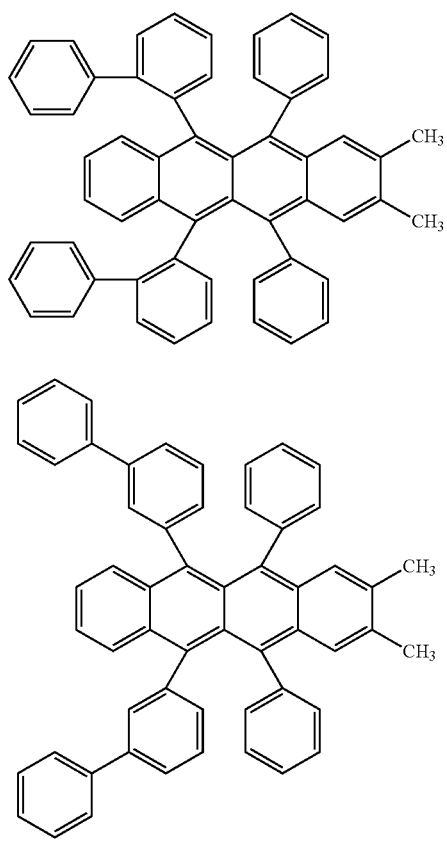

Further, the HOMO of the host material to be used in the light-emitting layer 5 is preferably 5.0 eV or more and 5.8 eV or less, and the LUMO of the constituent material of the hole injection layer 4 is preferably 2.5 eV or more and 3.6 eV or less.

(Electron Transport Layer)

The electron transport layer 6 has a function to transport electrons injected from the cathode 8 through the electron injection layer 7 to the light-emitting layer 5.

Examples of the constituent material (electron-transporting material) of the electron transport layer 6 include phenanthroline derivatives such as 2,9-dimethyl-4,7-diphenyl-1,10-phenanthroline (BCP), quinoline derivatives of organic metal complexes having 8-quinolinol or a derivative thereof as a ligand such as tris(8-quinolinolato)aluminum (Alq$_3$), azaindolizine derivatives, oxadiazole derivatives, perylene derivatives, pyridine derivatives, pyrimidine derivatives, quinoxaline derivatives, diphenylquinone derivatives, nitro-substituted fluorene derivatives, and acene-based materials such as anthracene-based materials, and among these, it is possible to use one type or two or more types in combination.

Among these, as the electron-transporting material to be used in the electron transport layer 6, it is preferred to use a compound having an anthracene skeleton. In addition, it is preferred to use a phenanthroline derivative or a nitrogen-containing compound including a nitrogen atom in the skeleton similarly to a phenanthroline derivative. In view of this, in particular, it is more preferred to use an azaindolizine-based compound having both of an azaindolizine skeleton and an anthracene skeleton in the molecule (hereinafter also simply referred to as "azaindolizine-based compound"). According to this, electrons can be efficiently transported and injected into the light-emitting layer 5. As a result, the luminous efficiency of the light-emitting element 1A can be increased.

Further, in the case where two or more materials among the electron-transporting materials as described above are used in combination, the electron transport layer 6 may be constituted by a mixed material in which two or more electron-transporting materials are mixed, or may be constituted by stacking a plurality of layers constituted by different electron-transporting materials. In this embodiment, as shown in FIG. 2, the electron transport layer 6 includes a first electron transport layer 6b and a second electron transport layer 6a provided between the first electron transport layer 6b and the light-emitting layer 5.

The compound having an anthracene skeleton to be used as the constituent material of the first electron transport layer 6b is preferably an azaindolizine-based compound having both of an azaindolizine skeleton and an anthracene skeleton in the molecule. Further, the compound having an anthracene skeleton to be used as the constituent material of the second electron transport layer 6a is preferably an anthracene-based compound having an anthracene skeleton in the molecule and also constituted by a carbon atom and a hydrogen atom. According to this, electrons can be efficiently transported and injected into the light-emitting layer 5, and also the deterioration of the electron transport layer 6 can be reduced. As a result, the luminous efficiency of the light-emitting element 1A can be increased, and also the life of the light-emitting element 1A can be extended.

Here, the life can be extended by decreasing the thickness of the first electron transport layer 6b while ensuring the thickness of the electron transport layer 6 necessary for extracting optical light by the second electron transport layer 6a.

In the azaindolizine-based compound to be used in the electron transport layer 6, the number of azaindolizine skeletons and the number of anthracene skeletons contained in one molecule are both preferably one or two. According to this, the electron transport property and the electron injection property of the electron transport layer 6 can be made excellent.

Specifically, as the azaindolizine-based compound to be used in the electron transport layer 6, it is preferred to use, for example, compounds represented by the following formulae ETL1-1 to ETL1-24, compounds represented by the following formulae ETL1-25 to ETL1-36, and compounds represented by the following formulae ETL1-37 to ETL1-56.

[Chem. 21]
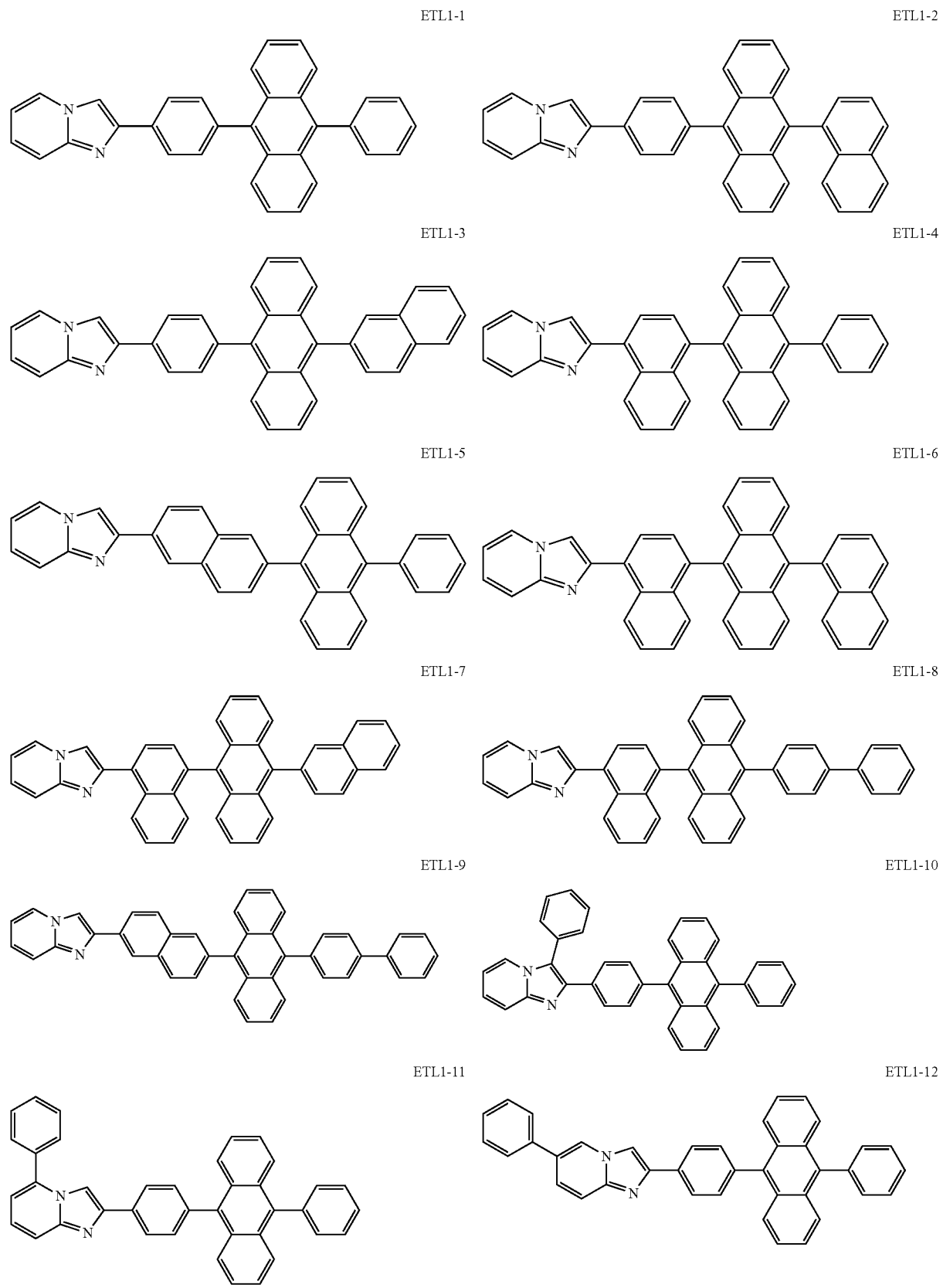

-continued
ETL1-13
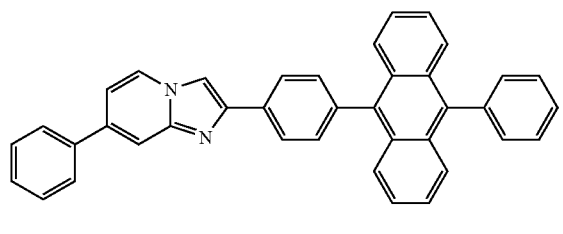
ETL1-14
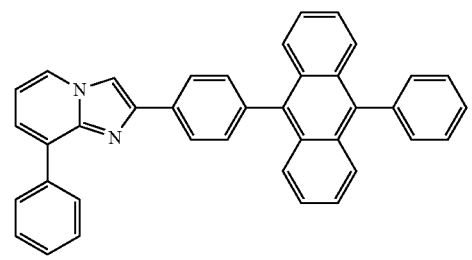
ETL1-15
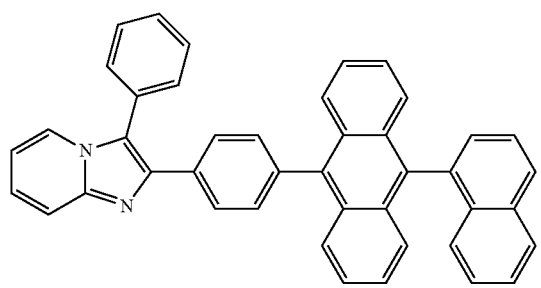
ETL1-16
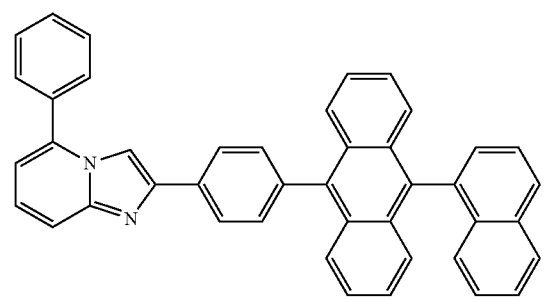
ETL1-17
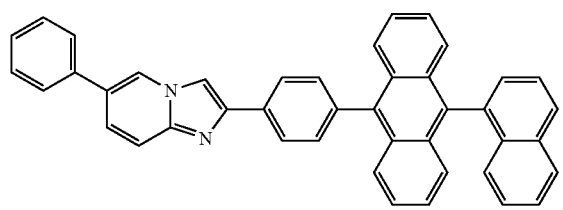
ETL1-18
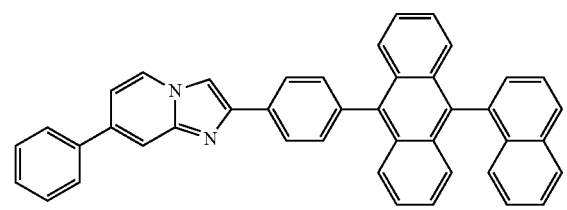
ETL1-19
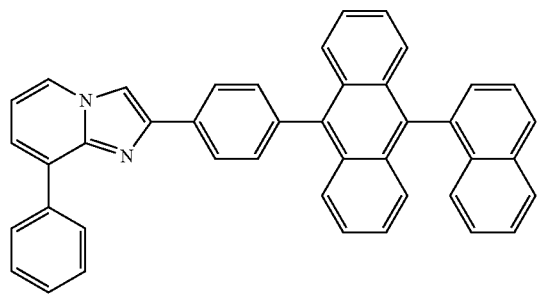
ETL1-20
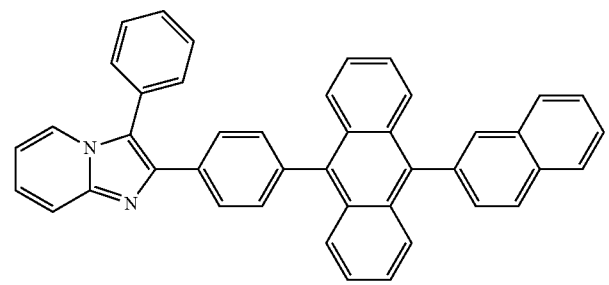
ETL1-21
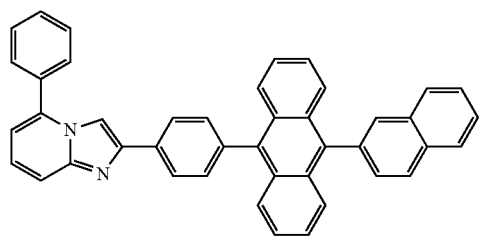
ETL1-22
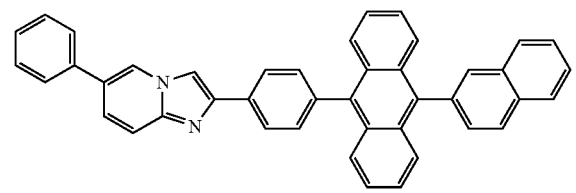

-continued
ETL1-23
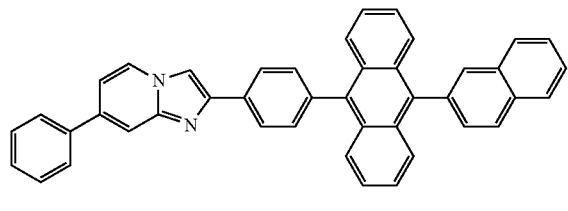
ETL1-24
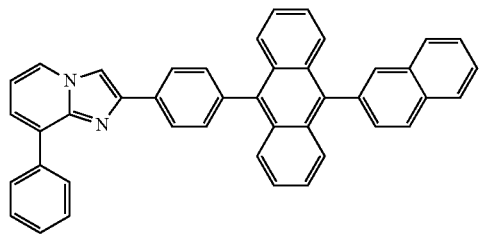
[Chem. 22]
ETL1-25
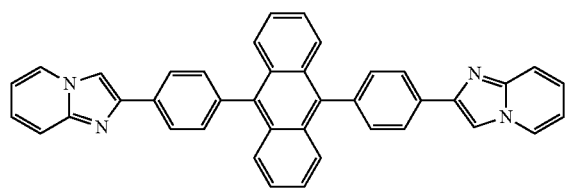
ETL1-26
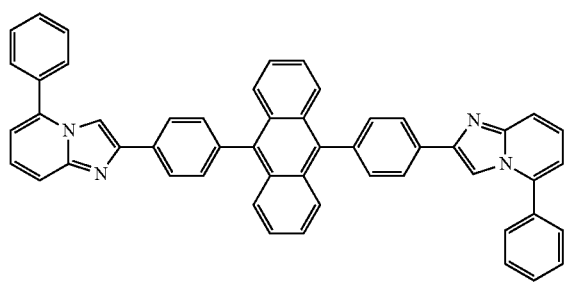
ETL1-27
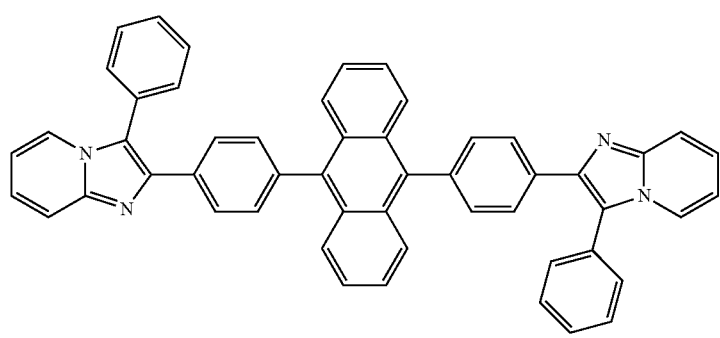
ETL1-28
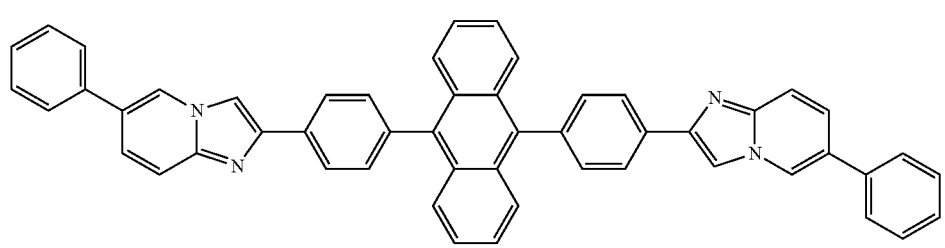
ETL1-29
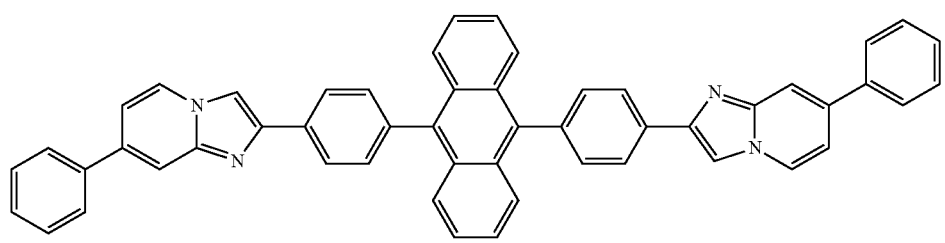

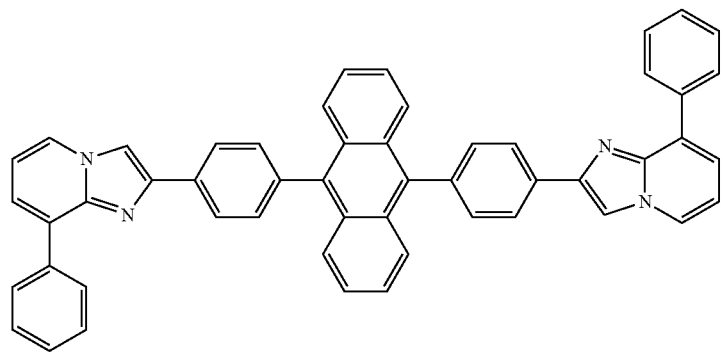
ETL1-30
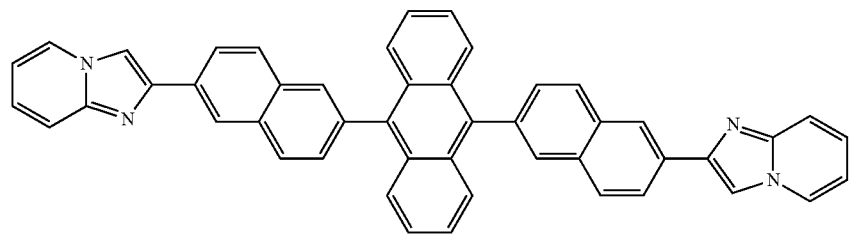
ETL1-31
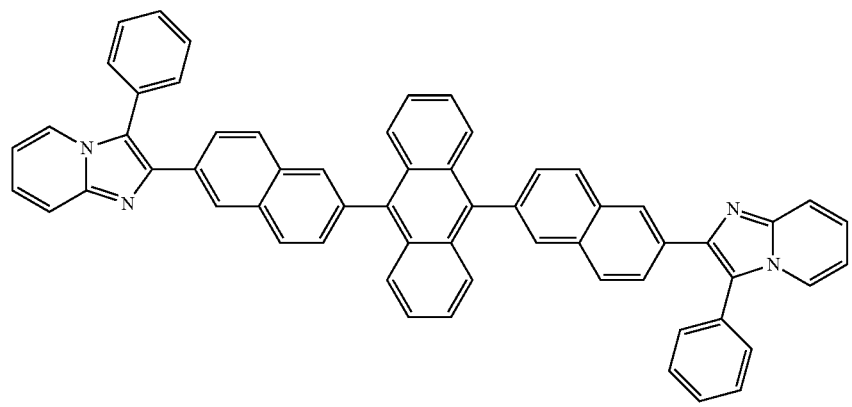
ETL1-32
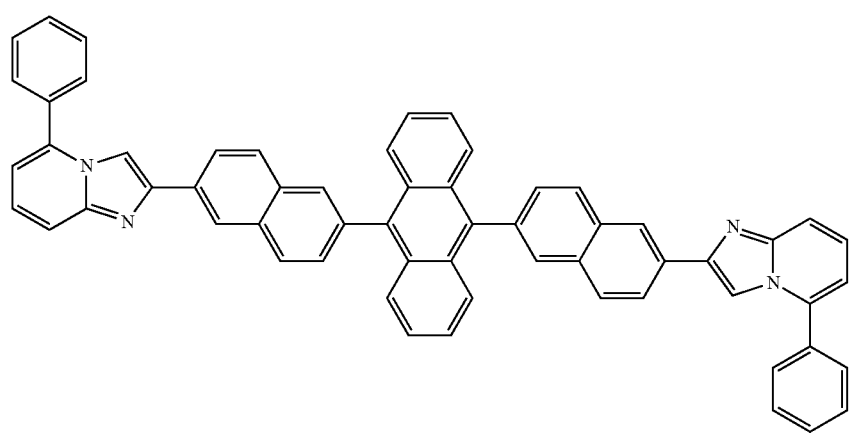
ETL1-33

ETL1-34
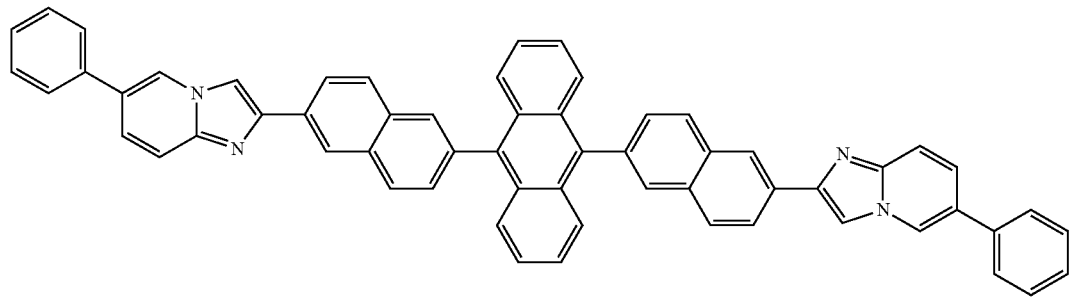
ETL1-35
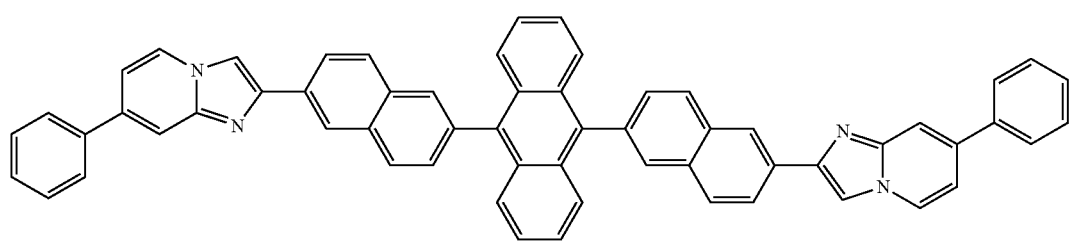
ETL1-36
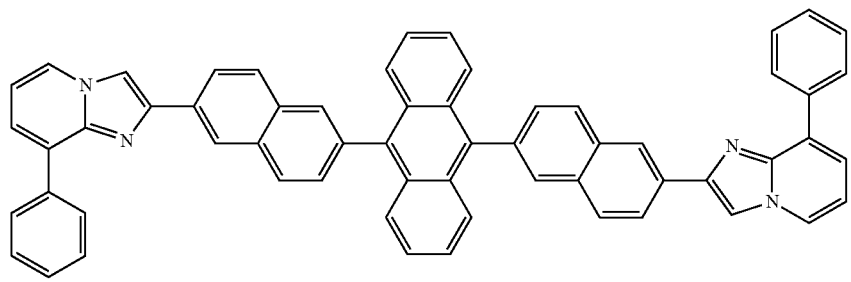
[Chem. 23]
ETL1-37     ETL1-38
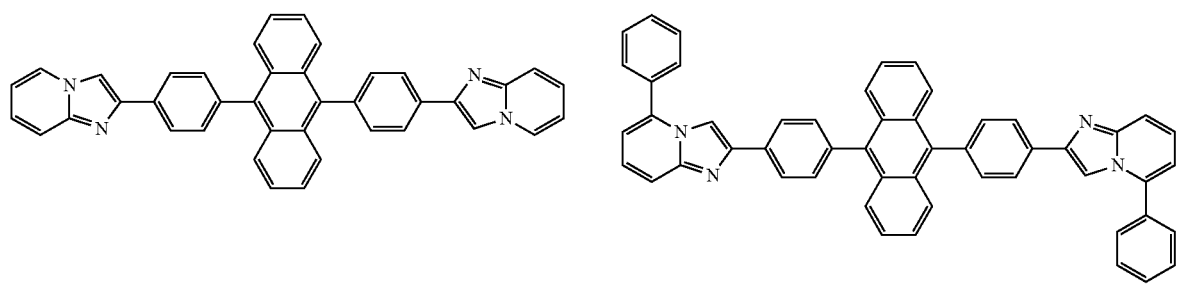
ETL1-39
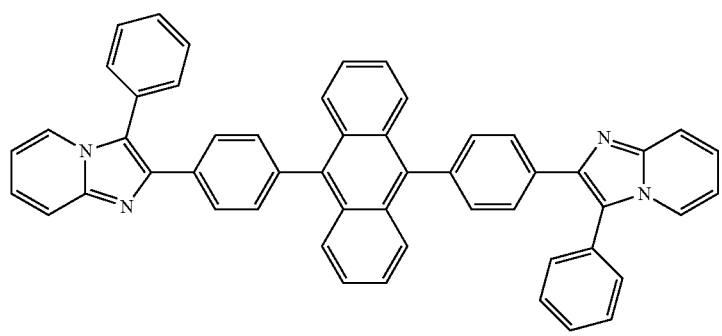

-continued
ETL1-40
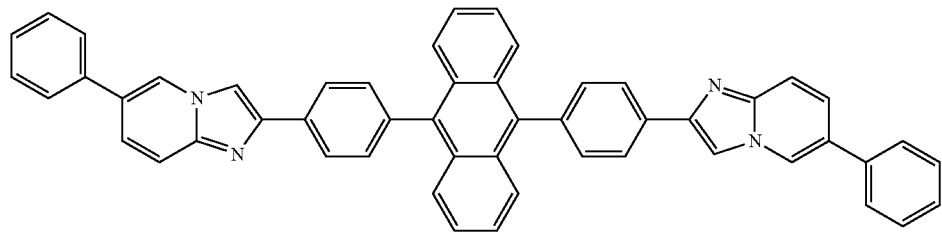
ETL1-41
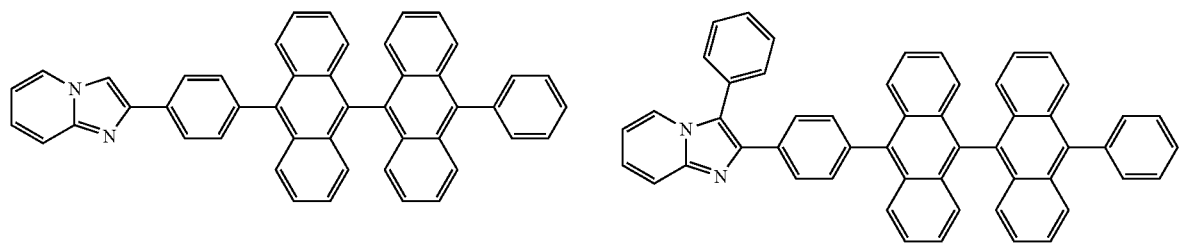
ETL1-42
ETL1-43
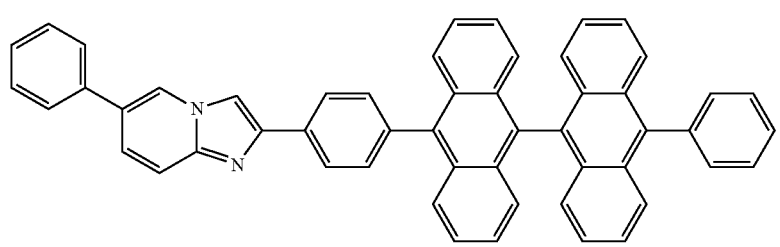
ETL1-44
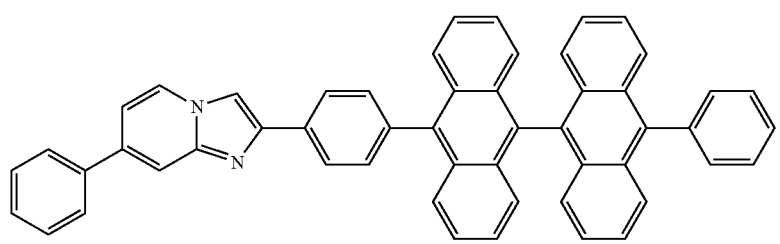
ETL1-45
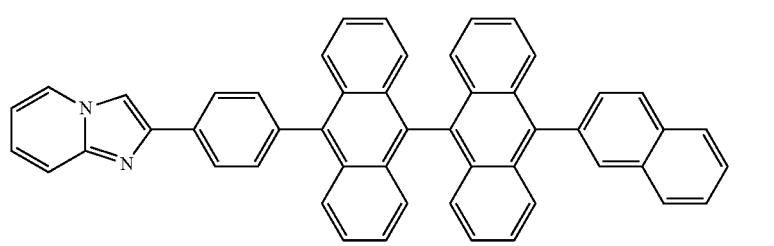
ETL1-46
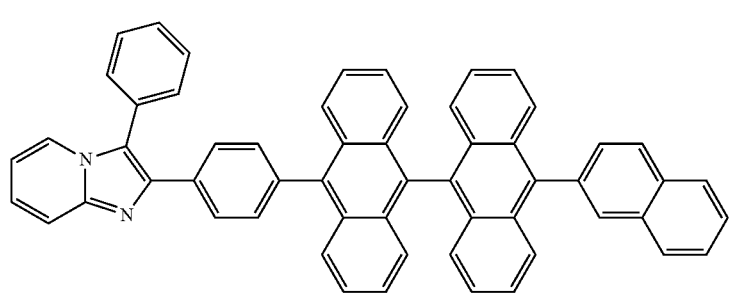

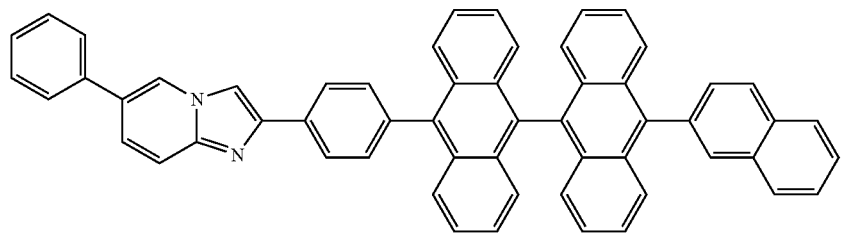
ETL1-47
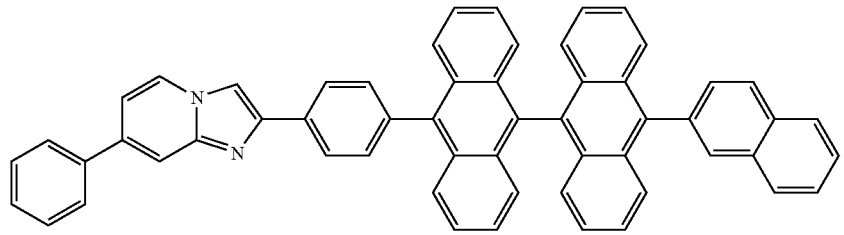
ETL1-48
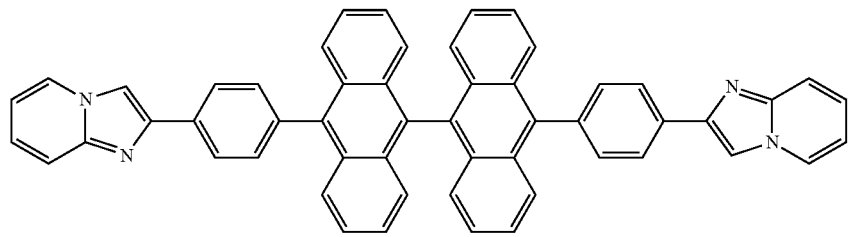
ETL1-49
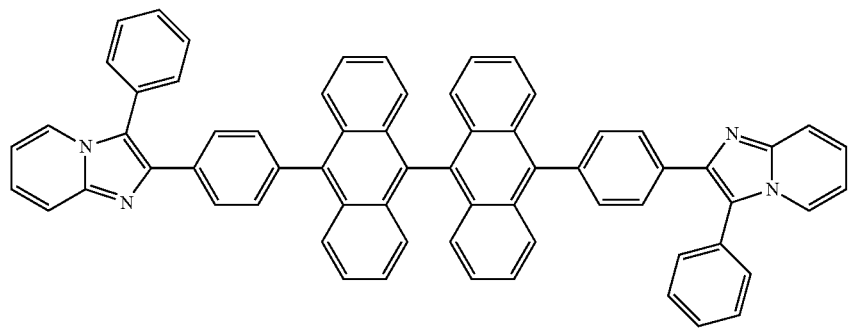
ETL1-50
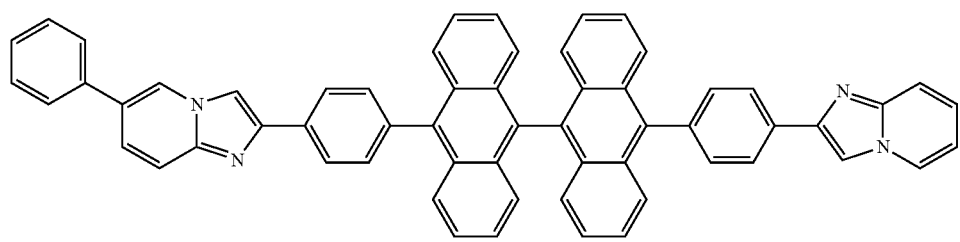
ETL1-51
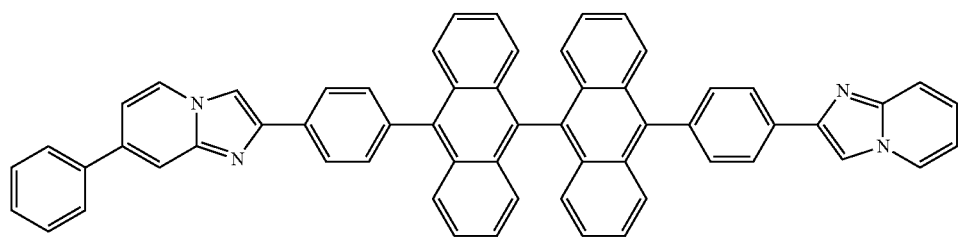
ETL1-52

-continued

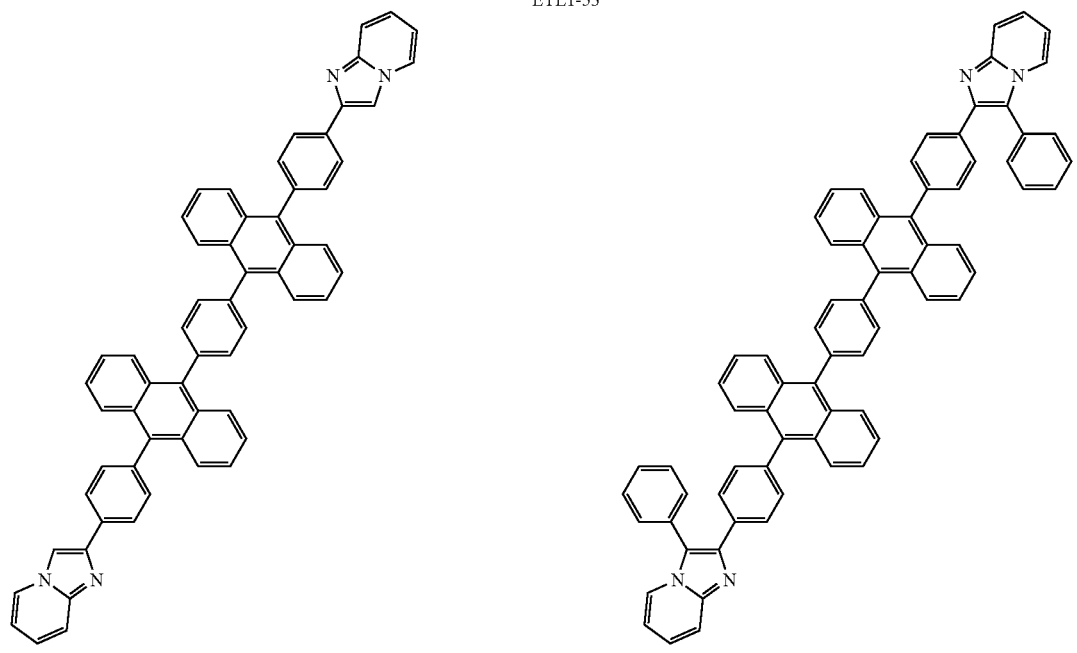

ETL1-53

ETL1-54

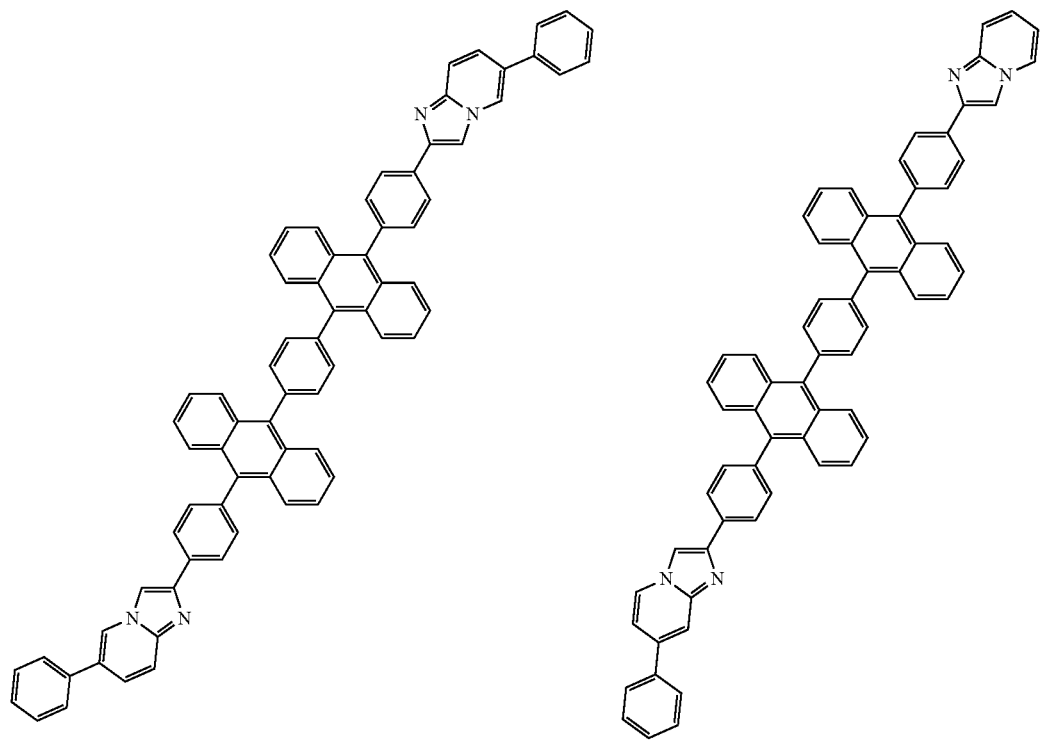

ETL1-55

ETL1-56

Such an azaindolizine-based compound has excellent electron transport property and electron injection property. Therefore, the luminous efficiency of the light-emitting element 1A can be improved.

The reason why such an azaindolizine-based compound has excellent electron transport property and electron injection property is considered to be as follows.

The entire molecule of the azaindolizine-based compound having an azaindolizine skeleton and an anthracene skeleton in the molecule as described above is connected by a Π-conjugated system, and therefore, the electron cloud is spread across the entire molecule.

Then, the portion of the azaindolizine skeleton of the azaindolizine-based compound has a function to receive an electron and a function to send the received electron to the portion of the anthracene skeleton. On the other hand, the portion of the anthracene skeleton of the azaindolizine-based compound has a function to receive an electron from the portion of the azaindolizine skeleton and a function to transfer the received electron to a layer adjacent to the electron transport layer 6 on the anode 3 side, that is, to the light-emitting layer 5.

To be more specific, the portion of the azaindolizine skeleton of the azaindolizine-based compound includes two nitrogen atoms, and one of the nitrogen atoms (on the side near the portion of the anthracene skeleton) has an $sp^2$ hybrid orbital, and the other nitrogen atom (on the side far from the portion of the anthracene skeleton) has an $sp^3$ hybrid orbital. The nitrogen atom with an $sp^2$ hybrid orbital forms a portion of the conjugated system of the azaindolizine-based compound molecule and also has higher electronegativity than a carbon atom, and thus more strongly attracts an electron, and therefore functions as a portion that receives an electron. On the other hand, the nitrogen atom with an $sp^3$ hybrid orbital is not a normal conjugated system but has a non-covalent electron pair, and therefore, the electron of the nitrogen atom functions as a portion that sends an electron toward the conjugated system of the azaindolizine-based compound molecule.

On the other hand, the portion of the anthracene skeleton of the azaindolizine-based compound is electrically neutral, and therefore can easily receive an electron from the portion of the azaindolizine skeleton. Further, the portion of the anthracene skeleton of the azaindolizine-based compound has a large orbital overlap with the constituent material of the light-emitting layer 5, particularly, the host material (tetracene-based material) thereof, and therefore can easily transfer an electron to the host material of the light-emitting layer 5.

Further, such an azaindolizine-based compound has excellent electron transport property and electron injection property as described above, and therefore as a result, the driving voltage of the light-emitting element 1A can be decreased.

Further, the portion of the azaindolizine skeleton is stable even if the nitrogen atom with an $sp^2$ hybrid orbital is reduced and also is stable even if the nitrogen atom with an spa hybrid orbital is oxidized. Due to this, such an azaindolizine-based compound has high stability against electrons and holes. As a result, the life of the light-emitting element 1A can be extended.

Further, the anthracene-based compound to be used in the electron transport layer 6 (particularly in the second electron transport layer 6a in the case where the electron transport layer 6 includes the second electron transport layer 6a) may be any as long as it is a compound represented by the following formula ETL2, but is preferably a compound represented by the following formula ETL2-A, the following formula ETL2-B, the following formula ETL2-C, or the following formula ETL2-D, and more specifically, it is preferably, for example, a compound represented by any of the following formulae ETL2-1 to ETL2-56.

[Chem. 24]

ETL2 (general formula)

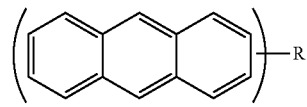

R: a hydrogen atom
an alkyl group
aryl which may have a substituent
arylamine

ETL2-A

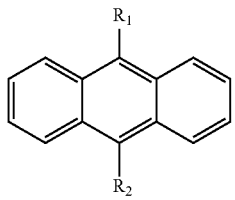

R1 and R2 may be the same or different;
a hydrogen atom
an alkyl group
aryl which may have a substituent
arylamine

ETL2-B

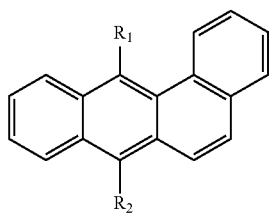

R1 and R2 may be the same or different;
a hydrogen atom
an alkyl group
aryl which may have a substituent
arylamine

ETL2-C

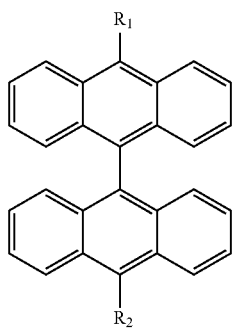

R1 and R2 may be the same or different;
a hydrogen atom
an alkyl group
aryl which may have a substituent
arylamine ETL2-D
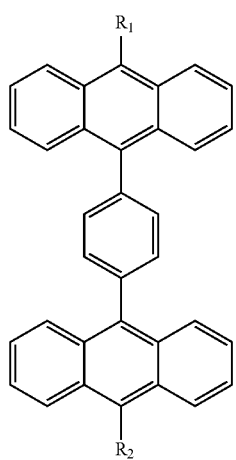
R1 and R2 may be the same or different;
a hydrogen atom
an alkyl group
aryl which may have a substituent
arylamine
[Chem. 25]
ETL2-1
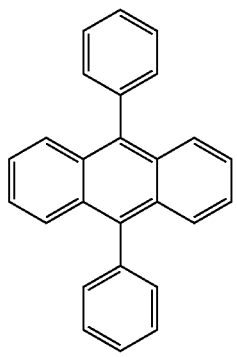
ETL2-2
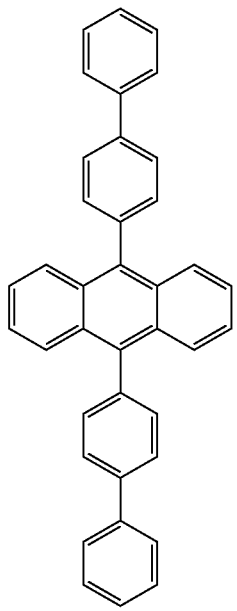
ETL2-3
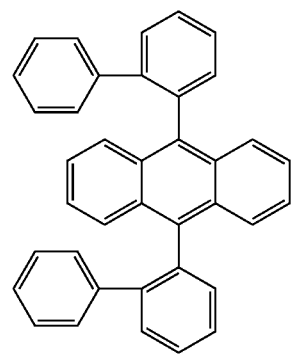
ETL2-4
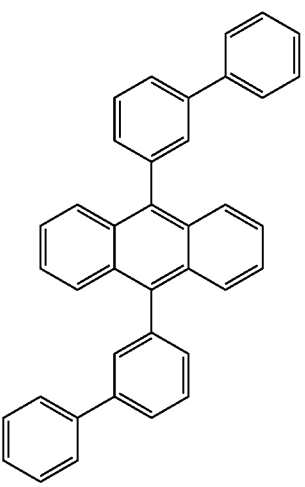
ETL2-5
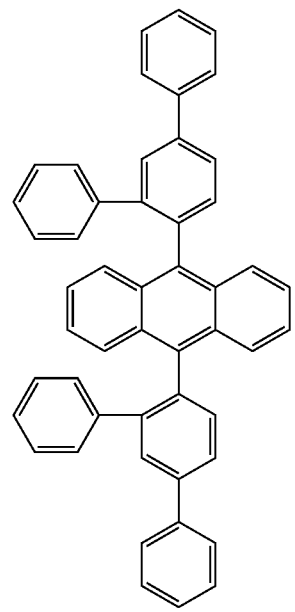

ETL2-6
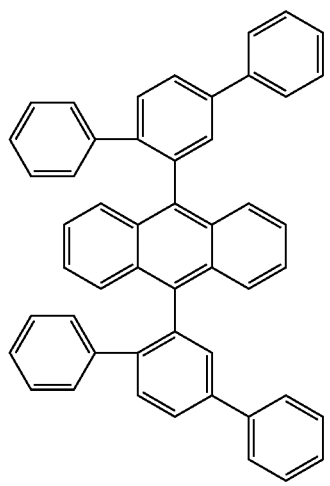
ETL2-7
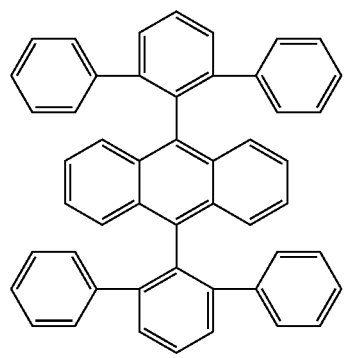
ETL2-8
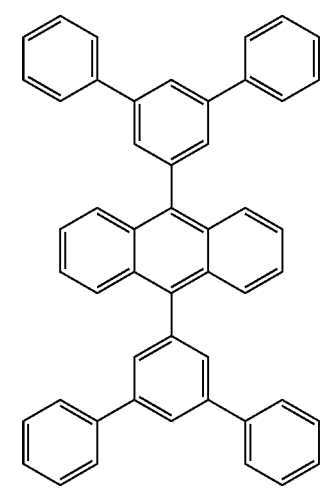
ETL2-9
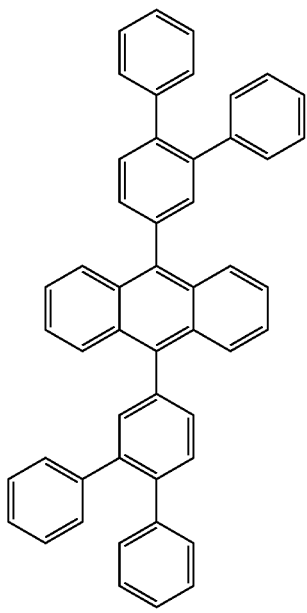
ETL2-10
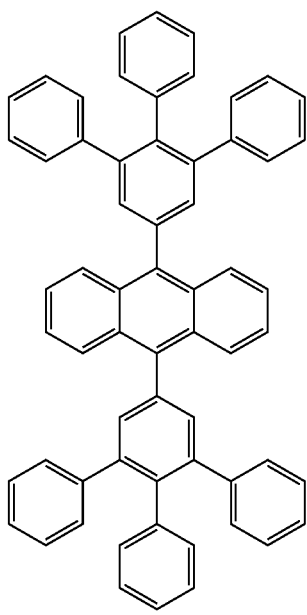

ETL2-11
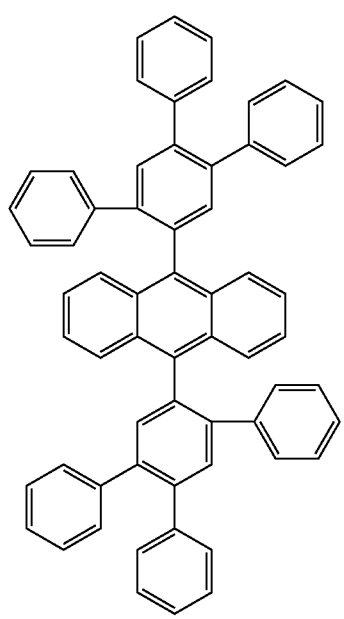
ETL2-12
ETL2-13
ETL2-14
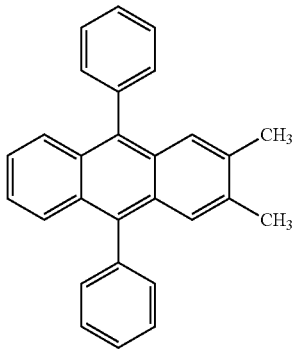
ETL2-15
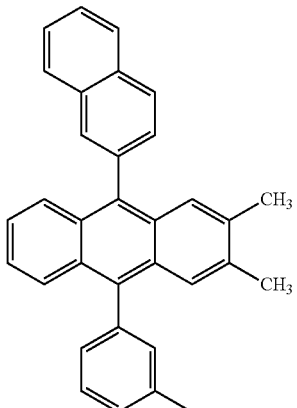
ETL2-16
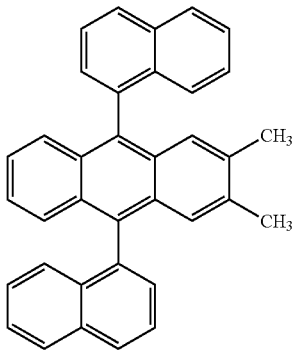
[Chem. 26]
ETL2-17
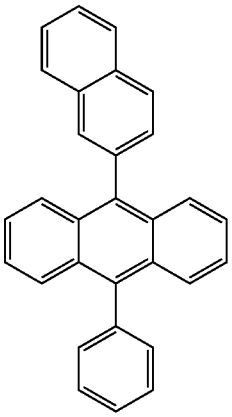

ETL2-18
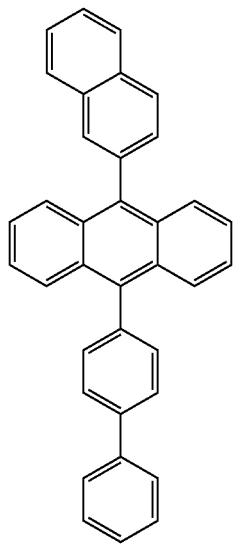
ETL2-19
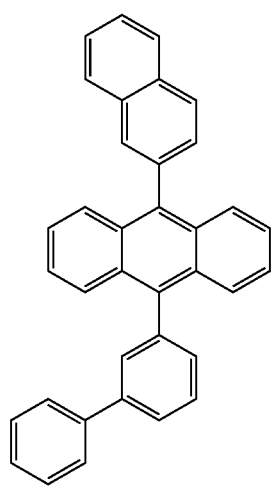
ETL2-20
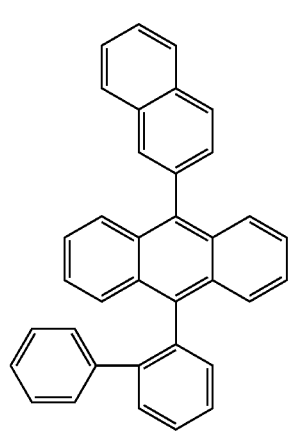
ETL2-21
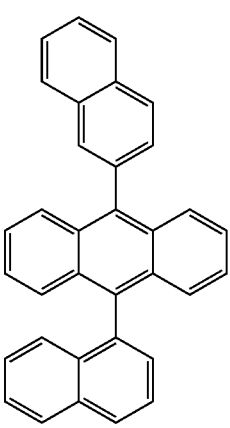
ETL2-22
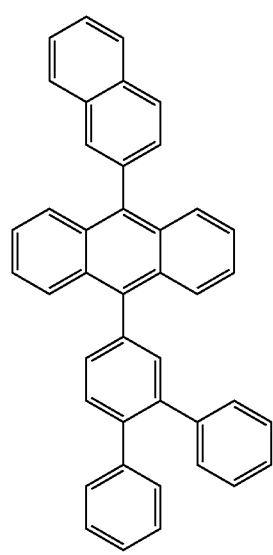
ETL2-23
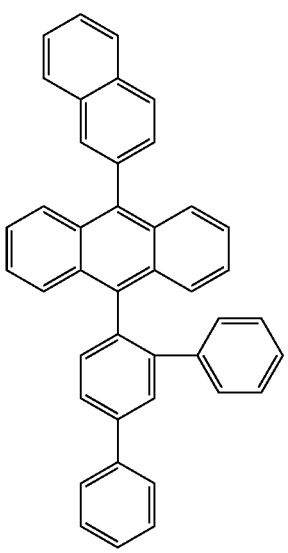

ETL2-24
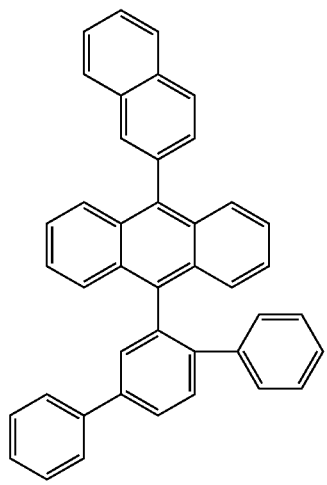
ETL2-25
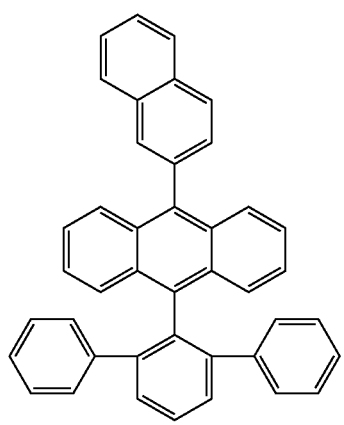
ETL2-26
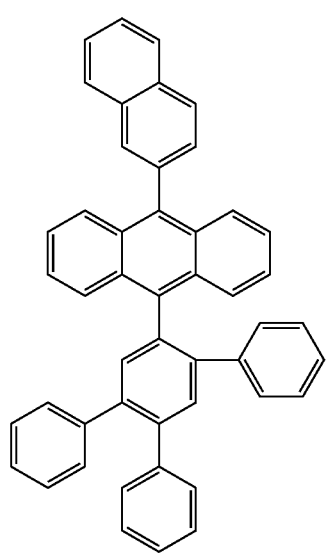
ETL2-27
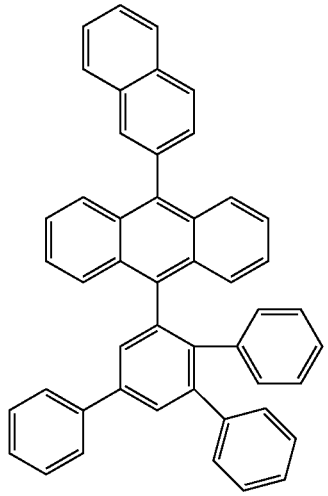
ETL2-28
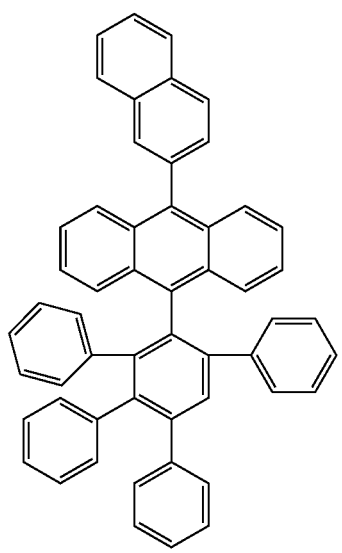
ETL2-29
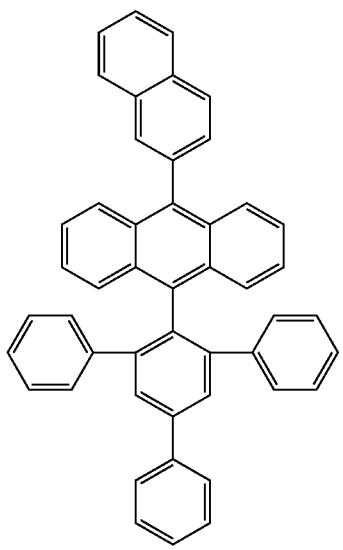

-continued
ETL2-30
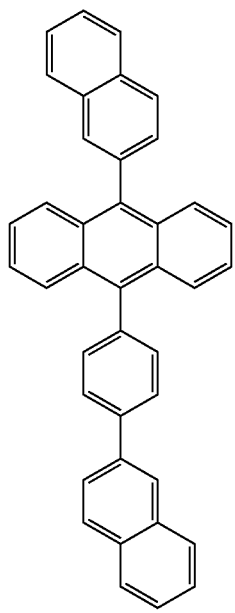
ETL2-31
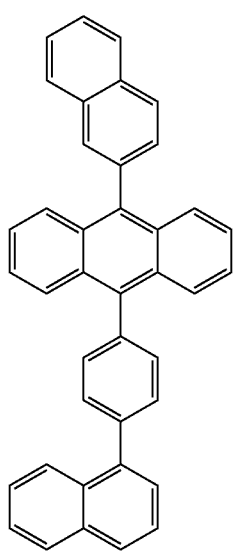
-continued
ETL2-32
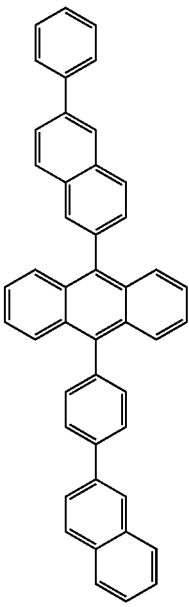
ETL2-33
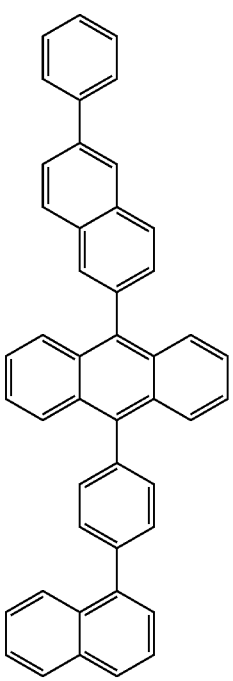

ETL2-34
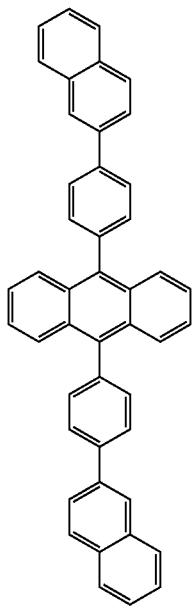
ETL2-35
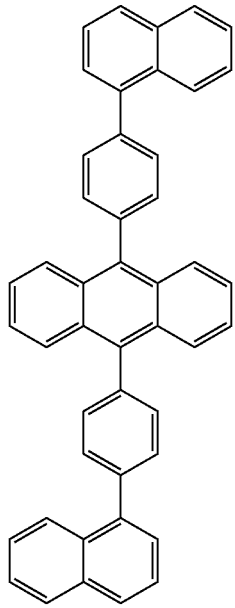
ETL2-36
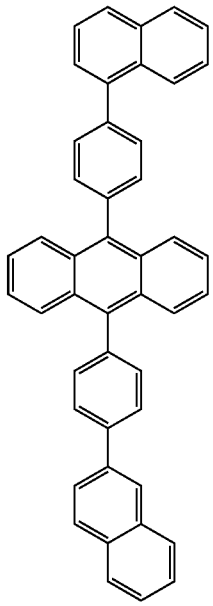
[Chem. 27]
ETL2-37
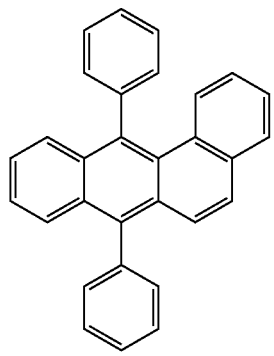
ETL2-38
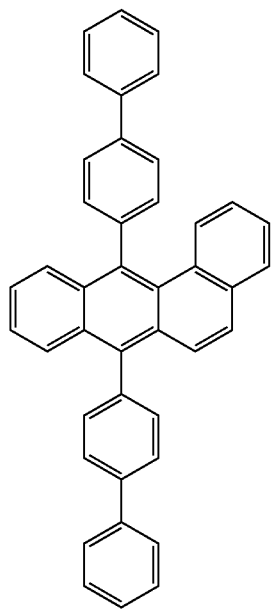

ETL2-39
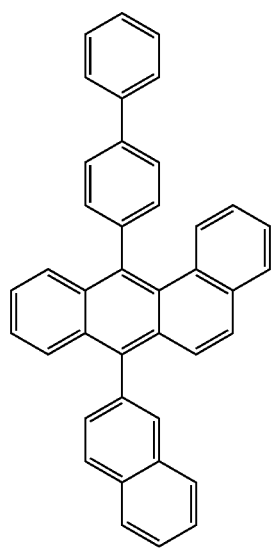
ETL2-40
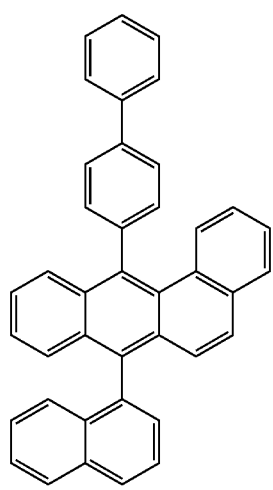
ETL2-41
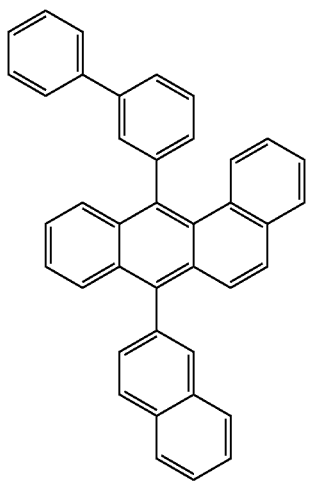
ETL2-42
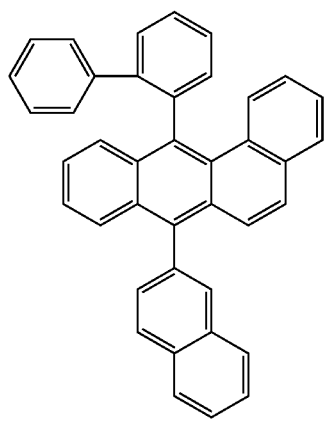
ETL2-43
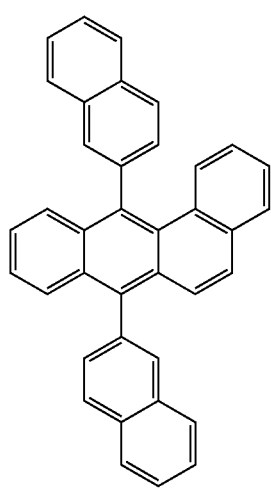
ETL2-44
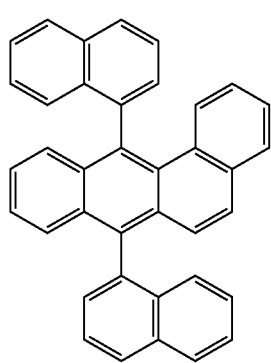

ETL2-45
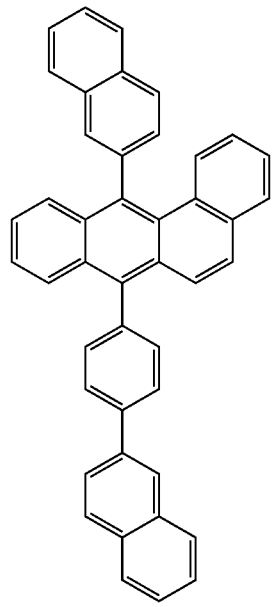
ETL2-47
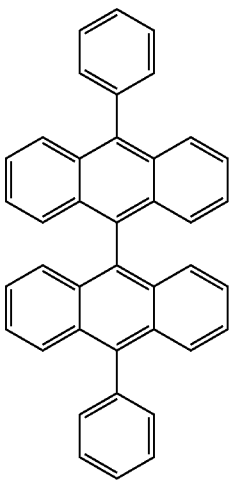
ETL2-46
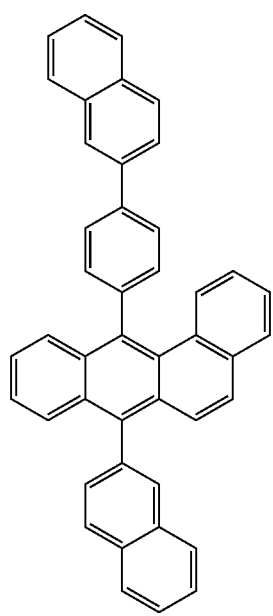
ETL2-48
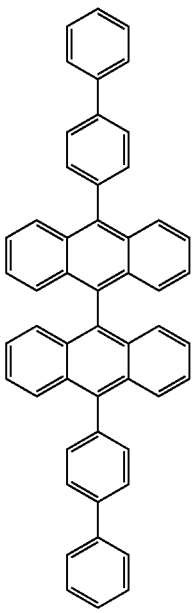

ETL2-49
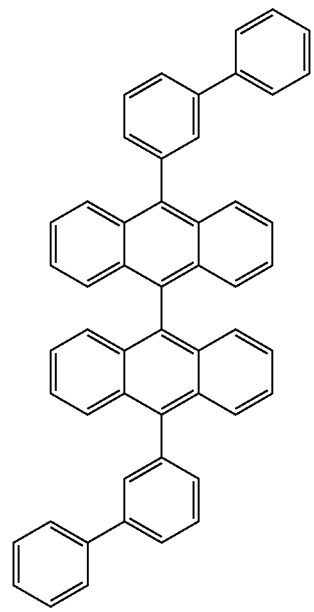
ETL2-50
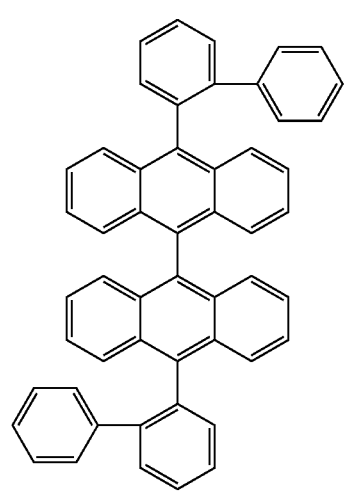
ETL2-51
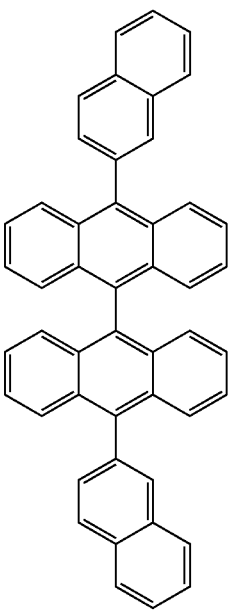
ETL2-52
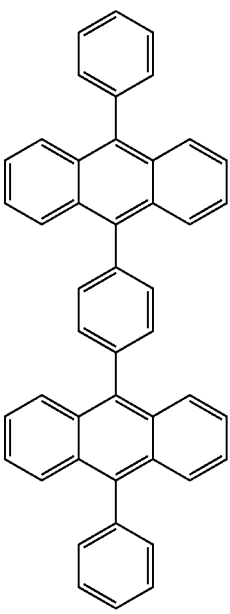

ETL2-53

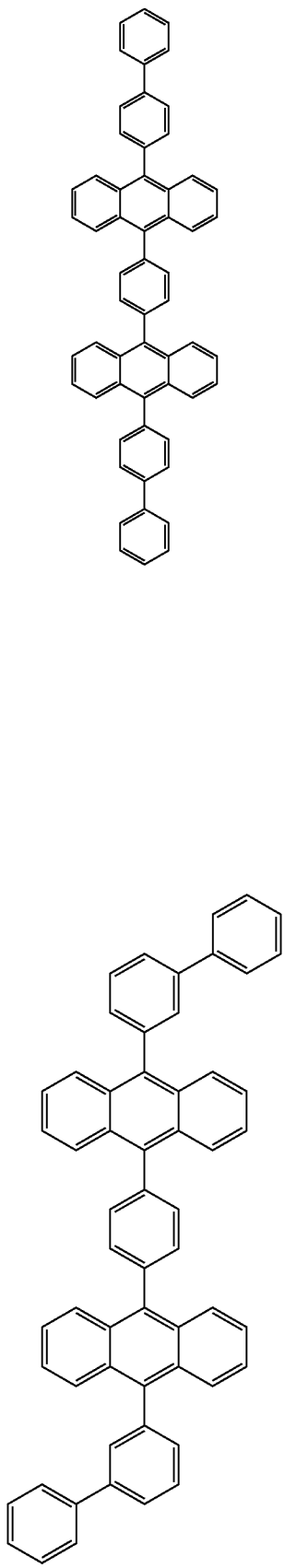

ETL2-54

ETL2-55

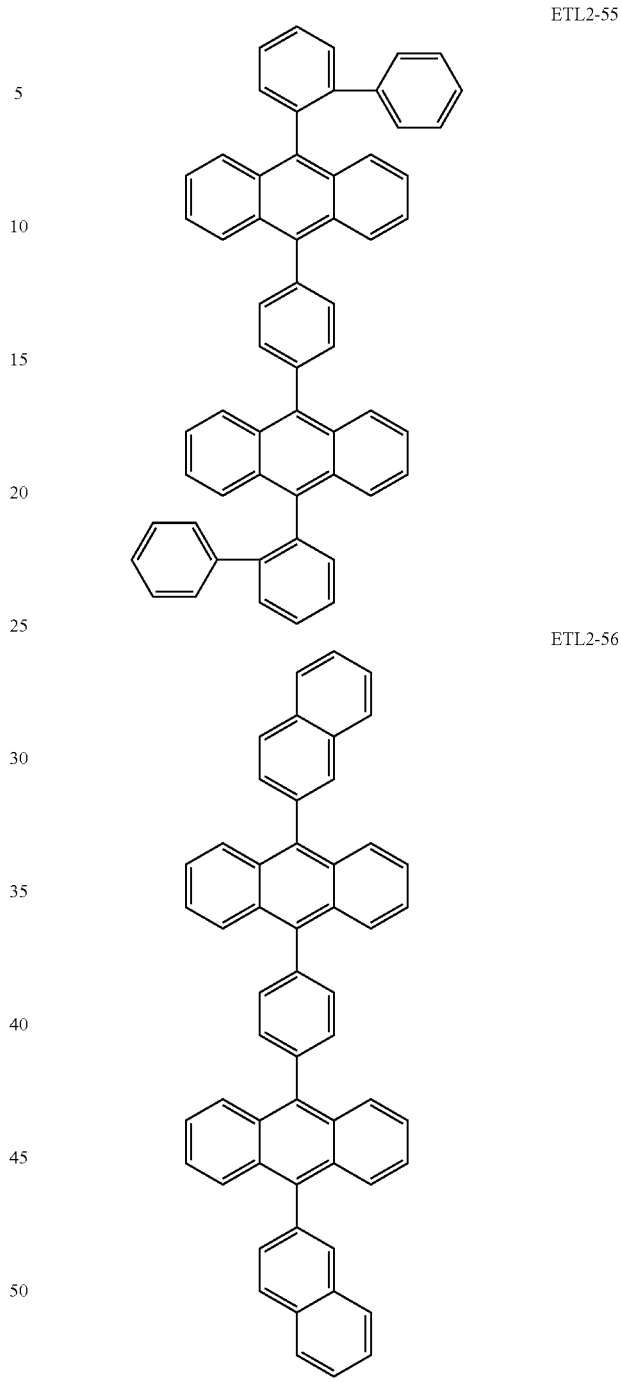

ETL2-56

Further, a difference between the HOMO of the constituent material of the electron transport layer 6 (more specifically, the second electron transport layer 6a) and the HOMO of the host material to be used in the light-emitting layer 5 is preferably 0.2 eV or more. According to this, holes can be prevented from coming out from the light-emitting layer 5 to the electron transport layer 6, and thus, the luminous efficiency can be increased.

Further, the HOMO of the constituent material of the second electron transport layer 6a is preferably 5.5 eV or more and 6.0 eV or less, and the LUMO of the constituent material of the second electron transport layer 6a is preferably 2.5 eV or more and 3.0 eV or less.

Further, the HOMO of the constituent material of the first electron transport layer 6b is preferably 5.8 eV or more and 6.5 eV or less, and the LUMO of the constituent material of the first electron transport layer 6b is preferably 2.8 eV or more and 3.5 eV or less.

Further, the thickness of the second electron transport layer 6a is preferably thicker than the thickness of the first electron transport layer 6b. According to this, while suppressing the driving voltage of the light-emitting element 1A, electrons can be efficiently transported and injected into the light-emitting layer 5, and also the deterioration of the electron transport layer 6 can be reduced.

Further, a specific thickness of the second electron transport layer 6a is preferably 30 nm or more and 150 nm or less, more preferably 70 nm or more and 90 nm or less. According to this, while suppressing the driving voltage of the light-emitting element 1A, electrons can be efficiently transported and injected into the light-emitting layer 5, and also the deterioration of the electron transport layer 6 can be reduced.

Incidentally, the second electron transport layer 6a may be omitted depending on the combination of the constituent materials of the first electron transport layer 6b and the light-emitting layer 5 or the like.

(Electron Injection Layer)

The electron injection layer 7 has a function to improve the efficiency of electron injection from the cathode 8.

Examples of the constituent material (electron-injecting material) of the electron injection layer 7 include various types of inorganic insulating materials and various types of inorganic semiconductor materials.

Examples of such an inorganic insulating material include alkali metal chalcogenides (oxides, sulfides, selenides, and tellurides), alkaline earth metal chalcogenides, alkali metal halides, and alkaline earth metal halides, and among these, it is possible to use one type or two or more types in combination. By constituting the electron injection layer 7 by such a material as a main material, the electron injection property can be further improved. In particular, an alkali metal compound (such as an alkali metal chalcogenide or an alkali metal halide) has a very small work function, and by constituting the electron injection layer 7 by using the compound, the light-emitting element 1A has high luminance.

Examples of the alkali metal chalcogenide include $Li_2O$, LiO, $Na_2S$, $Na_2Se$, and NaO.

Examples of the alkaline earth metal chalcogenide include CaO, BaO, SrO, BeO, BaS, MgO, and CaSe.

Examples of the alkali metal halide include CsF, LiF, NaF, KF, LiCl, KCl, and NaCl.

Examples of the alkaline earth metal halide include $CaF_2$, $BaF_2$, $SrF_2$, $MgF_2$, and $BeF_2$.

Further, examples of the inorganic semiconductor material include oxides, nitrides, and oxynitrides containing at least one element selected from Li, Na, Ba, Ca, Sr, Yb, Al, Ga, In, Cd, Mg, Si, Ta, Sb, and Zn, and among these, it is possible to use one type or two or more types in combination.

The average thickness of the electron injection layer 7 is not particularly limited, but is preferably from about 0.1 to 1000 nm, more preferably from about 0.2 to 100 nm, further more preferably from about 0.2 to 50 nm.

Incidentally, the electron injection layer 7 may be omitted depending on the constituent material, thickness, or the like of the cathode 8 and the electron transport layer 6.

According to the light-emitting element 1A configured as described above, light emission in a near-infrared region can be achieved.

(Method for Producing Light-Emitting Device)

The light-emitting device 100 as described above can be produced, for example, as follows.

[1] First, a substrate 21 is prepared, and a plurality of driving transistors 24 are formed so as to correspond to light-emitting elements 1A to be formed, and thereafter, a planarization layer 22 is formed so as to cover these transistors 24.

[1-A] First, a substrate 21 is prepared, and on the substrate 21, driving TFTs 24 are formed.

[1-Aa] First, on the substrate 21, a semiconductor film which has an average thickness of about 30 to 70 nm and is composed of amorphous silicon as a main material is formed by, for example, a plasma CVD method or the like.

[1-Ab] Subsequently, the semiconductor film is subjected to a crystallization treatment by a laser annealing method, a solid-phase growth method, or the like, whereby amorphous silicon is converted to polysilicon.

Here, in the laser annealing method, for example, a line beam which is an excimer laser and has a length of 400 mm is used, and the output intensity thereof is set to, for example, about 200 $mJ/cm^2$.

[1-Ac] Subsequently, by patterning the semiconductor film into island shapes, whereby semiconductor layers 241 are obtained. Then, a gate insulating layer 242 which has an average thickness of about 60 to 150 nm and is composed of silicon oxide, silicon nitride, or the like as a main material is formed so as to cover these island-shaped semiconductor layers 241 by a plasma CVD method or the like using, for example, TEOS (tetraethoxysilane), oxygen gas, or the like as a raw material gas.

[1-Ad] Subsequently, on the gate insulating layer 242, for example, by a sputtering method or the like, a conductive film composed of a metal such as aluminum, tantalum, molybdenum, titanium, or tungsten as a main material is formed, followed by patterning, whereby a gate electrode 243 is formed.

[1-Ae] Subsequently, by doping phosphorus ions at a high concentration in this state, source and drain regions are formed in a self-aligned manner on the gate electrode 243. Incidentally, a portion where the impurity is not introduced becomes a channel region.

[1-B] Subsequently, a source electrode 244 and a drain electrode 245 to be electrically connected to the driving TFT 24 are formed.

[1-Ba] First, a first planarization layer is formed so as to cover the gate electrode 243, and then, a contact hole is formed.

[1-Bb] Subsequently, in the contact hole, a source electrode 244 and a drain electrode 245 are formed.

[1-C] Subsequently, a wiring (relay electrode) 27 for electrically connecting the drain electrode 245 to the anode 3 is formed.

[1-Ca] First, a second planarization layer is formed on the first planarization layer, and then, a contact hole is formed.

[1-Cb] Subsequently, a wiring 27 is formed in the contact hole.

Incidentally, a planarization layer 22 is constituted by the first planarization layer and the second planarization layer formed in the step [1-B] and the step [1-C].

[2] Subsequently, on the planarization layer 22, a reflective film 32, a corrosion preventive film 33, and the anode (individual electrode) 3 are formed so as to correspond to each wiring 27 and stacked in this order.

The reflective film 32 can be obtained by, for example, forming a thin film composed of a constituent material of the reflective film 32 as a main material on the planarization layer 22 by a gas phase deposition method such as a vacuum vapor deposition method or a sputtering method, or the like, followed by patterning.

Further, the corrosion preventive film 33 can be obtained by forming a thin film composed of a constituent material of the corrosion preventive film 33 as a main material on the planarization layer 22 so as to cover the reflective film 32 in the same manner as described above, followed by patterning.

In addition, the anode 3 can be obtained by forming a thin film composed of a constituent material of the anode 3 as a main material on the planarization layer 22 so as to cover the reflective film 32 and the corrosion preventive film 33 in the same manner as described above, followed by patterning.

[3] Subsequently, on the planarization layer 22, a partition wall (bank) 31 is formed so as to divide each anode 3, that is, so as to divide a region in which each light-emitting element 1A is formed.

The partition wall 31 can be formed by forming an insulating film on the planarization layer 22 so as to cover the reflective film 32, the corrosion preventive film 33, and the anode 3, followed by patterning or the like using photolithography or the like so as to expose the anode 3.

Here, the constituent material of the partition wall 31 is selected in consideration of heat resistance, liquid repellency, ink solvent resistance, adhesion to the planarization layer 22 or the like, and so on.

Specific examples of the constituent material of the partition wall 31 include organic materials such as an acrylic resin and a polyimide-based resin and inorganic materials such as $SiO_2$.

Further, the shape of the opening of the partition wall 31 may be any, for example, a circle, an ellipse, a polygon such as a hexagon, or the like other than a tetragon as shown in FIG. 1.

The height of such a partition wall 31 is not particularly limited, but is preferably set to about 30 to 500 nm. By setting the height within such a range, the function as the partition wall (bank) is sufficiently exhibited.

[4] Subsequently, a hole injection layer 4 is formed so as to overlap with the anode 3 and the partition wall 31, that is, so as to cover the entire surface of the partition wall 31 on the opposite side of the anode 3.

By doing this, the hole injection layer 4 which is common to the respective light-emitting elements 1A is formed collectively (integrally).

The hole injection layer 4 is preferably formed by, for example, a gas-phase process using a dry plating method such as a CVD method, vacuum vapor deposition, or sputtering, or the like.

Incidentally, the hole injection layer 4 can also be formed by, for example, supplying a hole injection layer-forming material prepared by dissolving a hole-injecting material in a solvent or dispersing a hole-injecting material in a dispersion medium onto the anode 3 and the partition wall 31, followed by drying (removal of the solvent or removal of the dispersion medium).

As the method for supplying the hole injection layer-forming material, for example, any of various coating methods such as a spin coating method, a roll coating method, and an ink jet printing method can also be used. The hole injection layer 4 can be relatively easily formed by using such a coating method.

Examples of the solvent or the dispersion medium to be used in the preparation of the hole injection layer-forming material include various types of inorganic solvents, various types of organic solvents, and mixed solvents containing any of these solvents.

Incidentally, the drying can be performed by, for example, leaving the material to stand in an atmosphere at atmospheric pressure or reduced pressure, by a heating treatment, by spraying an inert gas, or the like.

Further, prior to this step, the upper surface of the anode 3 may be subjected to an oxygen plasma treatment. According to this, lyophilicity can be imparted to the upper surface of the anode 3, an organic substance adhered to the upper surface of the anode 3 can be removed (washed off), the work function in the vicinity of the upper surface of the anode 3 can be adjusted, and so on.

Here, the conditions for the oxygen plasma treatment are preferably, for example, as follows: the plasma power is from about 100 to 800 W, the oxygen gas flow rate is from about 50 to 100 mL/min, the speed of conveying a member to be treated (anode 3) is from about 0.5 to 10 mm/sec, and the temperature of the substrate 21 is from about 70 to 90° C.

[5] Subsequently, a light-emitting layer 5 is formed so as to cover the entire surface of the hole injection layer 4. By doing this, the light-emitting layer 5 which is common to the respective light-emitting elements 1A is formed collectively.

[6] Subsequently, an electron transport layer 6 (a first electron transport layer 6b and a second electron transport layer 6a) is formed so as to cover the entire surface of the light-emitting layer 5. By doing this, the electron transport layer 6 (the first electron transport layer 6b and the second electron transport layer 6a) which is common to the respective light-emitting elements 1A is formed collectively.

[7] Subsequently, an electron injection layer 7 is formed so as to cover the entire surface of the electron transport layer 6. By doing this, the electron injection layer 7 which is common to the respective light-emitting elements 1A is formed collectively.

[8] Subsequently, a cathode 8 is formed so as to cover the entire surface of the electron injection layer 7. By doing this, the cathode 8 which is common to the respective light-emitting elements 1A is formed collectively.

[9] Subsequently, a cathode cover 34 is formed so as to cover the entire surface of the cathode 8. By doing this, the cathode cover 34 which is common to the respective light-emitting elements 1A is formed collectively.

Incidentally, the respective layers to be formed in the above steps [5] to [9] can also be formed by a gas-phase process described when forming the hole injection layer 4 in the above step [4] or a liquid-phase process, however, above all, it is preferred to use a gas-phase process. By using a gas-phase process, a layer to be formed can be reliably formed while preventing layer dissolution between the adjacent layers.

As described above, a plurality of light-emitting elements 1A are formed corresponding to the driving transistors 24.

[10] Subsequently, a sealing substrate 20 is prepared, and an epoxy-based adhesive is interposed between the cathode cover 34 and the sealing substrate 20, and then, this adhesive is dried.

By doing this, the cathode cover 34 (cathode 8) and the sealing substrate 20 can be joined to each other so as to cover the cathode cover 34 (cathode 8) with the sealing substrate 20 through an epoxy layer 35.

This sealing substrate 20 exhibits a function as a protective substrate which protects the respective light-emitting elements 1A. By adopting a configuration in which such a sealing substrate 20 is provided on the cathode 8 side, the contact of the light-emitting element 1A with oxygen or water can be more favorably prevented or reduced, and therefore, the reliability of the light-emitting element 1A can be improved, and the effect of prevention of alteration or deterioration or the like can be more reliably obtained.

By undergoing the steps as described above, the light-emitting device 100 in which the respective light-emitting elements 1A are sealed by the sealing substrate 20 is completed.

In the meantime, according to the invention, the light-emitting device 100 including the light-emitting element 1A having such a configuration emits visible light with a luminance of 5 $cd/m^2$ or more when a current is applied between the anode 3 and the cathode 8 at a current density of 300 $mA/cm^2$ or less.

According to this, the light-emitting element 1A not only emits light in a near-infrared region, but also emits visible light with a luminance of 5 $cd/m^2$ or more. Due to this, in a pre-shipment inspection for removing a light-emitting device in which a defect such as a dark spot, nonluminescence, or a pixel defect caused by a foreign substance, an air bubble, or the like as a defective product, the defect can be observed by the naked eye based on the visible light with a luminance of 5 $cd/m^2$ or more emitted when turning on the light-emitting device 100. Therefore, in the same manner as other display devices which emit visible light in the related art, it becomes possible to easily distinguish whether the light-emitting device 100 to be inspected is a defective product or not in the pre-shipment inspection.

That is, in the light-emitting device 100, it is possible to perform a pre-shipment inspection (an inspection method of the invention) for removing a display device in which the above-mentioned defect occurs as a defective product by applying a current between the anode 3 and the cathode 8 at a current density of 300 $mA/cm^2$ or less and observing the emitted visible light with a luminance of 5 $cd/m^2$ or more.

Here, the light-emitting element 1A which not only can emit light in a near-infrared region, but also can emit visible light can be realized by appropriately selecting the types of the hole injection material, the host material, and the electron transport material to be contained in the hole injection layer 4, the light-emitting layer 5, and the electron transport layer 6, respectively, included in the light-emitting element 1A.

Specifically, for example, as the hole injection material to be contained in the hole injection layer 4, by using an amine-based material as described above, the hole injection layer 4 can be made to emit blue light, and as the host material to be contained in the light-emitting layer 5, by using a tetracene-based material, the light-emitting layer 5 can be made to emit green light, and further, as the electron transport material to be contained in the electron transport layer 6, by using an anthracene-based material, the electron transport layer 6 can be made to emit blue light. Therefore, by appropriately selecting the color of light to be emitted by the hole injection layer 4, the light-emitting layer 5, and the electron transport layer 6, the light-emitting element 1A can be made to emit light of a desired color.

Further, the light-emitting element 1A which emits visible light with a luminance of 5 $cd/m^2$ or more can be realized by, for example, adjusting the content of the host material to be contained in the light-emitting layer 5 as well as by adjusting the film thickness of each of the hole injection layer 4, the light-emitting layer 5, and the electron transport layer 6.

Specifically, the average thickness of such a hole injection layer 4 is preferably 5 nm or more and 200 nm or less, more preferably 10 nm or more and 150 nm or less although it varies depending on the type of the hole injection material, a light emission wavelength, or a light extraction structure (bottom emission or top emission).

Further, the average thickness of the light-emitting layer 5 is preferably 5 nm or more and 100 nm or less, more preferably 5 nm or more and 50 nm or less although it slightly varies depending on the type of the host material, the type of the light-emitting material, and the number of stacked light-emitting layers.

Further, the thickness of the entire electron transport layer 6 is preferably 20 nm or more and 200 nm or less, more preferably 50 nm or more and 150 nm or less although it varies depending on the type of the electron transport material, a light emission wavelength, or a light extraction structure (bottom emission or top emission).

By setting the average thickness of each of the hole injection layer 4, the light-emitting layer 5, and the electron transport layer 6 within the above range, the light-emitting element 1A is made to reliably emit visible light with a luminance of 5 $cd/m^2$ or more. Further, by setting the average thickness of the light-emitting layer 5 within the above range, the life of the light-emitting element 1A can be extended while suppressing the driving voltage of the light-emitting element 1A. In addition, by setting the average thickness of the electron transport layer 6 within the above range, electrons can be efficiently transported and injected into the light-emitting layer 5 while suppressing the driving voltage of the light-emitting element 1A.

Further, in the case where the light-emitting layer 5 contains the light-emitting material and the host material as described above, the content (doping amount) of the light-emitting material in the light-emitting layer 5 is preferably 4.0 wt % or less, more preferably 0.25 wt % or more and 2.0 wt % or less. According to this, in the light-emitting layer 5, carriers injected into the light-emitting layer 5 is not only consumed by the light-emitting material, but also consumed by the host material or in a layer adjacent to the light-emitting layer so as to be able to emit light, and therefore, the light-emitting element 1A can be made to reliably emit visible light with a luminance of 5 $cd/m^2$ or more. Further, the balance between the luminous efficiency and the life of the light-emitting element 1A can be made excellent.

Further, by making the light-emitting element 1A emit visible light with a luminance of 5 $cd/m^2$ or more, a defect can be observed by the naked eye or using a (visible light) camera at least in a dark room environment, however, the light-emitting element 1A preferably emits visible light with a luminance of 10 $cd/m^2$ or more, more preferably emits visible light with a luminance of 30 $cd/m^2$ or more. By making the light-emitting element 1A emit visible light with a luminance of 10 $cd/m^2$ or more, a defect can be easily observed at least in a dark room environment, and by making the light-emitting element 1A emit visible light with a luminance of 30 $cd/m^2$ or more, a defect can be easily observed even under a fluorescent lamp.

Incidentally, in the case where the light-emitting element 1A is made to emit visible light with a luminance of 5 $cd/m^2$ or more, for example, when the light-emitting element 1A is made to emit light with a wavelength of 450 nm, an energy amount to be supplied to the light-emitting element 1A is 192 $mW/sr/m^2$, when the light-emitting element 1A is made to emit light with a wavelength of 485 nm, an energy amount to be supplied to the light-emitting element 1A is 43 $mW/sr/m^2$, when the light-emitting element 1A is made to emit light with a wavelength of 555 nm, an energy amount to be supplied to the light-emitting element 1A is 7 $mW/sr/m^2$, when the light-emitting element 1A is made to emit light with a wavelength of 640 nm, an energy amount to be supplied to the light-emitting element 1A is 42 mW/sr/m$^2$, and when the light-emitting element 1A is made to emit light with a wavelength of 650 nm, an energy amount to be supplied to the light-emitting element 1A is 69 mW/sr/m$^2$.

In other words, when the light-emitting element 1A is made to emit blue light, an energy amount to be supplied to the light-emitting element 1A is about 200 mW/sr/m$^2$, when the light-emitting element 1A is made to emit green light, an energy amount to be supplied to the light-emitting element 1A is about 40 mW/sr/m$^2$, and when the light-emitting element 1A is made to emit red light, an energy amount to be supplied to the light-emitting element 1A is about 100 mW/sr/m$^2$, and therefore, when the light-emitting element 1A is made to emit visible light, a necessary energy amount to be supplied to the light-emitting element 1A is about 40 to 200 mW/sr/m$^2$ as the total amount.

Therefore, from the viewpoint of the energy amount to be supplied to the light-emitting element 1A, the light-emitting element 1A is preferably made to emit green light. According to this, the light-emitting element 1A can be made to emit visible light with a luminance of 5 cd/m$^2$ or more with high energy efficiency. Further, the observation may be performed using a visible light camera. In the case where the visible light emission of the light-emitting element 1A is observed using a visible light camera, the light-emitting element 1A is preferably made to emit blue light. The visible light camera measures an energy amount by light emission of the light-emitting element 1A, and therefore, in the case where the light-emitting element 1A emits light with the same luminance, by observing blue light with a short wavelength, the light emission of the light-emitting element 1A can be observed with high sensitivity. Further, in the case where the visible light emission of the light-emitting element 1A is observed by the naked eye, the light-emitting element 1A is preferably made to emit green light, and more preferably made to emit white light. According to this, the burden on the eye of an inspector can be reduced.

Further, in the invention, when visible light with a luminance of 5 cd/m$^2$ or more is obtained as the emitted light, the current density when a current is applied between the anode 3 and the cathode 8 is set to 300 mA/cm$^2$ or less. This is because a pre-shipment inspection for removing a defective product of the light-emitting device 100 is generally performed under a condition that the light is continuously turned on for a relatively long time (for example, for 30 seconds or more).

Therefore, for example, when a current is applied between the anode 3 and the cathode 8 at a current density of about 500 mA/cm$^2$, the temperature of the inside of the light-emitting element exceeds the Tg of the constituent material for forming each layer due to heat by the accumulation of heat. As a result, there was a fear that the luminous efficiency of the light-emitting element may be decreased because of fluidization of each layer of the light-emitting element.

On the other hand, by setting the current density to 300 mA/cm$^2$ or less, even if light is continuously turned on for a long time when performing a pre-shipment inspection, each layer can be suppressed or prevented from fluidizing due to heat, and therefore, the decrease in the luminous efficiency of the light-emitting element 1A is accurately suppressed or prevented.

Incidentally, the current density may be set to 300 mA/cm$^2$ or less, but is set to preferably 200 mA/cm$^2$ or less, more preferably 100 mA/cm$^2$ or less. According to this, the above-mentioned effect can be more remarkably exhibited.

(Authentication Device)

Further, the light-emitting device of the invention can be applied to a display device as described above, but can be applied to an authentication device other than this. Hereinafter, an embodiment of a case where the light-emitting device of the invention is applied to an authentication device will be described.

Figure 3:
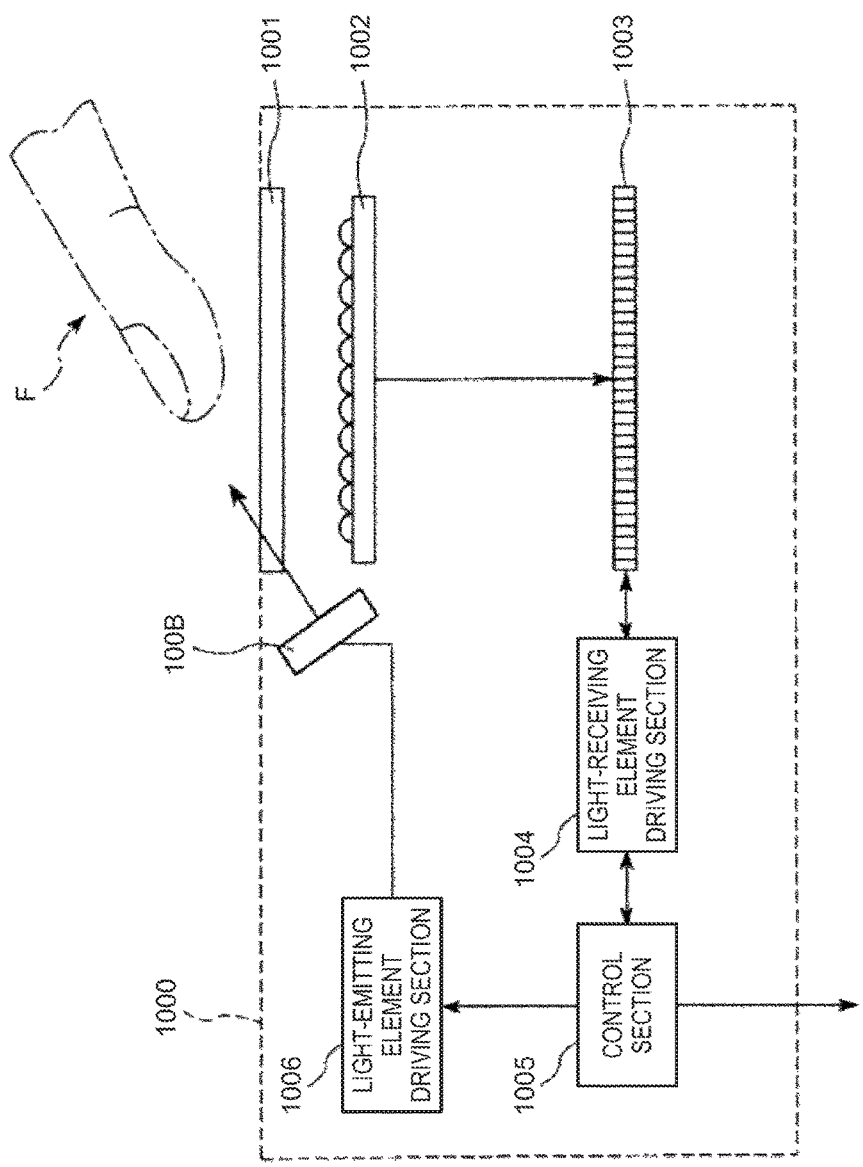
FIG. 3 is a view showing an embodiment of an authentication device to which the light-emitting device is applied.

FIG. 3 is a view showing an embodiment of the authentication device to which the light-emitting device of the invention is applied.

An authentication device 1000 shown in FIG. 3 is a biometric authentication device which authenticates an individual using the biological information of a living body F (in this embodiment, a fingertip).

The authentication device 1000 includes a light source 100B, a cover glass 1001, a microlens array 1002, a light-receiving element group 1003, a light-emitting element driving section 1006, a light-receiving element driving section 1004, and a control section 1005.

The light source 100B includes a plurality of light-emitting elements 1A included in the light-emitting device 100 described above, and irradiates light in a near-infrared region onto the living body F which is the objet to be imaged by surface emission. For example, the plurality of light-emitting elements 1A of the light source 100B are arranged along the outer circumference of the cover glass 1001.

The cover glass 1001 is a part which the living body F comes into contact with or comes close to.

The microlens array 1002 is provided on the opposite side to the side of the cover glass 1001 which the living body F comes into contact with or comes close to. This microlens array 1002 is constituted by a plurality of microlenses arranged in a matrix.

The light-receiving element group 1003 is provided on the opposite side to the cover glass 1001 with respect to the microlens array 1002. The light-receiving element group 1003 is constituted by a plurality of light-receiving elements provided in a matrix corresponding to the plurality of microlenses of the microlens array 1002. As each light-receiving element of the light-receiving element group 1003, for example, a CCD (Charge Coupled Device), a CMOS, or the like can be used.

The light-emitting element driving section 1006 is a driving circuit which drives the light source 100B.

The light-receiving element driving section 1004 is a driving circuit which drives the light-receiving element group 1003.

The control section 1005 is, for example, an MPU, and has a function to control the driving of the light-emitting element driving section 1006 and the light-receiving element driving section 1004.

Further, the control section 1005 has a function to perform authentication of the living body F by comparison between the light reception result of the light-receiving element group 1003 and the previously stored biometric authentication information.

For example, the control section 1005 generates an image pattern (for example, a vein pattern) associated with the living body F based on the light reception result of the light-receiving element group 1003. Then, the control section 1005 compares the formed image pattern and the image pattern previously stored as the biometric authentication information, and performs authentication (for example, vein authentication) of the living body F based on the comparison result.

According to such an authentication device 1000 including the light source 100B, biometric authentication can be performed using near-infrared light. However, the light-emitting device of the invention is applied to this authentication device 1000 including the light source 100B, and by using the inspection method of the invention, it is possible to inspect whether the authentication device 1000 (light source 100B) is a defective product or not.

Further, such an authentication device 1000 can be incorporated into various types of electronic apparatuses.
(Electronic Apparatus)

Figure 4:
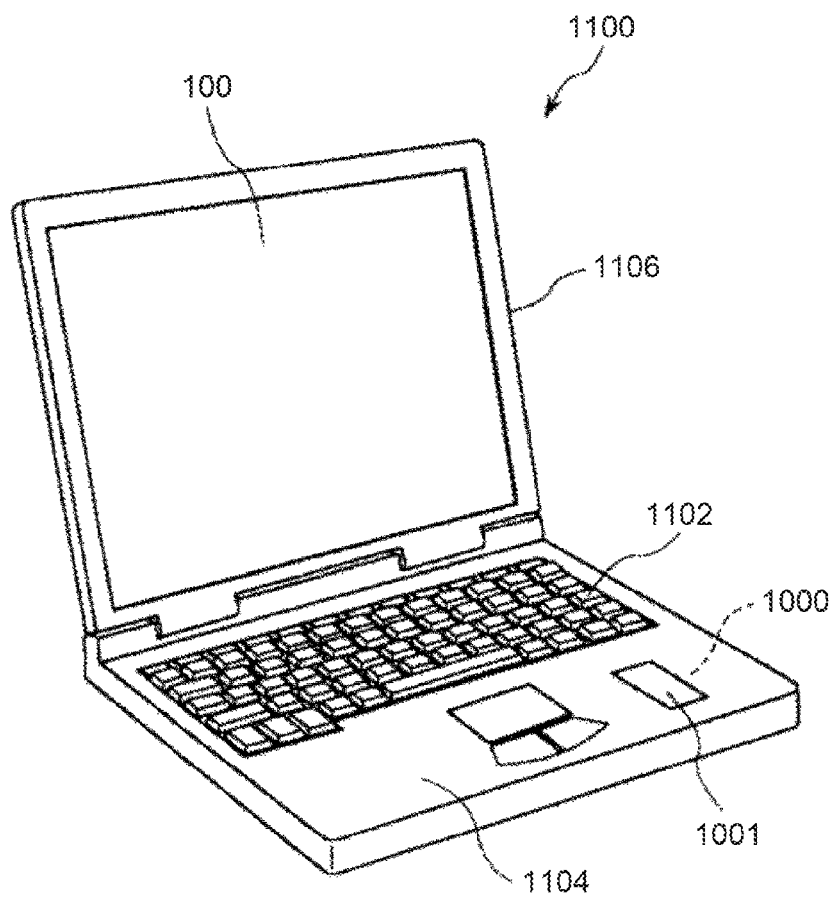
FIG. 4 is a perspective view showing the configuration of a mobile-type (or notebook-type) personal computer to which an electronic apparatus is applied.
Figure 5:
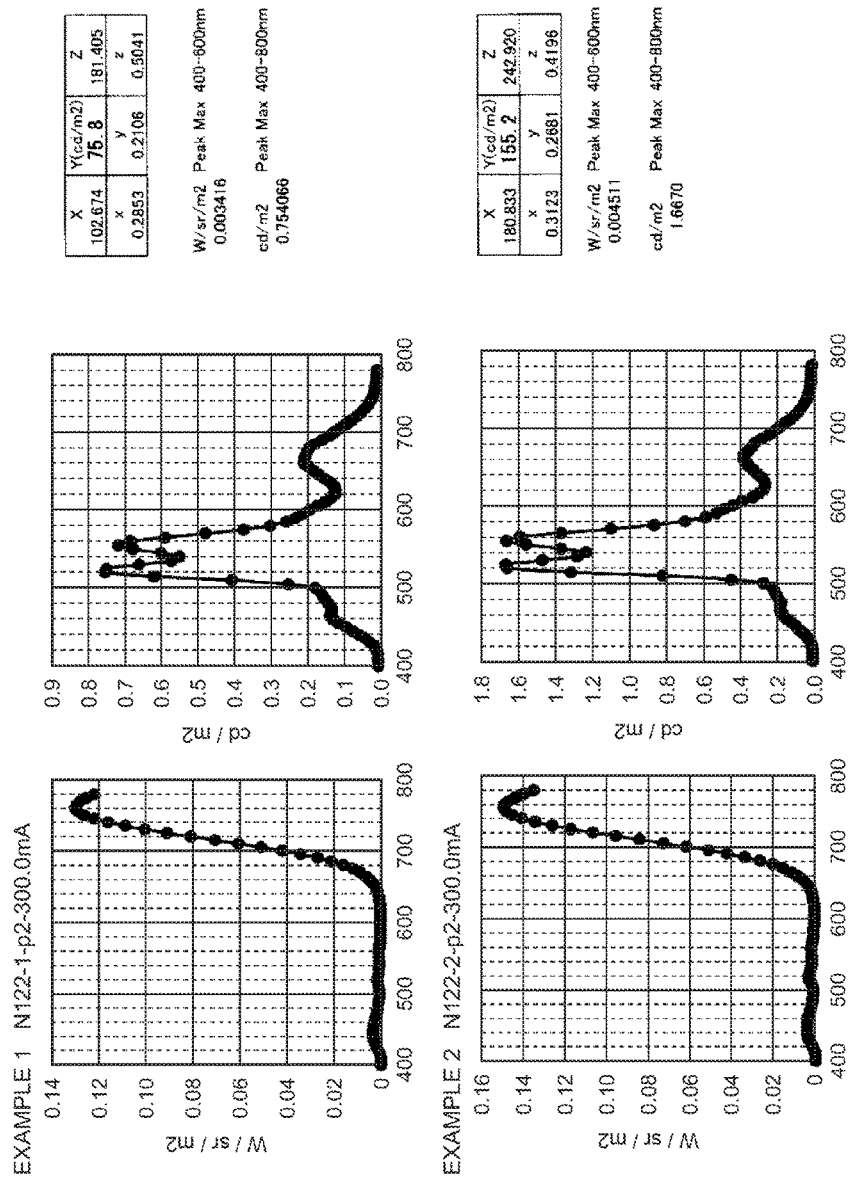
FIG. 5 shows graphs indicating emission spectra of light-emitting elements according to Examples 1 and 2.
Figure 6:
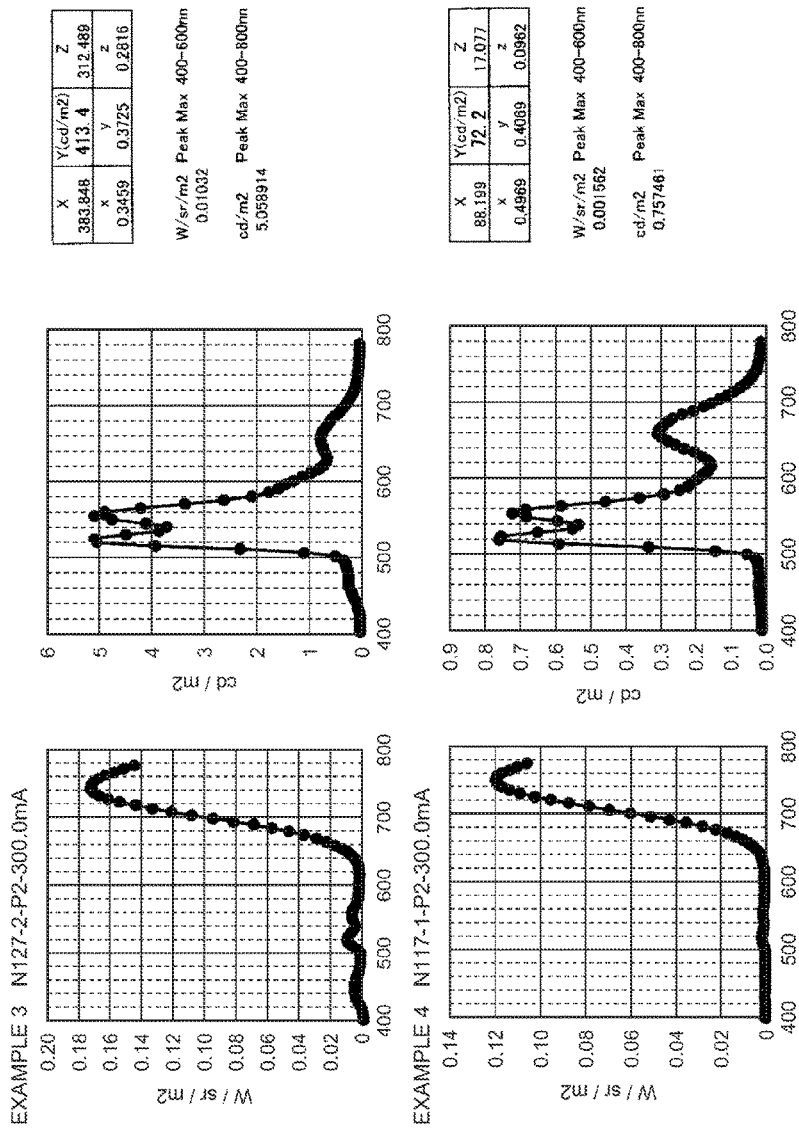
FIG. 6 shows graphs indicating emission spectra of light-emitting elements according to Examples 3 and 4.
Figure 7:
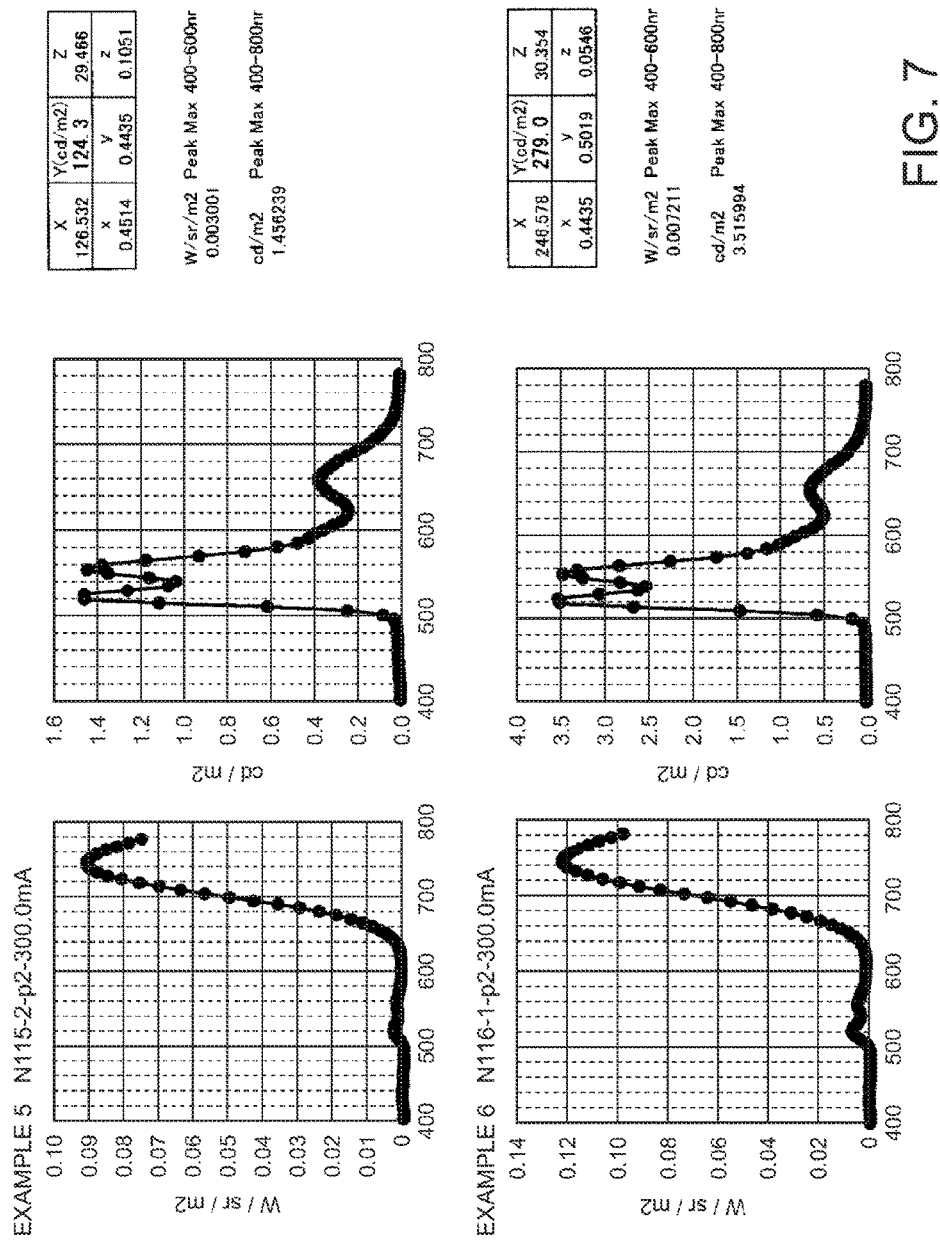
FIG. 7 shows graphs indicating emission spectra of light-emitting elements according to Examples 5 and 6.
Figure 8:
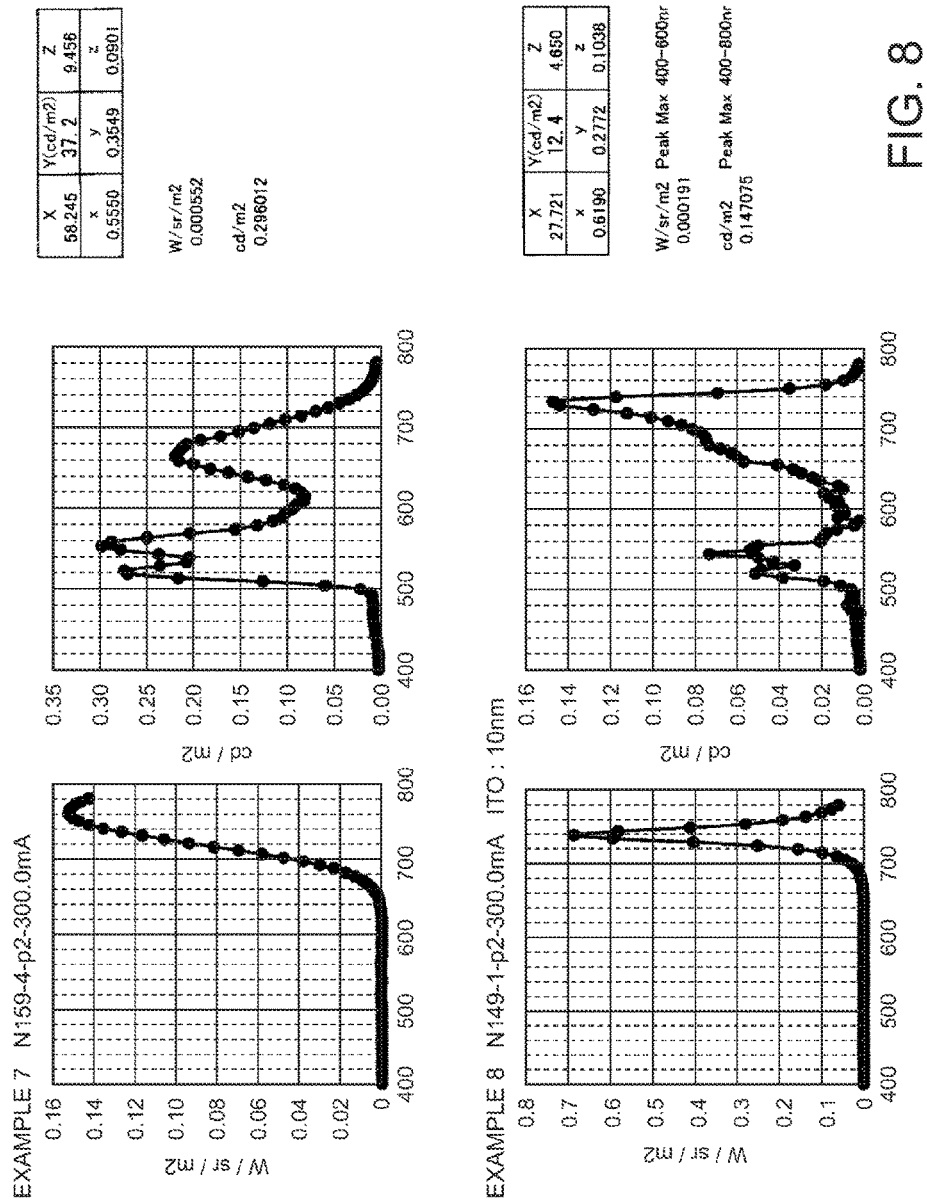
FIG. 8 shows graphs indicating emission spectra of light-emitting elements according to Examples 7 and 8.
Figure 9:
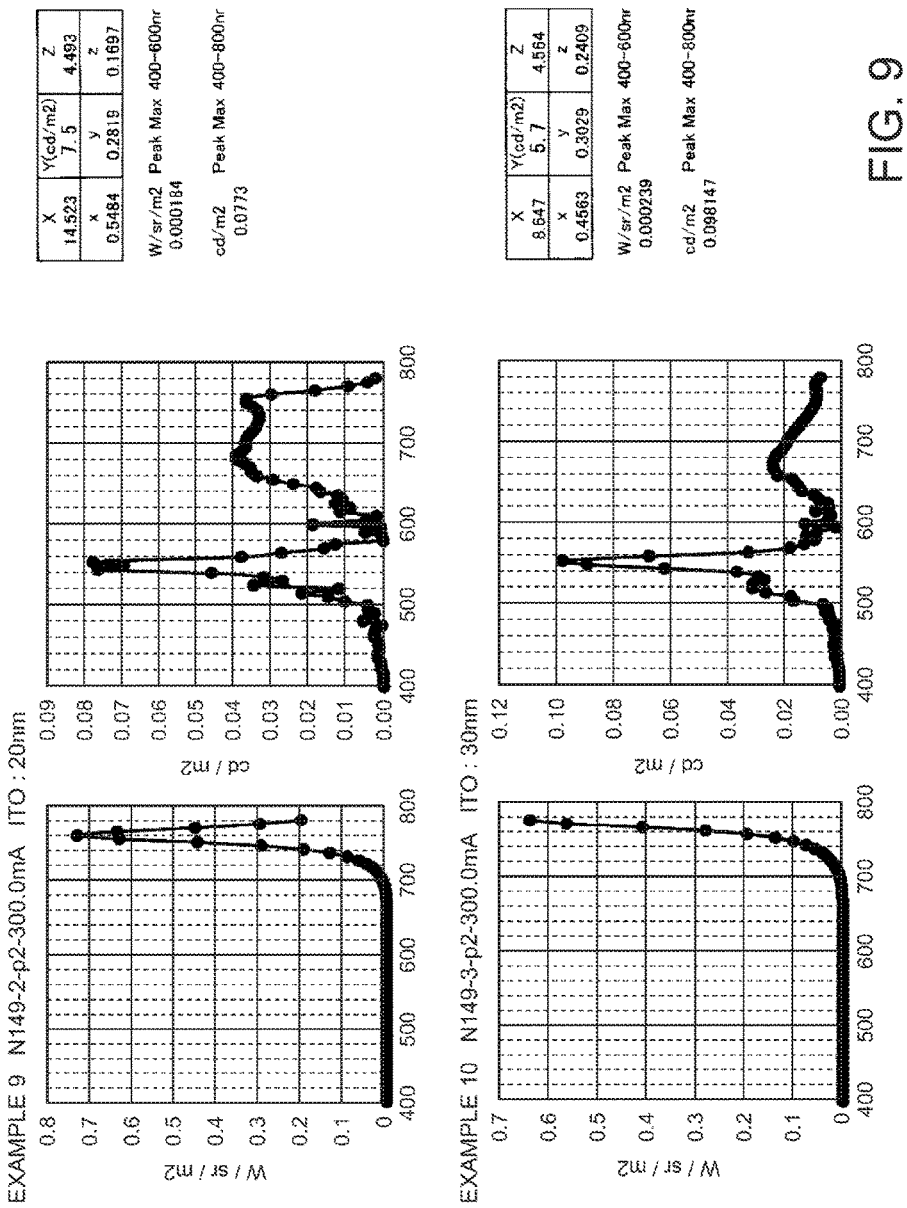
FIG. 9 shows graphs indicating emission spectra of light-emitting elements according to Examples 9 and 10.
Figure 10:
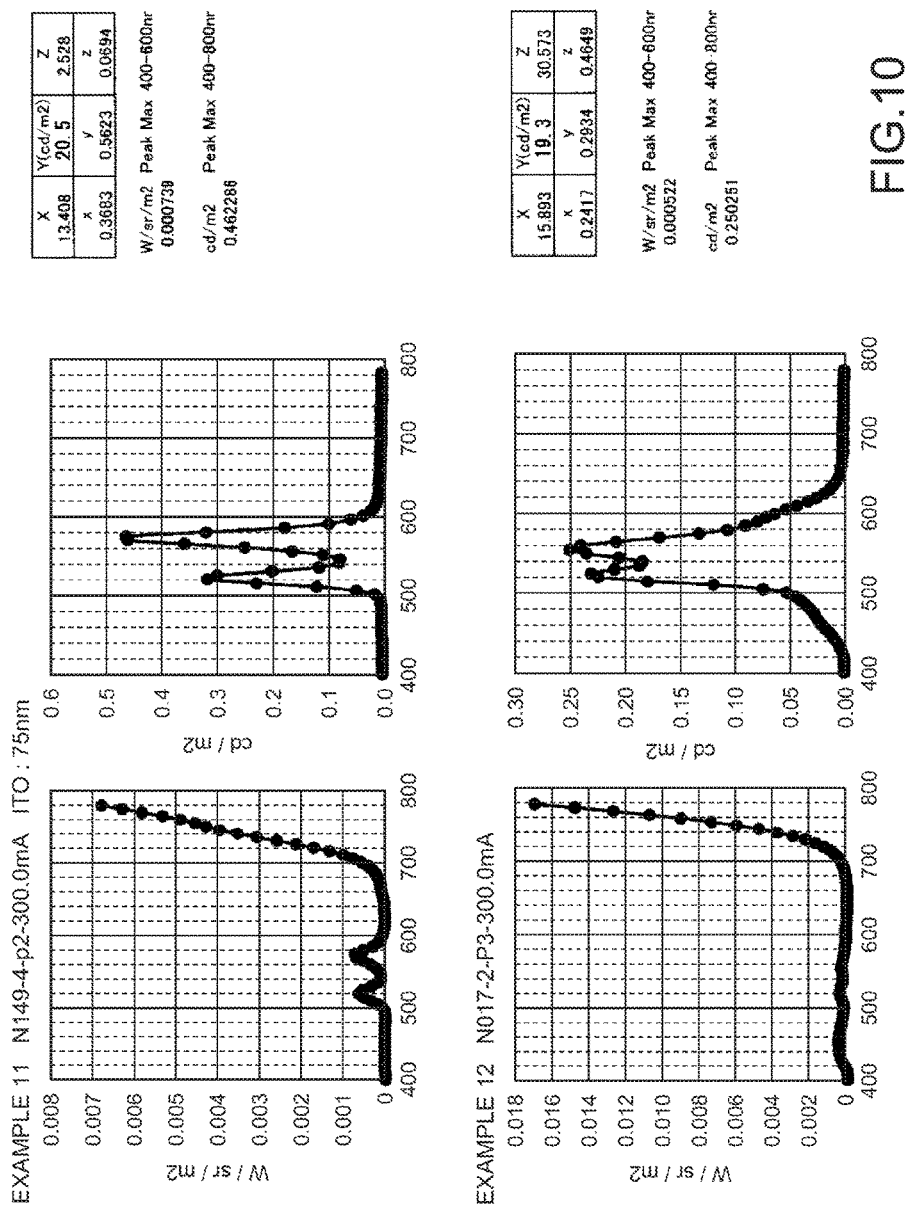
FIG. 10 shows graphs indicating emission spectra of light-emitting elements according to Examples 11 and 12.
Figure 11:
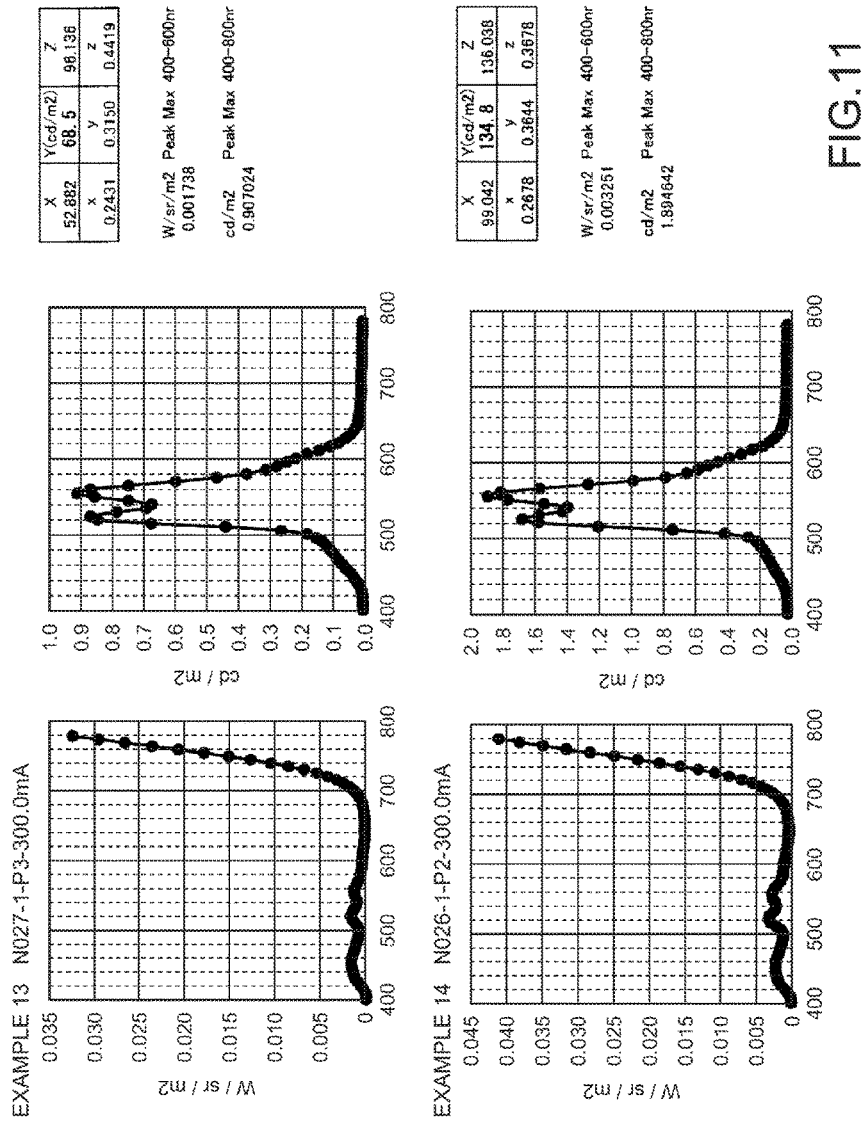
FIG. 11 shows graphs indicating emission spectra of light-emitting elements according to Examples 13 and 14.
Figure 12:
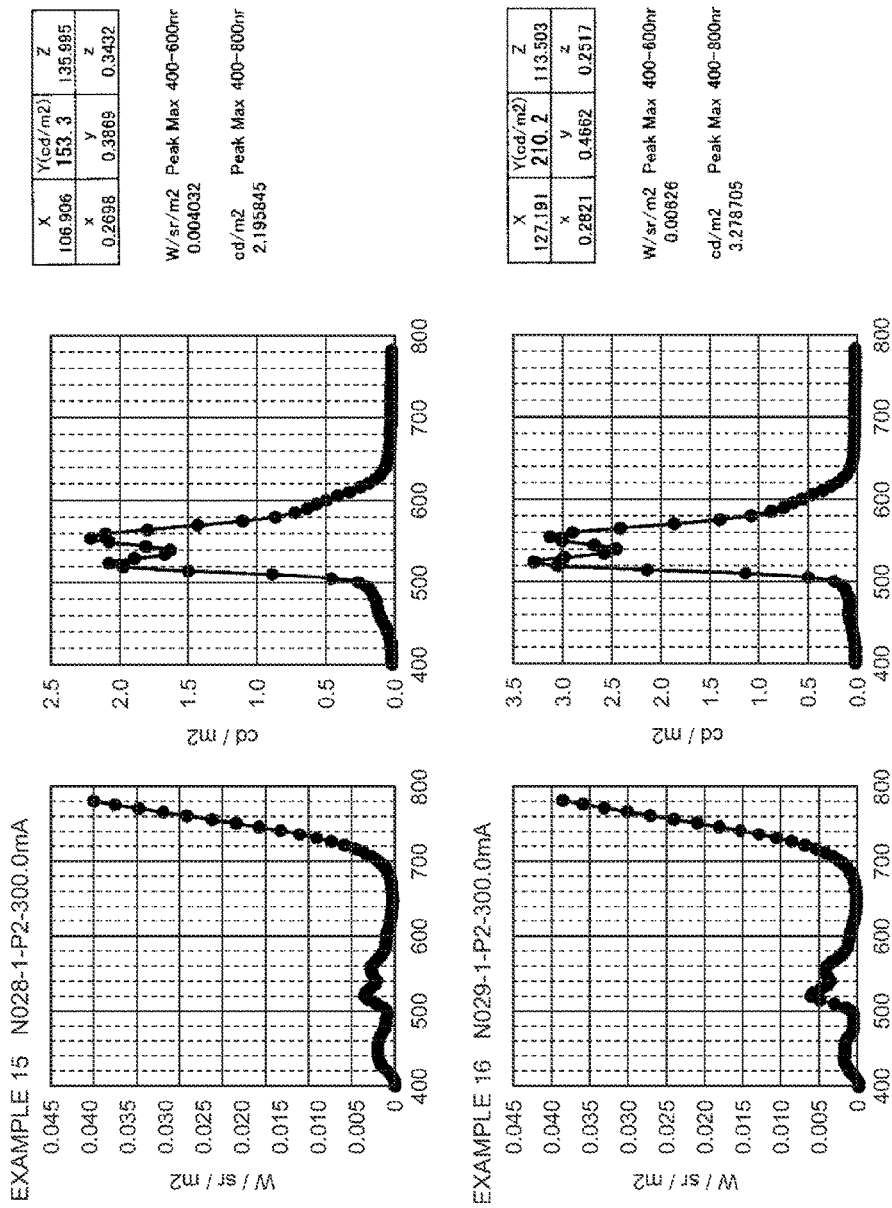
FIG. 12 shows graphs indicating emission spectra of light-emitting elements according to Examples 15 and 16.
Figure 13:
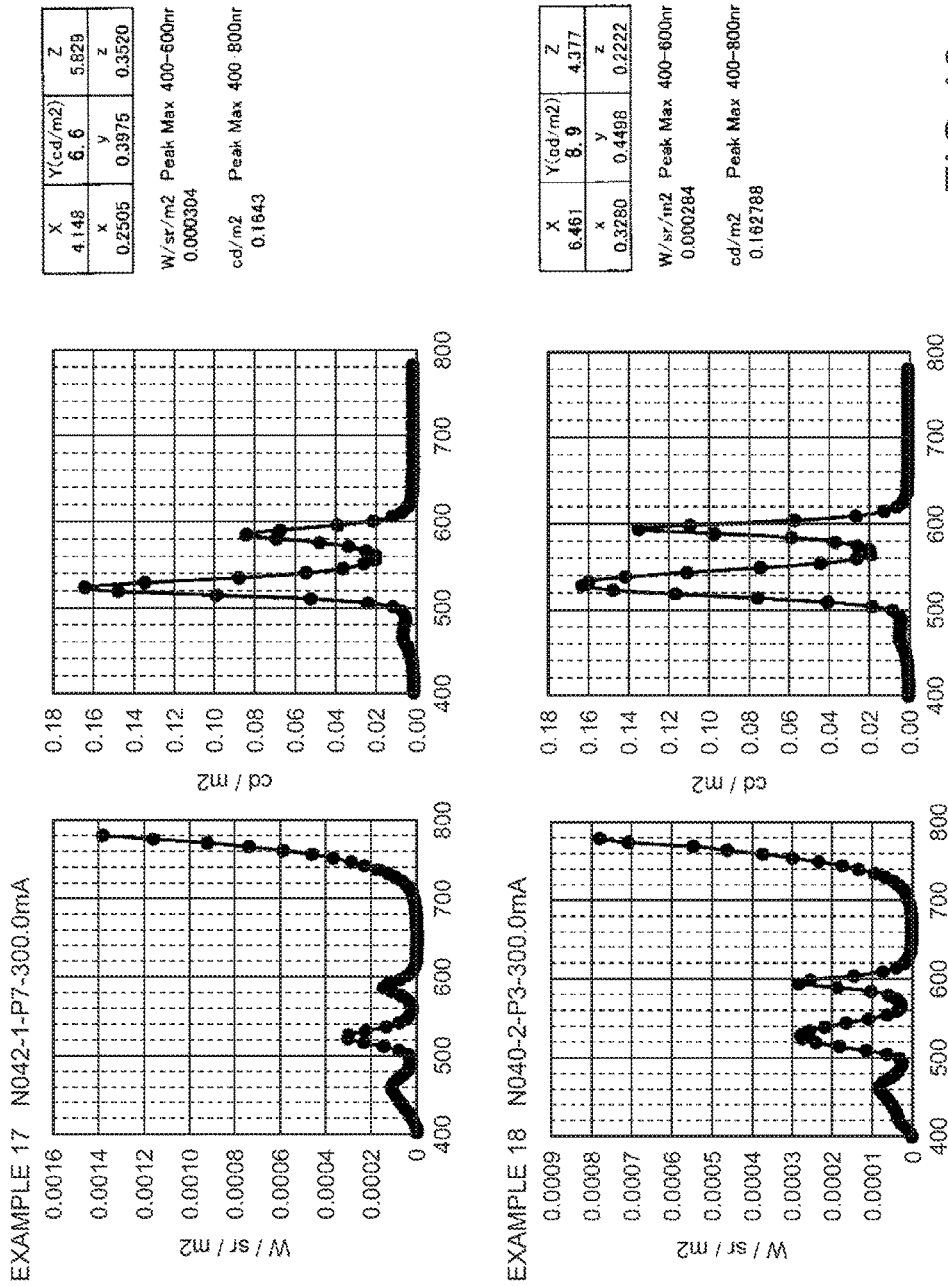
FIG. 13 shows graphs indicating emission spectra of light-emitting elements according to Examples 17 and 18.
Figure 14:
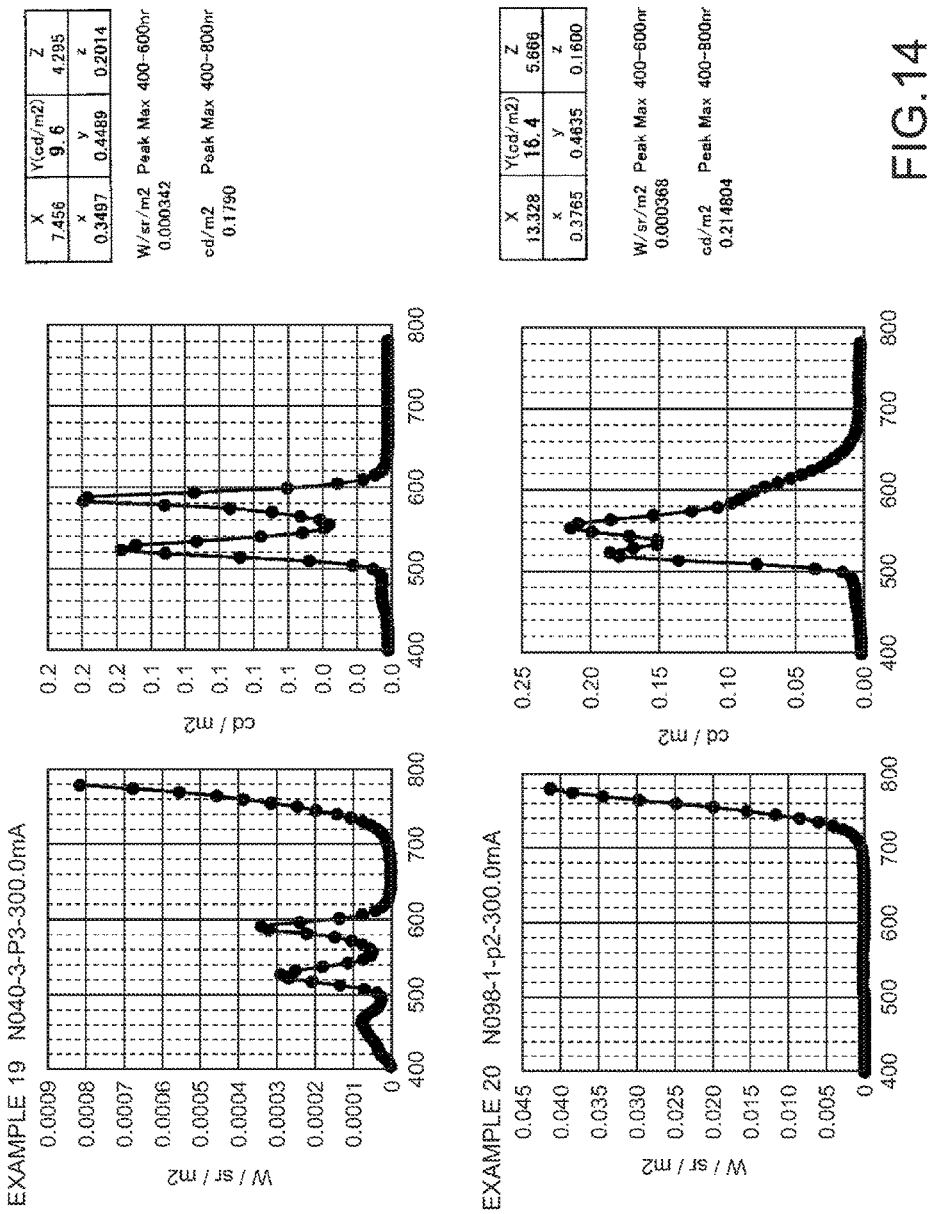
FIG. 14 shows graphs indicating emission spectra of light-emitting elements according to Examples 19 and 20.
Figure 15:
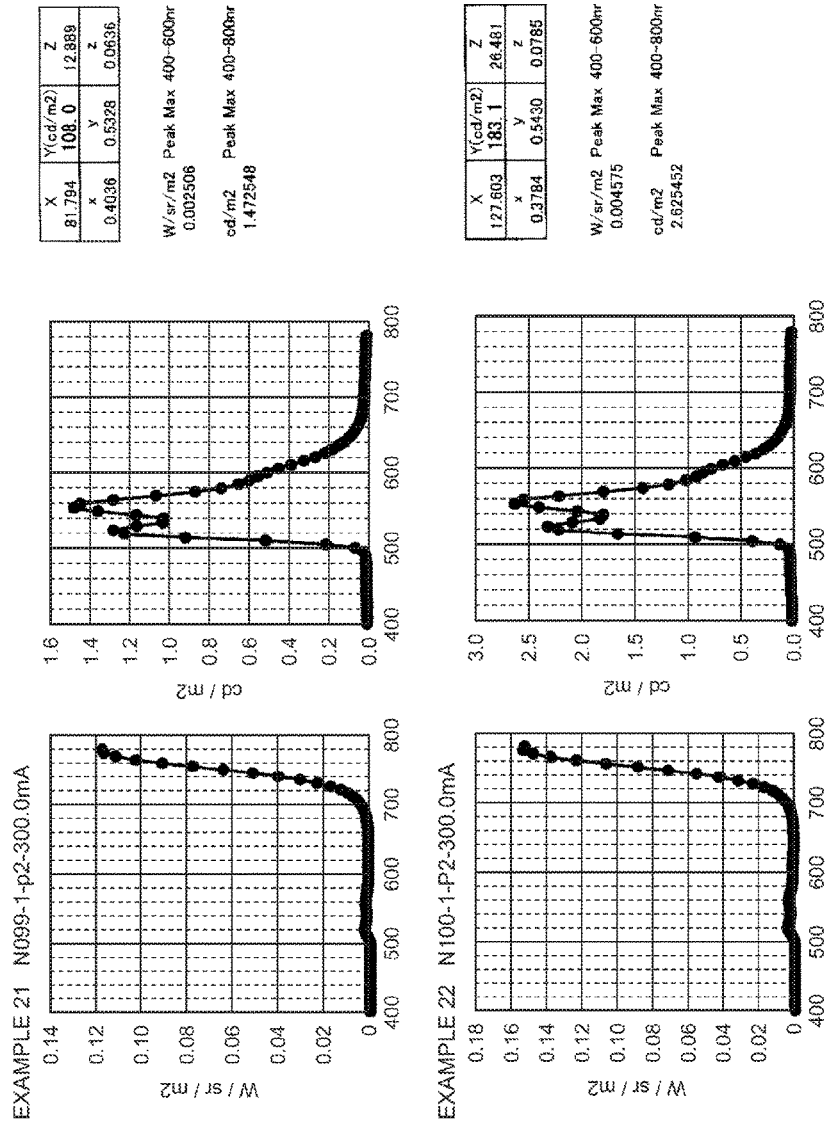
FIG. 15 shows graphs indicating emission spectra of light-emitting elements according to Examples 21 and 22.
Figure 16:
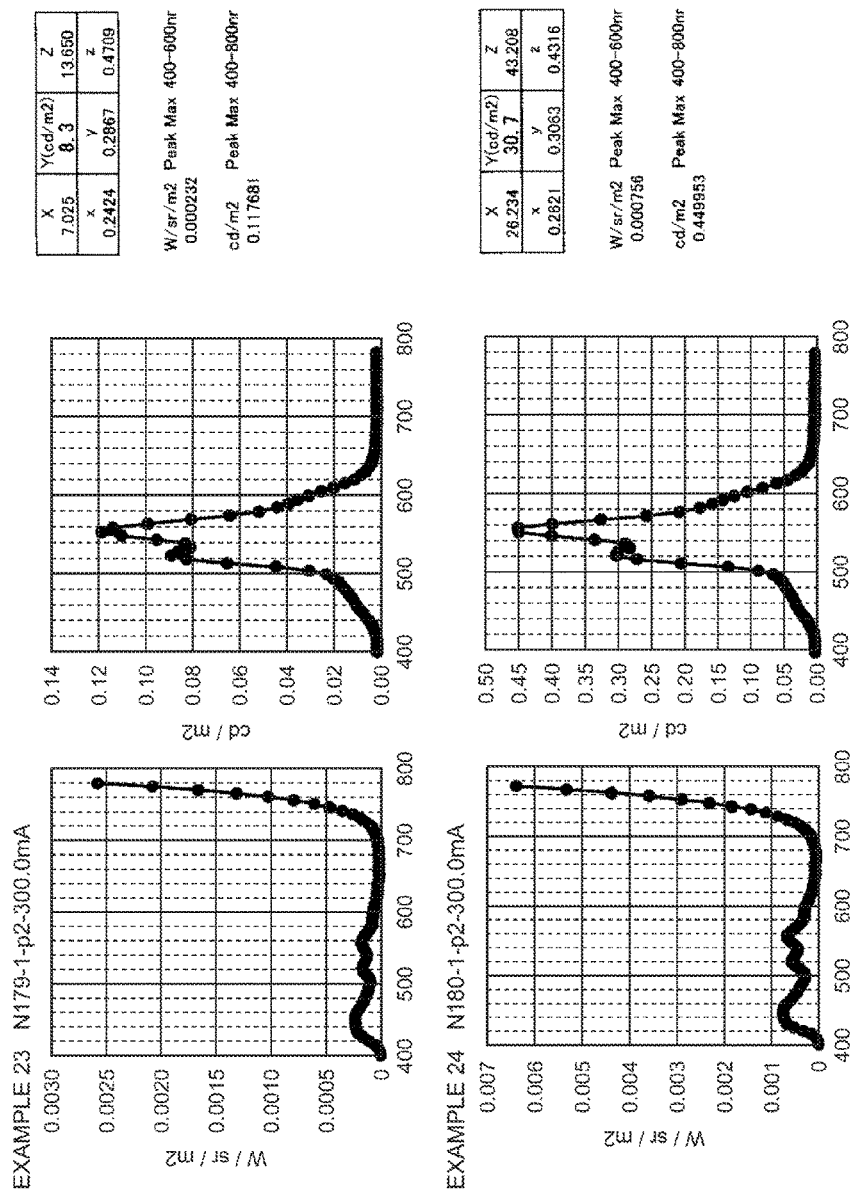
FIG. 16 shows graphs indicating emission spectra of light-emitting elements according to Examples 23 and 24.
Figure 17:
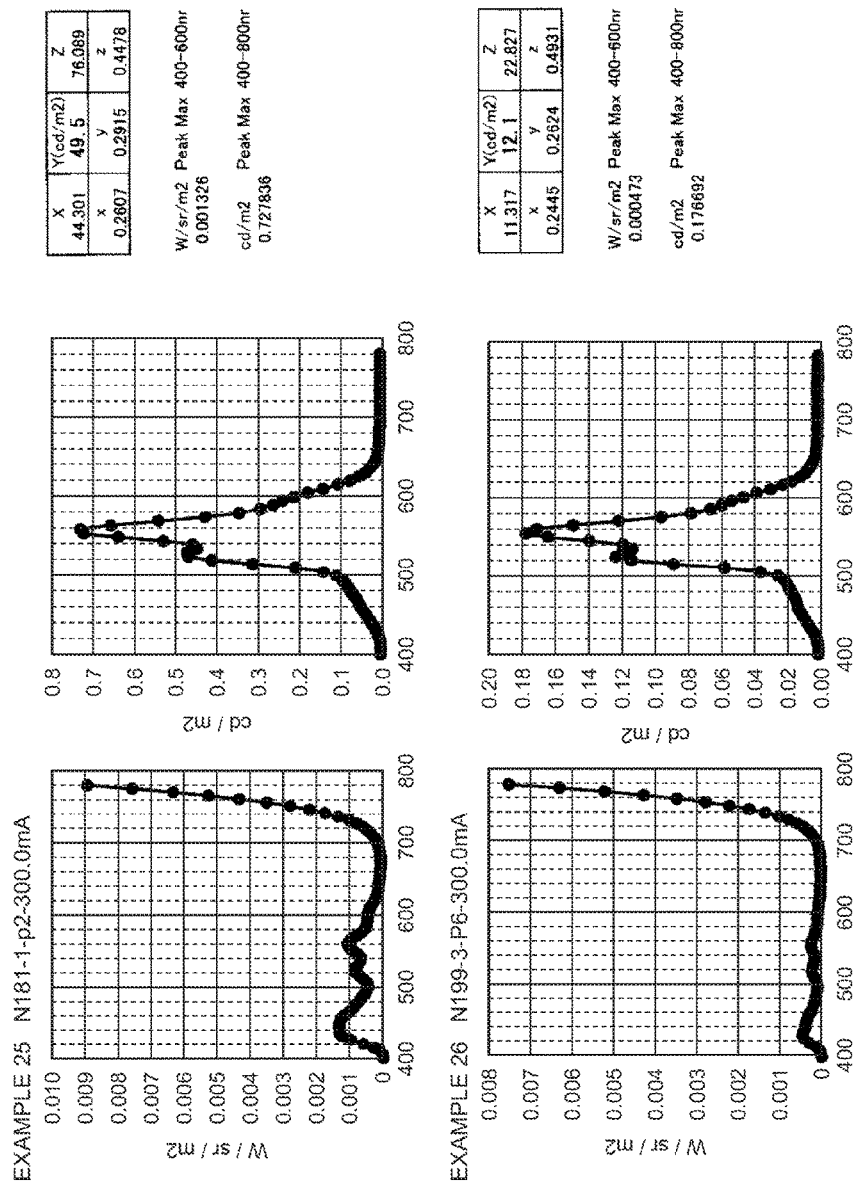
FIG. 17 shows graphs indicating emission spectra of light-emitting elements according to Examples 25 and 26.

FIG. 4 is a perspective view showing the configuration of a mobile-type (or notebook-type) personal computer to which an electronic apparatus of the invention is applied.

In this drawing, a personal computer 1100 is constituted by a main body 1104 provided with a keyboard 1102 and a display unit 1106 provided with a display section, and the display unit 1106 is supported rotatably with respect to the main body 1104 through a hinge structure.

In this personal computer 1100, the main body 1104 is provided with the above-mentioned authentication device 1000.

According to such a personal computer 1100, the light-emitting element 1A which has high efficiency and long life is included, and therefore it has excellent reliability.

Incidentally, the electronic apparatus of the invention can not only be applied to the personal computer (mobile-type personal computer) shown in FIG. 4, but also be applied to, for example, a mobile phone, a digital still camera, a television, a video camera, a view finder-type or monitor direct view-type video tape recorder, a laptop-type personal computer, a car navigation device, a pager, an electronic organizer (including an electronic organizer with a communication function), an electronic dictionary, an electronic calculator, an electronic gaming machine, a word processor, a workstation, a videophone, a security television monitor, electronic binoculars, a POS terminal, an apparatus provided with a touch panel (for example, a cash dispenser in financial institutions and an automatic ticket vending machine), a medical apparatus (for example, an electronic thermometer, a sphygmomanometer, a blood glucose meter, a sphygmometer, a plethysmograph, an electrocardiographic device, an ultrasonic diagnostic device, or a display device for an endoscope), a fish finder, various types of measurement apparatuses, meters and gauges (for example, meters and gauges for vehicles, aircrafts, and ships), a flight simulator, other various types of monitors, a projection-type display device such as a projector, and the like.

Hereinabove, the light-emitting device, the electronic apparatus, and the inspection method of the invention have been described with reference to the embodiments shown in the drawings, however, the invention is not limited thereto.

For example, the light-emitting device of the invention may be used as a light source for lighting.

EXAMPLES

Next, specific examples of the invention will be described.
1. Production of Light-Emitting Material (Production of IRD-15)

[Chem. 28]

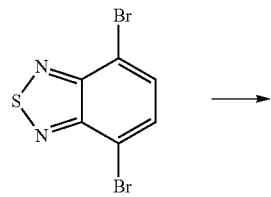

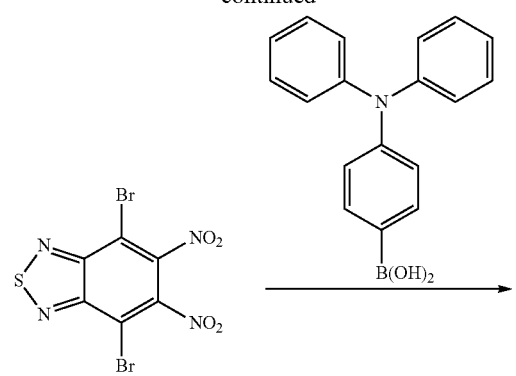

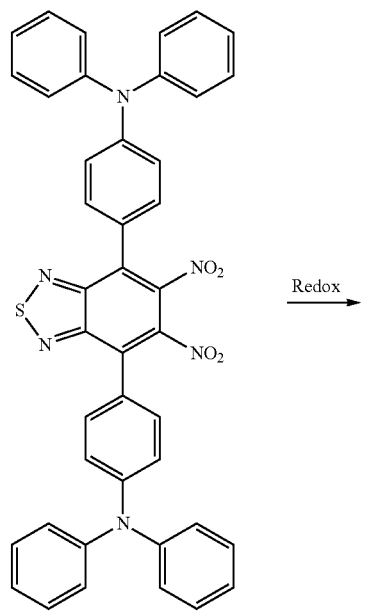

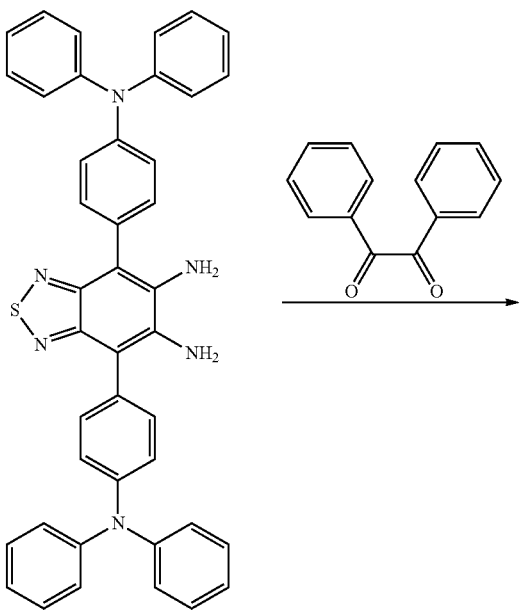

-continued

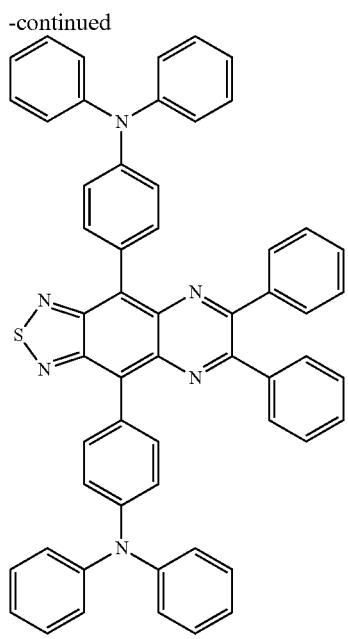

Synthesis (A1-1)

In a 5-L flask, 1500 mL of fuming nitric acid was placed and cooled. Thereto, 1500 mL of sulfuric acid was added in divided portions such that the temperature was maintained at 10 to 50° C. Further, 150 g of a compound (a) which is dibromobenzothiadiazole as a starting material was added thereto in small portions over 1 hour. At this time, the temperature of the solution was maintained at 5° C. or lower. After the addition of the total amount, a reaction was allowed to proceed for 20 hours at room temperature (25° C.). After the reaction, the reaction mixture was poured into 3 kg of ice, followed by stirring overnight. Thereafter, the mixture was filtered, followed by washing with methanol and heptane.

The residue after filtration was thermally dissolved in 200 mL of toluene, and the resulting solution was gradually cooled to room temperature and then filtered. The resulting residue was washed with a small amount of toluene, and then dried under reduced pressure.

By doing this, 60 g of a compound (b) (4,7-dibromo-5,6-dinitro-benzo[1,2,5]thiadiazole) with an HPLC purity of 95% was obtained.
Synthesis (A1-2)

In an Ar atmosphere, in a 5-L flask, 30 g of the compound (b) which is the obtained dibromo compound, 160 g of a triphenylamine boronic acid compound, 2500 mL of toluene, and a 2 M aqueous solution of cesium carbonate (152 g/234 mL of distilled water) were placed, and a reaction was allowed to proceed overnight at 90° C. After the reaction, filtration, liquid separation, and concentration were performed, and 52 g of the resulting crude material was separated using a silica gel column (5 kg of SiO$_2$), whereby a red-purple solid was obtained.

By doing this, 6 g of a compound (c) (5,6-dinitro-4,7-diphenyl-benzo[1,2,5]thiadiazole) with an HPLC purity of 96% was obtained.
Synthesis (A1-3)

In an Ar atmosphere, in a 1-L flask, 6 g of the compound (c) which is the obtained dinitro compound, 7 g of reduced iron, and 600 mL of acetic acid were placed, and a reaction was allowed to proceed at 80° C. for 4 hours, and then the mixture was cooled to room temperature. After the reaction, the reaction mixture was poured into 1.5 L of ion exchanged water, and then, 1.5 L of ethyl acetate was further added thereto. After the addition, a solid was deposited, and therefore, 1 L of tetrahydrofuran and 300 g of sodium chloride were added thereto, and liquid separation was performed. The aqueous layer was reextracted with 1 L of tetrahydrofuran, followed by concentration and drying. The resulting residue was again washed with a small amount of water and methanol, whereby an orange solid was obtained.

By doing this, 7 g of a compound (d) (4,7-diphenyl-benzo[1,2,5]thiadiazolo-5,6-diamine) with an HPLC purity of 80% was obtained.
Synthesis (A1-4)

In an Ar atmosphere, in a 1-L flask, 4.5 g of the compound (d) which is the obtained diamine compound, 3.7 g of benzil, and 300 mL of acetic acid as a solvent were placed, and a reaction was allowed to proceed at 80° C. for 2 hours. After the reaction, the reaction mixture was cooled to room temperature, and then poured into 1 L of ion exchanged water. The resulting crystal was filtered and washed with water, whereby 7 g of a black-green solid was obtained. Then, this black-green solid was purified using a silica gel column (1 kg of SiO$_2$).

By doing this, 4 g of a compound (e) (a compound represented by the above formula IRD-15) with an HPLC purity of 99% was obtained. This compound (e) was subjected to mass analysis, and the result was as follows: M+: 492.

Further, the obtained compound (e) was purified by sublimation at a set temperature of 340° C. The HPLC purity of the compound (e) after the purification by sublimation was 99%.

(Production of IRD-24)

[Chem. 29]

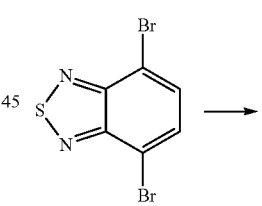

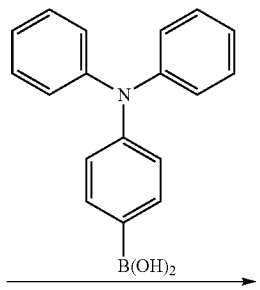

97
-continued

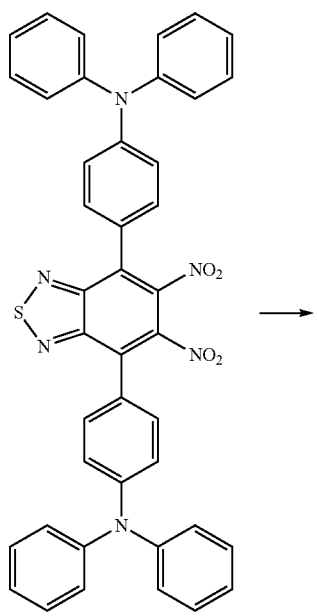

→

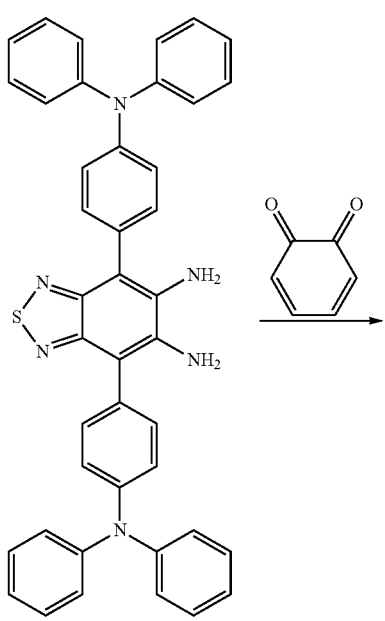 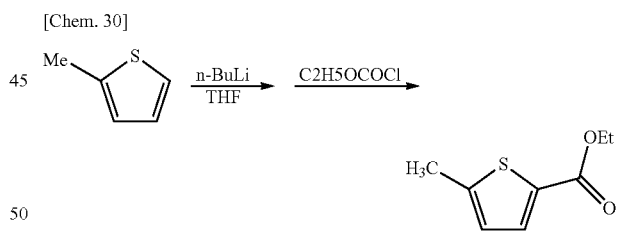

98
-continued

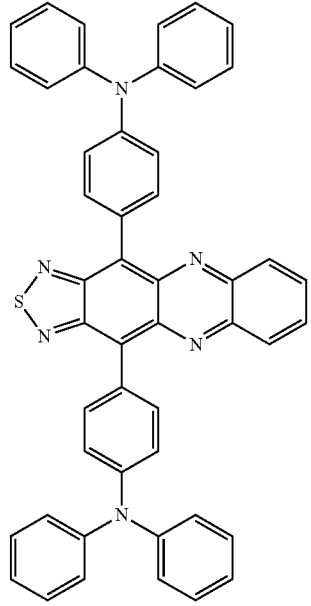 [SMILES: c1ccc(N(c2ccccc2)c2ccc(-c3c4nsnc4c(-c4ccc(N(c5ccccc5)c5ccccc5)cc4)c4nc5ccccc5nc34)cc2)cc1]

Synthesis was performed in the same manner as the above-mentioned synthesis of IRD-15 except that 1,2-benzoquinone was used in place of benzil used in the synthesis (A1-4) in the synthesis of the above formula IRD-15 described above. By doing this, a compound represented by the above IRD-24 was obtained.

(Production of IRD-31)

A pyrromethene-based boron complex represented by the above formula IRD-31 was synthesized by the following steps 1 to 6.

[Step 1] Synthesis of Ethyl Ester Compound (5-Methyl-thiophene-2-carboxylic Acid Ethyl Ester)

[Chem. 30]

In an Ar gas stream, in a 1-L three-necked flask, 2-methylthiophene (1.7 g, 0.175 mol) was added to dehydrated THF (150 mL), and the resulting mixture was cooled to −65° C. Thereafter, a 1.6 M n-BuLi hexane solution (120 mL, 0.19 mol) was added dropwise thereto at −60° C. or lower, followed by stirring as such for 1 hour.

Subsequently, 2-ethyl chloroformate ($C_2H_5OCOCl$: 2.1 g, 0.19 mol) was added to dehydrated THF (10 mL), and the resulting solution was cooled to −55° C. or lower. This solution was added dropwise to the previously prepared solution at −50° C. or lower. After the dropwise addition, the cooling of the reaction mixture was stopped, and the temperature was raised to room temperature overnight.

After the reaction, 50 mL of water was added dropwise to the solution, followed by stirring. After an organic layer was fractionated using a separating funnel, a concentration operation was performed under reduced pressure.

The obtained crude material (35 g) was purified by silica gel chromatography (500 g, development: $CH_2Cl_2$/Hep=1/2→$CH_2Cl_2$/Hep=1/1), whereby an ethyl ester compound which is a target material was obtained (yield amount: 8.1 g, yield percentage: 27%).

[Step 2] Synthesis of Hydrazide Compound (5-Methyl-thiophene-2-carboxylic Acid Hydrazide)

[Chem. 31]

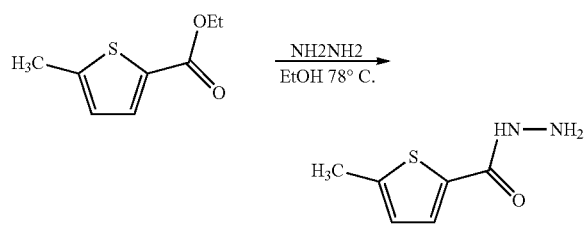

In an Ar gas stream, in a 300-mL three-necked flask, the ethyl ester compound (8.1 g, 48 mmol) obtained in the step 1 was suspended in ethanol (100 mL), and $NH_2NH_2 \cdot H_2O$ (7 mL, 140 mmol) was added thereto, and a reaction was allowed to proceed overnight while heating to 78° C. After disappearance of the ethyl ester compound was confirmed by monitoring the resulting reaction mixture, the reaction mixture was cooled to room temperature.

The reaction mixture was transferred to a 1-L beaker, and 300 mL of $CH_2Cl_2$ and 100 mL of distilled water were added thereto, followed by stirring. The total amount of the mixture was transferred to a 1-L separating funnel to fractionate an organic layer, and the organic layer was washed twice with distilled water. Finally, after the organic layer was fractionated, the organic layer was concentrated, and then, about 20 mL of heptane was added thereto. The resulting precipitate was filtered, whereby a hydrazide compound which is a target material was obtained (yield amount: 3 g, yield percentage: 40%).

[Step 3] Synthesis of Intermediate (5-Methyl-thiophene-2-carboxylic Acid [1-(2-hydroxy-4-methoxy-phenyl)-ethylidene]-hydrazide)

[Chem. 32]

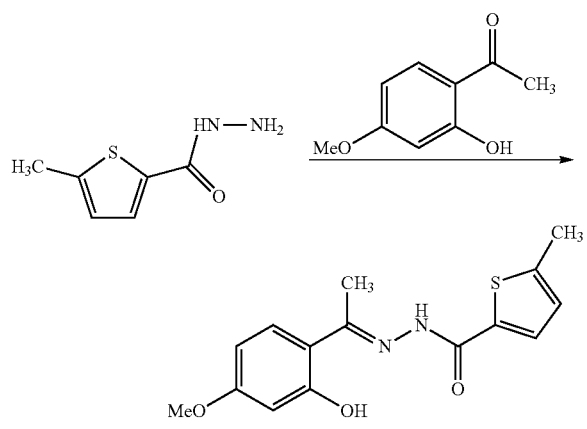

In an Ar gas stream, to a 30-mL three-necked flask, the hydrazide compound (2.64 g, 16.9 mmol) obtained in the step 2 and 2-hydroxy-4-methoxyacetophenone (2.84 g, 17.1 mmol) were added, followed by stirring for 10 hours at an external temperature of 80° C.

After cooling to room temperature, in order to extract a target material from the reaction mixture, THF was used, and after concentration under reduced pressure, heptane was added thereto to effect precipitation, whereby an intermediate which is the target material was obtained (yield amount: 4.4 g, yield percentage: 85%).

[Step 4] Synthesis of Diketone Compound (1-[4-Methoxy-2-(5-methyl-thiophene-2-carbonyl)-phenyl]-ethan One)

[Chem. 33]

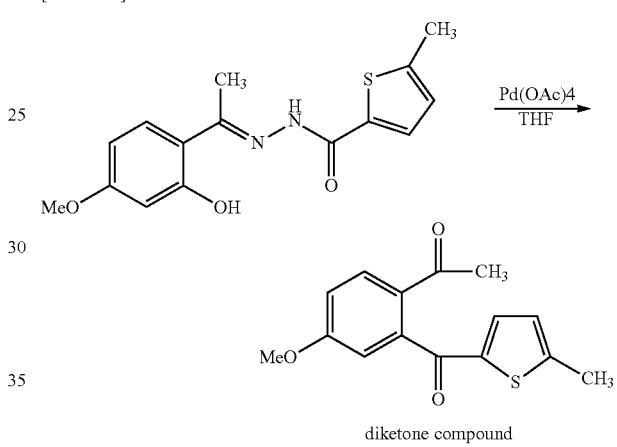

diketone compound

In an Ar gas stream, in a 100-mL three-necked flask, the intermediate (2.25 g, 7.39 mmol) obtained in the step 3 was suspended in dehydrated THF (35 mL), and Pb(OAc)4 (3.93 g, 8.86 mmol) was slowly added thereto at 30° C. or lower. After stirring overnight, the reaction mixture was filtered, and the filtrate was concentrated under reduced pressure. The resulting residue was subjected to washing and extraction using $CH_2Cl_2$ (100 mL) and distilled water (100 mL), followed by concentration, whereby a diketone compound which is a target material was obtained (yield amount: 2.2 g).

[Step 5] Synthesis of Precursor

[Chem. 34]

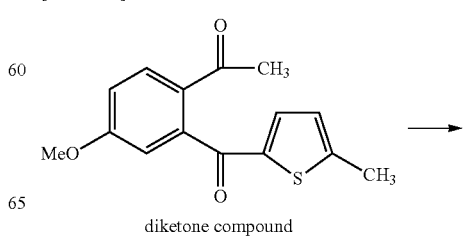

diketone compound

-continued

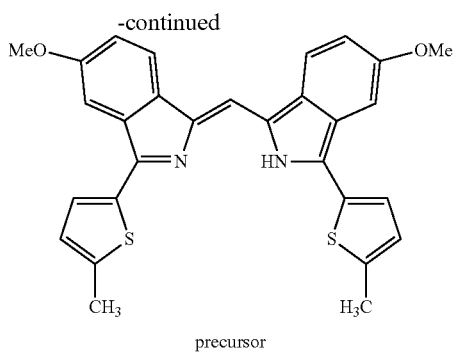
precursor

In an Ar gas stream, in a 100-mL three-necked flask, the diketone compound (3.0 g, 10.9 mmol) obtained in the step 4 was added to 30 mL of acetic acid and 100 mL of EtOH, and the resulting mixture was heated at an internal temperature of 65° C. Thereafter, ammonium acetate (5.1 g, 66.4 mmol) and ammonium chloride (583 mg, 10.9 mmol) were added thereto, followed by stirring as such for 5 hours. Further, the reaction temperature was raised to 85° C., and the mixture was stirred for about 1 hour.

The reaction mixture was cooled to room temperature, and a concentration operation was performed under reduced pressure. The resulting residue was poured into water (300 mL), and an extraction operation was performed using $CH_2Cl_2$. The obtained organic layer was subjected to a concentration operation under reduced pressure. Then, the obtained crude material was purified by silica gel chromatography (100 g, development: $CH_2Cl_2 \rightarrow CH_2Cl_2+THF$ (50:50)), whereby a precursor which is a target material was obtained (yield amount: 830 mg, yield percentage: 29%).

[Step 6] Synthesis of IRD-31

[Chem. 35]

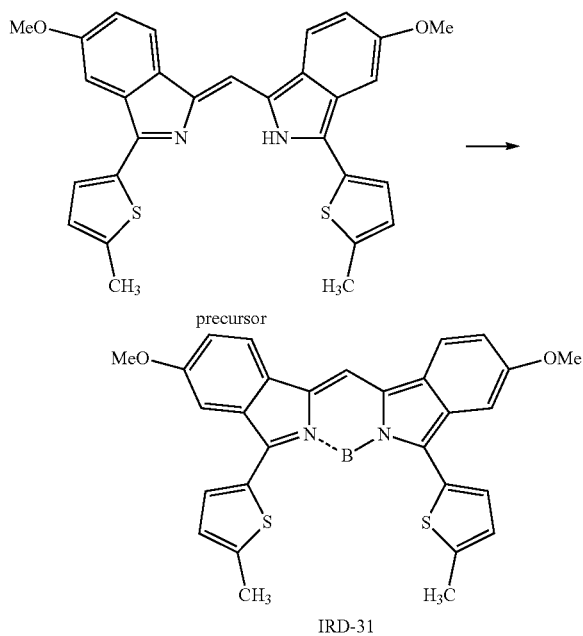

IRD-31

In an Ar gas stream, in a 100-mL three-necked flask, the precursor (830 mg, 1.58 mmol) obtained in the step 5 was dissolved in dehydrated $CH_2Cl_2$ (100 mL), and the resulting solution was cooled to 5° C. Thereto, N,N-diisopropylethylamine (611 mg, 4.73 mmol) and $BF_3.OEt2$ (1.34 g, 9.46 mmol) were sequentially added dropwise, and the temperature was raised to room temperature. After the mixture was stirred for about 2 hours, a washing operation was performed by adding water (100 mL) thereto. The obtained organic layer was purified by silica gel chromatography (100 g, development: $CH_2Cl_2$), whereby a compound represented by the above formula IRD-31 which is a target material was obtained (yield amount: 600 mg, yield percentage: 70%).

(Production of IRD-41)

A benzo-bis-thiadiazole-based compound represented by the above formula IRD-41 was synthesized by the following steps 1 to 6.

Step 1

[Chem. 36]

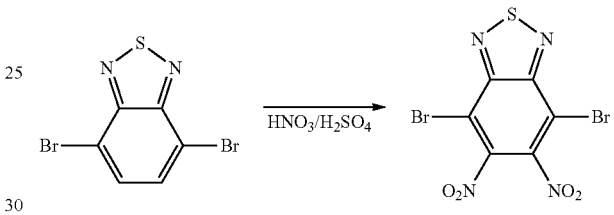

First, to a 1-L three-necked flask, 345 mL of fuming nitric acid (97%) was added and cooled to an internal temperature of 5° C. Thereto, concentrated sulfuric acid (95%) (345 mL) was added slowly in divided portions at an internal temperature of 10° C. or lower. After completion of the addition, the resulting mixture was left at room temperature and stirred overnight.

Subsequently, the reaction mixture was poured into ice water (1 L), and the resulting solid was filtered. To the obtained solid (30 g), toluene (100 mL) was added to effect recrystallization, whereby a target material was obtained (yield amount: 16 g, yield percentage: 33%).

Step 2

[Chem. 37]

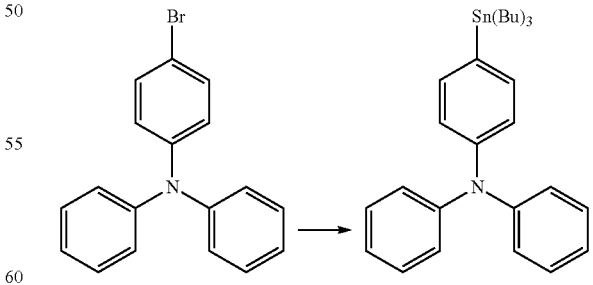

First, in an Ar gas atmosphere, in a 1-L three-necked flask, 4-bromotriphenylamine (25 g, 77 mmol) was dissolved in dehydrated THF (500 mL), and the resulting mixture was cooled to −78° C. Then, a 1.6 M n-BuLi hexane solution (52.5 mL, 84.5 mmol) was added dropwise thereto at an internal temperature of −60° C. or lower, followed by stirring as such for 30 minutes. Thereafter, tributyltin(IV) chloride (25.1 g, 77 mmol) was added dropwise thereto at an internal temperature of −60° C. or lower. After the dropwise addition, the temperature was raised to room temperature, and the mixture was stirred overnight.

Subsequently, NaF (4.20 g, 100 mmol) was dissolved in water (500 mL), and the reaction mixture was poured into the solution. Toluene (250 mL) was added thereto, followed by stirring for 1 hour, and thereafter, the organic layer was fractionated and washed again using water (250 mL×2). The obtained organic layer was subjected to a concentration operation under reduced pressure, whereby a target material was obtained (yield amount: 42 g).

Step 3

[Chem. 38]

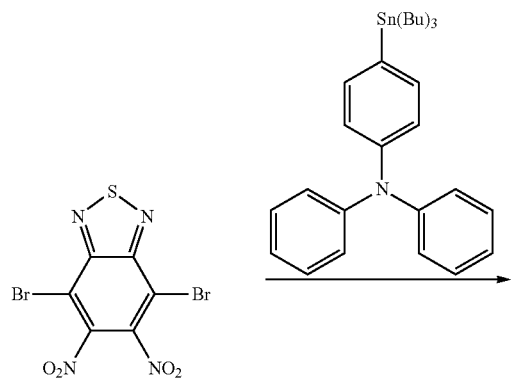

Step 4

[Chem. 39]

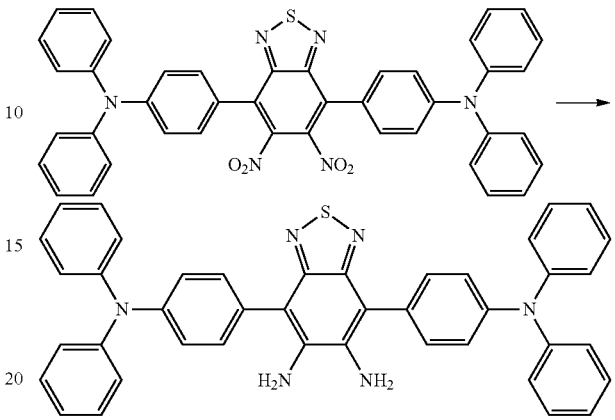

First, in an Ar gas atmosphere, to a 300-mL three-necked flask, acetic acid (200 mL) and Fe (10.2 g, 182 mmol) were added, and the internal temperature was raised to 65° C. Thereto, the dinitro compound (10.1 g, 14.2 mmol) obtained in the step 3 was added slowly in divided portions, and the temperature was raised to 80° C., followed by stirring as such for 3 hours.

Subsequently, the reaction mixture was cooled to room temperature, and then, poured into water (300 mL). Thereafter, the solid (including Fe) was filtered. An organic material was extracted from the solid using THF (300 mL), and concentration was performed under reduced pressure. Toluene (150 mL) was added to the obtained residue, and concentration was performed again under reduced pressure, whereby a target material was obtained (yield amount: 7.2 g, yield percentage: 78%).

Step 5

[Chem. 40]

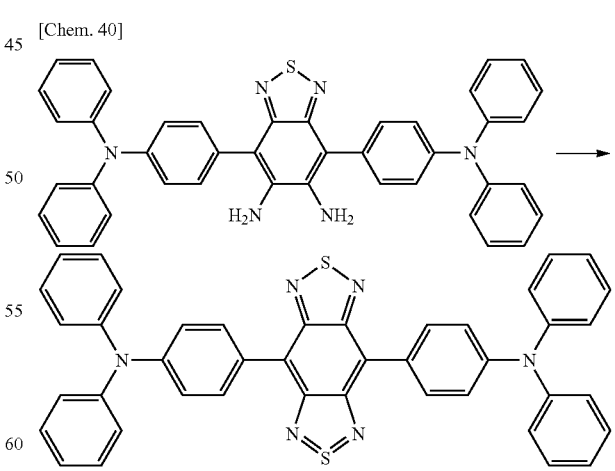

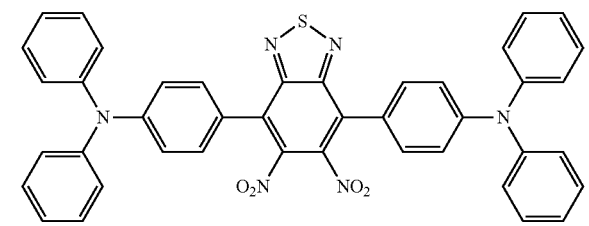

First, in an Ar gas atmosphere, in a 500-mL three-necked flask, a dibromo compound (7.5 g, 19.5 mmol) and a tin compound (the product in the step 2) (25.1 g, 50 mmol) were dissolved in dioxane (350 mL), and Pd(PPh3)4 (1.13 g, 0.975 mmol) was added thereto, and the internal temperature was raised to 95° C., and the resulting mixture was stirred overnight.

Subsequently, the reaction mixture was cooled to room temperature, and then, concentrated under reduced pressure. The obtained solid was washed with toluene, and thereafter recrystallization was performed using 400 mL of toluene, whereby a target material was obtained (yield amount: 7.8 g, yield percentage: 56%).

In an Ar gas atmosphere, to a 300-mL three-necked flask, the diamine compound (7.21 g, 11.0 mmol) obtained in the step 4 was dissolved in dehydrated pyridine (180 mL), and N-thionyl aniline (1.69 g, 12 mmol) and trimethylsilyl chloride (2.4 g, 22 mmol) were added thereto. Thereafter, the internal temperature was raised to 80° C., and the mixture was stirred overnight.

The reaction mixture was cooled to room temperature, and thereafter poured into water (200 mL). The deposited crystal was obtained by filtration, and the solid was washed with THF, whereby 3.8 g of the solid was obtained.

The solid was purified by silica gel chromatography (silica gel: 100 g, developing solvent: chlorobenzene).

Finally, purification was performed by a reprecipitation method using xylene, whereby a compound represented by the above chemical formula IRD-41 which is a target material was obtained (yield amount: 2.2 g, yield percentage: 30%).

2. Production of Light-Emitting Element

Example 1

<1> First, a transparent glass substrate having an average thickness of 0.5 mm was prepared. Subsequently, on this substrate, an ITO electrode (anode) having an average thickness of 100 nm was formed by a sputtering method.

Then, the substrate was subjected to ultrasonic cleaning while immersing the substrate in acetone and 2-propanol in this order, and thereafter subjected to an oxygen plasma treatment and an argon plasma treatment. Each of these plasma treatments was performed while heating the substrate to 70 to 90° C. at a plasma power of 100 W and a gas flow rate of 20 sccm for a treatment time of 5 sec.

<2> Subsequently, a compound represented by the above formula HIL-1 was deposited on the ITO electrode by a vacuum vapor deposition method, whereby a hole injection layer having an average thickness of 50 nm was formed.

<3> Subsequently, the constituent material of a light-emitting layer was deposited on the hole injection layer by a vacuum vapor deposition method, whereby a light-emitting layer having an average thickness of 25 nm was formed. As the constituent material of the light-emitting layer, a compound (thiadiazole-based compound 1) represented by the above formula IRD-15 was used as a light-emitting material (guest material), and a compound (tetracene-based material) represented by the above formula H-5 was used as a host material. Further, the content (doping concentration) of the light-emitting material (dopant) in the light-emitting layer was set to 2.0 wt %.

<4> Subsequently, a compound (azaindolizine-based compound) represented by the above formula ETL1-3 was deposited on the light-emitting layer by a vacuum vapor deposition method, whereby an electron transport layer (first electron transport layer) having an average thickness of 80 nm was formed.

<5> Subsequently, lithium fluoride (LiF) was deposited on the electron transport layer by a vacuum vapor deposition method, whereby an electron injection layer having an average thickness of 1 nm was formed.

<6> Subsequently, Al was deposited on the electron injection layer by a vacuum vapor deposition method, whereby a cathode having an average thickness of 100 nm constituted by Al was formed.

<7> Subsequently, a protective cover (sealing member) made of glass was placed thereon so as to cover the respective formed layers, and fixed and sealed with an epoxy resin.

By the above-mentioned steps, a bottom emission-type light-emitting element was produced.

Example 2

A bottom emission-type light-emitting element was produced in the same manner as in the above-mentioned Example 1 except that the content (doping concentration) of the light-emitting material (dopant) in the light-emitting layer was changed to 1.0 wt %.

Example 3

A bottom emission-type light-emitting element was produced in the same manner as in the above-mentioned Example 1 except that the content (doping concentration) of the light-emitting material (dopant) in the light-emitting layer was changed to 0.5 wt %.

Example 4

A bottom emission-type light-emitting element was produced in the same manner as in the above-mentioned Example 1 except that in the step <4>, a compound (anthracene-based compound) represented by the above formula ETL2-30 was deposited by a vacuum vapor deposition method, and then, a compound (azaindolizine-based compound) represented by the above formula ETL1-3 was deposited by a vacuum vapor deposition method, whereby an electron transport layer in which a second electron transport layer having an average thickness of 25 nm and a first electron transport layer having an average thickness of 5 nm were stacked was formed.

Example 5

A bottom emission-type light-emitting element was produced in the same manner as in the above-mentioned Example 1 except that in the step <4>, a compound (anthracene-based compound) represented by the above formula ETL2-30 was deposited by a vacuum vapor deposition method, and then, a compound (azaindolizine-based compound) represented by the above formula ETL1-3 was deposited by a vacuum vapor deposition method, whereby an electron transport layer in which a second electron transport layer having an average thickness of 20 nm and a first electron transport layer having an average thickness of 5 nm were stacked was formed.

Example 6

A bottom emission-type light-emitting element was produced in the same manner as in the above-mentioned Example 3 except that in the step <4>, a compound (anthracene-based compound) represented by the above formula ETL2-30 was deposited by a vacuum vapor deposition method, and then, a compound (azaindolizine-based compound) represented by the above formula ETL1-3 was deposited by a vacuum vapor deposition method, whereby an electron transport layer in which a second electron transport layer having an average thickness of 20 nm and a first electron transport layer having an average thickness of 5 nm were stacked was formed.

Example 7

A bottom emission-type light-emitting element was produced in the same manner as in the above-mentioned Example 1 except that in the step <2>, a hole injection layer having an average thickness of 30 nm was formed, and in the step <4>, a compound (anthracene-based compound) represented by the above formula ETL2-30 was deposited by a vacuum vapor deposition method, and then, a compound (azaindolizine-based compound) represented by the above formula ETL1-3 was deposited by a vacuum vapor deposition method, whereby an electron transport layer in which a second electron transport layer having an average thickness of 55 nm and a first electron transport layer having an average thickness of 5 nm were stacked was formed.

Example 8

<1> First, a transparent glass substrate having an average thickness of 0.5 mm was prepared. Subsequently, on this substrate, an ITO electrode (anode) having an average thickness of 10 nm was formed by a sputtering method.

Then, the substrate was subjected to ultrasonic cleaning while immersing the substrate in acetone and 2-propanol in this order, and thereafter subjected to an oxygen plasma treatment and an argon plasma treatment. Each of these plasma treatments was performed while heating the substrate to 70 to 90° C. at a plasma power of 100 W and a gas flow rate of 20 sccm for a treatment time of 5 sec.

<2> Subsequently, a compound represented by the above formula HIL-1 was deposited on the ITO electrode by a vacuum vapor deposition method, whereby a hole injection layer having an average thickness of 30 nm was formed.

<3> Subsequently, the constituent material of a light-emitting layer was deposited on the hole injection layer by a vacuum vapor deposition method, whereby a light-emitting layer having an average thickness of 25 nm was formed. As the constituent material of the light-emitting layer, a compound (thiadiazole-based compound 1) represented by the above formula IRD-15 was used as a light-emitting material (guest material), and a compound (tetracene-based material) represented by the above formula H-5 was used as a host material. Further, the content (doping concentration) of the light-emitting material (dopant) in the light-emitting layer was set to 1.0 wt %.

<4> Subsequently, on the light-emitting layer, a compound (anthracene-based compound) represented by the above formula ETL2-30 was deposited by a vacuum vapor deposition method, and then, a compound (azaindolizine-based compound) represented by the above formula ETL1-3 was deposited by a vacuum vapor deposition method, whereby an electron transport layer in which a second electron transport layer having an average thickness of 55 nm and a first electron transport layer having an average thickness of 5 nm were stacked was formed.

<5> Subsequently, lithium fluoride (LiF) was deposited on the electron transport layer by a vacuum vapor deposition method, whereby an electron injection layer having an average thickness of 1 nm was formed.

<6> Subsequently, Mg and Ag were deposited at a weight ratio of 1:20 on the electron injection layer by a vacuum vapor deposition method, whereby a cathode having an average thickness of 20 nm constituted by MgAg was formed.

<7> Subsequently, a protective cover (sealing member) made of glass was placed thereon so as to cover the respective formed layers, and fixed and sealed with an epoxy resin.

By the above-mentioned steps, a top emission-type light-emitting element was produced.

Example 9

A top emission-type light-emitting element was produced in the same manner as in the above-mentioned Example 8 except that in the step <1>, an ITO electrode having an average thickness of 20 nm was formed.

Example 10

A top emission-type light-emitting element was produced in the same manner as in the above-mentioned Example 8 except that in the step <1>, an ITO electrode having an average thickness of 30 nm was formed.

Example 11

A top emission-type light-emitting element was produced in the same manner as in the above-mentioned Example 8 except that in the step <1>, an ITO electrode having an average thickness of 70 nm was formed.

Example 12

<1> First, a transparent glass substrate having an average thickness of 0.5 mm was prepared. Subsequently, on this substrate, an ITO electrode (anode) having an average thickness of 100 nm was formed by a sputtering method.

Then, the substrate was subjected to ultrasonic cleaning while immersing the substrate in acetone and 2-propanol in this order, and thereafter subjected to an oxygen plasma treatment and an argon plasma treatment. Each of these plasma treatments was performed while heating the substrate to 70 to 90° C. at a plasma power of 100 W and a gas flow rate of 20 sccm for a treatment time of 5 sec.

<2> Subsequently, a compound represented by the above formula HIL-1 was deposited on the ITO electrode by a vacuum vapor deposition method, whereby a hole injection layer having an average thickness of 60 nm was formed.

<3> Subsequently, the constituent material of a light-emitting layer was deposited on the hole injection layer by a vacuum vapor deposition method, whereby a light-emitting layer having an average thickness of 25 nm was formed. As the constituent material of the light-emitting layer, a compound (thiadiazole-based compound 2) represented by the above formula IRD-24 was used as a light-emitting material (guest material), and a compound (tetracene-based material) represented by the above formula H-5 was used as a host material. Further, the content (doping concentration) of the light-emitting material (dopant) in the light-emitting layer was set to 4.0 wt %.

<4> Subsequently, a compound (azaindolizine-based compound) represented by the above formula ETL1-3 was deposited on the light-emitting layer by a vacuum vapor deposition method, whereby an electron transport layer (first electron transport layer) having an average thickness of 90 nm was formed.

<5> Subsequently, lithium fluoride (LiF) was deposited on the electron transport layer by a vacuum vapor deposition method, whereby an electron injection layer having an average thickness of 1 nm was formed.

<6> Subsequently, Al was deposited on the electron injection layer by a vacuum vapor deposition method, whereby a cathode having an average thickness of 100 nm constituted by Al was formed.

<7> Subsequently, a protective cover (sealing member) made of glass was placed thereon so as to cover the respective formed layers, and fixed and sealed with an epoxy resin.

By the above-mentioned steps, a bottom emission-type light-emitting element was produced.

Example 13

A bottom emission-type light-emitting element was produced in the same manner as in the above-mentioned Example 12 except that the content (doping concentration) of the light-emitting material (dopant) in the light-emitting layer was changed to 2.0 wt %.

Example 14

A bottom emission-type light-emitting element was produced in the same manner as in the above-mentioned Example 12 except that the content (doping concentration) of the light-emitting material (dopant) in the light-emitting layer was changed to 1.0 wt %.

Example 15

A bottom emission-type light-emitting element was produced in the same manner as in the above-mentioned Example 14 except that in the step <3>, a light-emitting layer having an average thickness of 40 nm was formed, and in the step <4>, an electron transport layer (first electron transport layer) having an average thickness of 75 nm was formed.

Example 16

A bottom emission-type light-emitting element was produced in the same manner as in the above-mentioned Example 14 except that in the step <3>, a light-emitting layer having an average thickness of 60 nm was formed, and in the step <4>, an electron transport layer (first electron transport layer) having an average thickness of 55 nm was formed.

Example 17

<1> First, a transparent glass substrate having an average thickness of 0.5 mm was prepared. Subsequently, on this substrate, an ITO electrode (anode) having an average thickness of 18 nm was formed by a sputtering method.

Then, the substrate was subjected to ultrasonic cleaning while immersing the substrate in acetone and 2-propanol in this order, and thereafter subjected to an oxygen plasma treatment and an argon plasma treatment. Each of these plasma treatments was performed while heating the substrate to 70 to 90° C. at a plasma power of 100 W and a gas flow rate of 20 sccm for a treatment time of 5 sec.

<2> Subsequently, a compound represented by the above formula HIL-1 was deposited on the ITO electrode by a vacuum vapor deposition method, whereby a hole injection layer having an average thickness of 70 nm was formed.

<3> Subsequently, the constituent material of a light-emitting layer was deposited on the hole injection layer by a vacuum vapor deposition method, whereby a light-emitting layer having an average thickness of 25 nm was formed. As the constituent material of the light-emitting layer, a compound (thiadiazole-based compound 2) represented by the above formula IRD-24 was used as a light-emitting material (guest material), and a compound (tetracene-based material) represented by the above formula H-5 was used as a host material. Further, the content (doping concentration) of the light-emitting material (dopant) in the light-emitting layer was set to 2.0 wt %.

<4> Subsequently, a compound (azaindolizine-based compound) represented by the above formula ETL1-3 was deposited on the light-emitting layer by a vacuum vapor deposition method, whereby an electron transport layer (first electron transport layer) having an average thickness of 70 nm was formed.

<5> Subsequently, lithium fluoride (LiF) was deposited on the electron transport layer by a vacuum vapor deposition method, whereby an electron injection layer having an average thickness of 1 nm was formed.

<6> Subsequently, Mg and Ag were deposited at a weight ratio of 1:20 on the electron injection layer by a vacuum vapor deposition method, whereby a cathode having an average thickness of 20 nm constituted by MgAg was formed.

<7> Subsequently, a protective cover (sealing member) made of glass was placed thereon so as to cover the respective formed layers, and fixed and sealed with an epoxy resin.

By the above-mentioned steps, a top emission-type light-emitting element was produced.

Example 18

A top emission-type light-emitting element was produced in the same manner as in the above-mentioned Example 17 except that in the step <1>, an ITO electrode having an average thickness of 25 nm was formed.

Example 19

A top emission-type light-emitting element was produced in the same manner as in the above-mentioned Example 17 except that in the step <1>, an ITO electrode having an average thickness of 30 nm was formed.

Example 20

<1> First, a transparent glass substrate having an average thickness of 0.5 mm was prepared. Subsequently, on this substrate, an ITO electrode (anode) having an average thickness of 100 nm was formed by a sputtering method.

Then, the substrate was subjected to ultrasonic cleaning while immersing the substrate in acetone and 2-propanol in this order, and thereafter subjected to an oxygen plasma treatment and an argon plasma treatment. Each of these plasma treatments was performed while heating the substrate to 70 to 90° C. at a plasma power of 100 W and a gas flow rate of 20 sccm for a treatment time of 5 sec.

<2> Subsequently, a compound represented by the above formula HIL-1 was deposited on the ITO electrode by a vacuum vapor deposition method, whereby a hole injection layer having an average thickness of 50 nm was formed.

<3> Subsequently, the constituent material of a light-emitting layer was deposited on the hole injection layer by a vacuum vapor deposition method, whereby a light-emitting layer having an average thickness of 25 nm was formed. As the constituent material of the light-emitting layer, a compound (pyrromethene-based boron complex) represented by the above formula IRD-31 was used as a light-emitting material (guest material), and a compound (tetracene-based material) represented by the above formula H-5 was used as a host material. Further, the content (doping concentration) of the light-emitting material (dopant) in the light-emitting layer was set to 1.0 wt %.

<4> Subsequently, a compound (azaindolizine-based compound) represented by the above formula ETL1-3 was deposited on the light-emitting layer by a vacuum vapor deposition method, whereby an electron transport layer (first electron transport layer) having an average thickness of 80 nm was formed.

<5> Subsequently, lithium fluoride (LiF) was deposited on the electron transport layer by a vacuum vapor deposition method, whereby an electron injection layer having an average thickness of 1 nm was formed.

<6> Subsequently, Al was deposited on the electron injection layer by a vacuum vapor deposition method, whereby a cathode having an average thickness of 1000 nm constituted by Al was formed.

<7> Subsequently, a protective cover (sealing member) made of glass was placed thereon so as to cover the respective formed layers, and fixed and sealed with an epoxy resin.

By the above-mentioned steps, a bottom emission-type light-emitting element was produced.

Example 21

A bottom emission-type light-emitting element was produced in the same manner as in the above-mentioned Example 20 except that the content (doping concentration) of the light-emitting material (dopant) in the light-emitting layer was changed to 0.5 wt %.

Example 22

A bottom emission-type light-emitting element was produced in the same manner as in the above-mentioned Example 20 except that the content (doping concentration) of the light-emitting material (dopant) in the light-emitting layer was changed to 0.25 wt %.

Example 23

<1> First, a transparent glass substrate having an average thickness of 0.5 mm was prepared. Subsequently, on this substrate, an ITO electrode (anode) having an average thickness of 100 nm was formed by a sputtering method.

Then, the substrate was subjected to ultrasonic cleaning while immersing the substrate in acetone and 2-propanol in this order, and thereafter subjected to an oxygen plasma treatment and an argon plasma treatment. Each of these plasma treatments was performed while heating the substrate to 70 to 90° C. at a plasma power of 100 W and a gas flow rate of 20 sccm for a treatment time of 5 sec.

<2> Subsequently, a compound represented by the above formula HIL-1 was deposited on the ITO electrode by a vacuum vapor deposition method, whereby a hole injection layer having an average thickness of 70 nm was formed.

<3> Subsequently, the constituent material of a light-emitting layer was deposited on the hole injection layer by a vacuum vapor deposition method, whereby a light-emitting layer having an average thickness of 25 nm was formed. As the constituent material of the light-emitting layer, a compound (benzo-bis-thiadiazole-based compound) represented by the above formula IRD-41 was used as a light-emitting material (guest material), and a compound (tetracene-based material) represented by the above formula H-5 was used as a host material. Further, the content (doping concentration) of the light-emitting material (dopant) in the light-emitting layer was set to 2.0 wt %.

<4> Subsequently, a compound (azaindolizine-based compound) represented by the above formula ETL1-3 was deposited on the light-emitting layer by a vacuum vapor deposition method, whereby an electron transport layer (first electron transport layer) having an average thickness of 95 nm was formed.

<5> Subsequently, lithium fluoride (LiF) was deposited on the electron transport layer by a vacuum vapor deposition method, whereby an electron injection layer having an average thickness of 1 nm was formed.

<6> Subsequently, Al was deposited on the electron injection layer by a vacuum vapor deposition method, whereby a cathode having an average thickness of 100 nm constituted by Al was formed.

<7> Subsequently, a protective cover (sealing member) made of glass was placed thereon so as to cover the respective formed layers, and fixed and sealed with an epoxy resin.

By the above-mentioned steps, a bottom emission-type light-emitting element was produced.

Example 24

A bottom emission-type light-emitting element was produced in the same manner as in the above-mentioned Example 23 except that the content (doping concentration) of the light-emitting material (dopant) in the light-emitting layer was changed to 1.0 wt %.

Example 25

A bottom emission-type light-emitting element was produced in the same manner as in the above-mentioned Example 23 except that the content (doping concentration) of the light-emitting material (dopant) in the light-emitting layer was changed to 0.5 wt %.

Example 26

A bottom emission-type light-emitting element was produced in the same manner as in the above-mentioned Example 23 except that in the step <4>, a compound (anthracene-based compound) represented by the above formula ETL2-30 was deposited by a vacuum vapor deposition method, and then, a compound (azaindolizine-based compound) represented by the above formula ETL1-3 was deposited by a vacuum vapor deposition method, whereby an electron transport layer in which a second electron transport layer having an average thickness of 90 nm and a first electron transport layer having an average thickness of 5 nm were stacked was formed.

3. Evaluation

With respect to the light-emitting elements of the respective Examples, a constant current of 50 mA/cm$^2$, 100 mA/cm$^2$, or 300 mA/cm$^2$ was allowed to flow through each of the light-emitting elements using a constant current power supply (KEITHLEY 2400, manufactured by TOYO Corporation), and the emission spectrum of each of the light-emitting elements was measured as an emission energy amount (mW/sr/m$^2$) using a miniature fiber optic spectrometer (CS-1000, manufactured by Konica Minolta, Inc.).

Then, each of the emission spectra at 50 mA/cm$^2$, 100 mA/cm$^2$, and 300 mA/cm$^2$ measured for the light-emitting elements of the respective Examples was converted from an emission energy amount (mW/sr/m$^2$) into an emission luminance (cd/m$^2$), and from the emission spectrum converted into the emission luminance (cd/m$^2$), an emission luminance (cd/m$^2$) in visible light (400 to 600 nm) was determined.

The results are shown in Table 1.

[Table 1]

TABLE 1

| | | Example | | Concentration (%) | Current density | | |
|---|---|---|---|---|---|---|---|
| | | | | | 50 mA/cm$^2$ Measured luminance (cd/m$^2$) | 100 mA/cm$^2$ Measured luminance (cd/m$^2$) | 300 mA/cm$^2$ Measured luminance (cd/m$^2$) |
| Light-emitting material IRD-15 760 nm peak | Bottom emission | 1 | EIR-01 standard (basis) | 2 | 11 | 22 | 76 |
| | | 2 | Study of low concentration | 1 | 23 | 48 | 155 |
| | | 3 | Study of low concentration | 0.5 | 67 | 136 | 414 |
| | | 4 | Insertion of BH layer | 2 | 9 | 21 | 72 |
| | | 5 | Insertion of BH layer | 1 | 16 | 35 | 124 |
| | | 6 | Insertion of BH layer | 0.5 | 41 | 87 | 279 |
| | | 7 | Change in film thickness of HT and BH | 1 | 5 | 11 | 37 |
| | Top emission | 8 | ITO = 10 nm | 1 | 1.8 | 4.0 | 12 |
| | | 9 | ITO = 20 | 1 | 1.0 | 2.3 | 8 |
| | | 10 | ITO = 30 | 1 | 0.8 | 1.6 | 6 |
| | | 11 | ITO = 75 | 1 | 2.6 | 6.0 | 20 |
| Light-emitting material IRD-24 830 nm peak | Bottom emission | 12 | EIR-04 standard (basis) | 4 | 2.6 | 5.5 | 19 |
| | | 13 | Study of low concentration | 2 | 10.5 | 21.2 | 69 |
| | | 14 | Study of low concentration | 1 | 21.6 | 43.4 | 135 |
| | | 15 | Change in film thickness of light-emitting layer | 1 | 24.2 | 49.0 | 153 |
| | | 16 | Change in film thickness of light-emitting layer | 1 | 36.1 | 71.0 | 210 |
| | Top emission | 17 | ITO = 18 nm | 2 | 1.0 | 2.1 | 7 |
| | | 18 | ITO = 25 | 2 | 1.4 | 2.8 | 9 |
| | | 19 | ITO = 30 | 2 | 1.5 | 3.1 | 10 |
| Light-emitting material IRD-31 770 nm peak | Bottom emission | 20 | EIR-06 standard (basis) | 1 | 2 | 5 | 16 |
| | | 21 | Study of low concentration | 0.5 | 15 | 33 | 108 |
| | | 22 | Study of low concentration | 0.25 | 25 | 54 | 183 |
| Light-emitting material IRD-41 870 nm peak | Bottom emission | 23 | EIR-02 standard (basis) | 2 | 1.0 | 2.2 | 8.3 |
| | | 24 | Study of low concentration | 1 | 4 | 9 | 31 |
| | | 25 | Study of low concentration | 0.5 | 7 | 15 | 50 |
| | | 26 | Insertion of BH layer | 1 | 1.5 | 3.3 | 12.2 |

| | | Example | Layer configuration of light-emitting element |
|---|---|---|---|
| Light-emitting material IRD-15 760 nm peak | Bottom emission | 1 | HIL-1(50)/2%_IRD-15:H-5(25)/ETL1-3(80)/LiF(1)/Al(100) |
| | | 2 | HIL-1(50)/1%_IRD-15:H-5(25)/ETL1-3(80)/LiF(1)/Al(100) |
| | | 3 | HIL-1(50)/0.5%_IRD-15:H-5(25)/ETL1-3(80)/LiF(1)/Al(100) |
| | | 4 | HIL-1(60)/2%_IRD-15:H-5(25)/ETL2-30(25)/ETL1-3(5)/LiF(1)/Al(100) |
| | | 5 | HIL-1(60)/1%_IRD-15:H-5(25)/ETL2-30(20)/ETL1-3(5)/LiF(1)/Al(100) |
| | | 6 | HIL-1(60)/0.5%_IRD-15:H-5(25)/ETL2-30(20)/ETL1-3(5)/LiF(1)/Al(100) |
| | | 7 | HIL-1(30)/2%_IRD-15:H-5(25)/ETL2-30(55)/ETL1-3(5)/LiF(1)/Al(100) |
| | Top emission | 8 | HIL-1(30)/1%_IRD-15:H-5(25)/ETL2-30(55)/ETL1-3(5)/LiF(1)/MgAg(1:20,20) |
| | | 9 | |
| | | 10 | |
| | | 11 | |
| Light-emitting material IRD-24 830 nm peak | Bottom emission | 12 | HIL-1(60)/4%_IRD-24:H-5(25)/ETL1-3(90)/LiF(1)/Al(100) |
| | | 13 | HIL-1(60)/2%_IRD-24:H-5(25)/ETL1-3(90)/LiF(1)/Al(100) |
| | | 14 | HIL-1(60)/1%_IRD-24:H-5(25)/ETL1-3(90)/LiF(1)/Al(100) |
| | | 15 | HIL-1(60)/1%_IRD-24:H-5(40)/ETL1-3(75)/LiF(1)/Al(100) |
| | | 16 | HIL-1(60)/1%_IRD-24:H-5(60)/ETL1-3(55)/LiF(1)/Al(100) |
| | Top emission | 17 | HIL-1(70)/2%_IRD-24:H-5(25)/ETL1-3(70)/LiF(1)/MgAg(1:20)(20) |
| | | 18 | |
| | | 19 | |
| Light-emitting material IRD-31 770 nm peak | Bottom emission | 20 | HIL-1(50)/1%_IRD-31:H-5(25)/ETL1-3(80)/LiF(1)/Al(1000) |
| | | 21 | HIL-1(50)/0.5%_IRD-31:H-5(25)/ETL1-3(80)/LiF(1)/Al(1000) |
| | | 22 | HIL-1(50)/0.25%_IRD-31:H-5(25)/ETL1-3(80)/LiF(1)/Al(1000) |
| Light-emitting material IRD-41 870 nm peak | Bottom emission | 23 | HIL-1(70)/2%_IRD-41:H-5(25)/ETL1-3(95)/LiF(1)/Al(100) |
| | | 24 | HIL-1(70)/1%_IRD-41:H-5(25)/ETL1-3(95)/LiF(1)/Al(100) |
| | | 25 | HIL-1(70)/0.5%_IRD-41:H-5(25)/ETL1-3(95)/LiF(1)/Al(100) |
| | | 26 | HIL-1(70)/1%_IRD-41:H-5(25)/ETL2-30(90)/ETL1-3(5)/LiF(1)/Al(100) |

As apparent from Table 1, it was found that each of the light-emitting elements of the respective Examples can emit visible light with a luminance of 5 cd/m$^2$ or more when a constant current of 300 mA/cm$^2$ was allowed to flow.

Further, it was revealed that as shown in Examples 2, 3, 13, 14, 21, 22, 24, and 25, by setting the concentration of the light-emitting material in the light-emitting layer to a low concentration, the improvement of the emission luminance is achieved. In addition, it was revealed that as shown in Examples 4 to 7, 15, 16, and 26, the improvement of the emission luminance is achieved also by changing the film thickness of the light-emitting layer and the hole injection layer or by changing the layer configuration of the electron transport layer. Further, it was found that as shown in Examples 8 to 11, and 17 to 19, the invention not only can be applied to a bottom emission type, but also can be applied to a top emission type.

Then, the emission spectra at 300 mA/cm² measured for the light-emitting elements of the respective Examples are shown in FIGS. 5 to 17. Incidentally, in each drawing, the graph on the left is an emission spectrum based on the emission energy amount (W/sr/m²), and the graph on the right is an emission spectrum based on the emission luminance (cd/m²).

Then, from the emission spectra at 300 mA/cm² measured for the light-emitting elements of the respective Examples, the emission luminance (cd/m²) in visible light (400 to 600 nm), the maximum value of the emission energy amount (W/sr/m²), and the maximum value of the emission luminance (cd/m²) were determined (see Table 2-1).

Further, from these results, each of the maximum value of the emission energy amount (W/sr/m²), and the maximum value of the emission luminance (cd/m²), which are required for making the light-emitting element to have an emission luminance of 5 cd/m² or more, 10 cd/m² or more, and further, 30 cd/m² or more was obtained by determining the value of mean (Ave.)+3 standard deviation (σ) (see Tables 2-2 to 2-4).

The results are shown in Table 2.

[Table 2]

TABLE 2-1

|  |  |  | Example |  |  |  |  |  |  |
|---|---|---|---|---|---|---|---|---|---|
|  |  |  | 1 | 2 | 3 | 4 | 5 | 6 | 7 |
|  |  | Measured luminance | 75.8 | 155.2 | 413.4 | 72.2 | 124.3 | 279.0 | 37.2 |
| W/sr/m² | Peak Max | 400-600 nm | 0.003416 | 0.004511 | 0.01032 | 0.001562 | 0.003001 | 0.007211 | 0.000552 |
| cd/m² | Peak Max | 400-800 nm | 0.754066 | 1.666982 | 5.058914 | 0.757461 | 1.456239 | 3.515994 | 0.296012 |
|  |  |  | Example |  |  |  |  |  |  |
|  |  |  | 8 | 9 | 10 | 11 | 12 | 13 | 14 |
|  |  | Measured luminance | 12.4 | 7.5 | 5.7 | 20.5 | 19.3 | 68.5 | 134.8 |
| W/sr/m2 | Peak Max | 400-600 nm | 0.000191 | 0.000184 | 0.000239 | 0.000739 | 0.000522 | 0.0001738 | 0.003251 |
| cd/m2 | Peak Max | 400-800 nm | 0.147075 | 0.077316 | 0.098147 | 0.462286 | 0.250251 | 0.907024 | 1.894642 |
|  |  |  | Example |  |  |  |  |  |  |
|  |  |  | 15 | 16 | 17 | 18 | 19 | 20 | 21 |
|  |  | Measured luminance | 153.3 | 210.2 | 6.6 | 8.9 | 9.6 | 16.4 | 108.0 |
| W/sr/m² | Peak Max | 400-600 nm | 0.004032 | 0.00626 | 0.000304 | 0.000284 | 0.000342 | 0.000368 | 0.002506 |
| cd/m² | Peak Max | 400-800 nm | 2.195845 | 3.278705 | 0.16426 | 0.162788 | 0.179024 | 0.214804 | 1.472548 |
|  |  |  | Example |  |  |  |  |  |
|  |  |  | 22 | 23 | 24 | 25 | 26 |
|  |  | Measured luminance | 183.1 | 8.3 | 30.7 | 49.5 | 12.1 |
| W/sr/m² | Peak Max | 400-600 nm | 0.004575 | 0.000232 | 0.000756 | 0.001326 | 0.000473 |
| cd/m² | Peak Max | 400-800 nm | 2.625452 | 0.117681 | 0.449953 | 0.727836 | 0.176692 |

TABLE 2-2

5 cd/m² equivalent: A peak value in each of the graphs on the left and right when the luminance is 5 cd/m²

|  |  |  | Ave. | σ | Ave + 3σ | Example |  |  |  |  |  |
|---|---|---|---|---|---|---|---|---|---|---|---|
|  |  |  |  |  |  | 1 | 2 | 3 | 4 | 5 | 6 |
|  |  | 5 cd/m² equivalent |  |  |  | 5.0 | 5.0 | 5.0 | 5.0 | 5.0 | 5.0 |
| W/sr/m² | Peak Max | 400-600 nm | 1.421E−04 | 3.979E−05 | 2.614E−04 | 2.3E−04 | 1.5E−04 | 1.2E−04 | 1.1E−04 | 1.2E−04 | 1.3E−04 |
| cd/m² | Peak Max | 400-800 nm | 7.095E−02 | 1.833E−02 | 1.274E−01 | 5.0E−02 | 5.4E−02 | 6.1E−02 | 5.2E−02 | 5.9E−02 | 6.3E−02 |
|  |  |  | Ave. | σ | Ave + 3σ | Example |  |  |  |  |  |
|  |  |  |  |  |  | 7 | 8 | 9 | 10 | 11 | 12 |
|  |  | 5 cd/m² equivalent |  |  |  | 5.0 | 5.0 | 5.0 | 5.0 | 5.0 | 5.0 |
| W/sr/m² | Peak Max | 400-600 nm | 1.421E−04 | 3.979E−05 | 2.614E−04 | 7.4E−04 | 7.7E−05 | 1.2E−04 | 2.1E−04 | 1.8E−04 | 1.4E−04 |
| cd/m² | Peak Max | 400-800 nm | 7.095E−02 | 1.833E−02 | 1.274E−01 | 4.0E−02 | 5.9E−02 | 5.2E−02 | 8.6E−02 | 1.1E−01 | 6.5E−02 |

TABLE 2-2-continued 5 cd/m² equivalent: A peak value in each of the graphs on the left and right when the luminance is 5 cd/m²

|  |  |  | Ave. | σ | Ave + 3σ | Example | | | | | |
|---|---|---|---|---|---|---|---|---|---|---|---|
|  |  |  |  |  |  | 13 | 14 | 15 | 16 | 17 | 18 |
|  |  | 5 cd/m² equivalent |  |  |  | 5.0 | 5.0 | 5.0 | 5.0 | 5.0 | 5.0 |
| W/sr/m² | Peak Max | 400-600 nm | 1.421E−04 | 3.979E−05 | 2.614E−04 | 1.3E−04 | 1.2E−04 | 1.3E−04 | 1.5E−04 | 2.3E−04 | 1.6E−04 |
| cd/m² | Peak Max | 400-800 nm | 7.095E−02 | 1.833E−02 | 1.274E−01 | 6.6E−02 | 7.0E−02 | 7.2E−02 | 7.8E−02 | 1.2E−01 | 9.2E−02 |

|  |  |  | Ave. | σ | Ave + 3σ | Example | | | | | |
|---|---|---|---|---|---|---|---|---|---|---|---|
|  |  |  |  |  |  | 19 | 20 | 21 | 22 | 23 | 24 |
|  |  | 5 cd/m² equivalent |  |  |  | 5.0 | 5.0 | 5.0 | 5.0 | 5.0 | 5.0 |
| W/sr/m² | Peak Max | 400-600 nm | 1.421E−04 | 3.979E−05 | 2.614E−04 | 1.8E−04 | 1.1E−04 | 1.2E−04 | 1.2E−04 | 1.4E−04 | 1.2E−04 |
| cd/m² | Peak Max | 400-800 nm | 7.095E−02 | 1.833E−02 | 1.274E−01 | 9.4E−02 | 6.5E−02 | 6.8E−02 | 7.2E−02 | 7.1E−02 | 7.3E−02 |

|  |  |  | Ave. | σ | Ave + 3σ | Example | |
|---|---|---|---|---|---|---|---|
|  |  |  |  |  |  | 25 | 26 |
|  |  | 5 cd/m² equivalent |  |  |  | 5.0 | 5.0 |
| W/sr/m² | Peak Max | 400-600 nm | 1.421E−04 | 3.979E−05 | 2.614E−04 | 1.3E−04 | 1.9E−04 |
| cd/m² | Peak Max | 400-800 nm | 7.095E−02 | 1.833E−02 | 1.274E−01 | 7.3E−02 | 7.3E−02 |

TABLE 2-3

10 cd/m² equivalent: A peak value in each of the graphs on the left and right when the luminance is 10 cd/m²

|  |  |  | Ave. | σ | Ave + 3σ | Example | | | | | |
|---|---|---|---|---|---|---|---|---|---|---|---|
|  |  |  |  |  |  | 1 | 2 | 3 | 4 | 5 | 6 |
|  |  | 10 cd/m² equivalent |  |  |  | 10.0 | 10.0 | 10.0 | 10.0 | 10.0 | 10.0 |
| W/sr/m² | Peak Max | 400-600 nm | 2.841E−04 | 7.958E−05 | 5.229E−04 | 4.5E−04 | 2.9E−04 | 2.5E−04 | 2.2E−04 | 2.4E−04 | 2.6E−04 |
| cd/m² | Peak Max | 400-800 nm | 1.419E−01 | 3.766E−02 | 2.549E−01 | 9.9E−02 | 1.1E−01 | 1.2E−01 | 1.0E−01 | 1.2E−01 | 1.3E−01 |

|  |  |  | Ave. | σ | Ave + 3σ | Example | | | | | |
|---|---|---|---|---|---|---|---|---|---|---|---|
|  |  |  |  |  |  | 7 | 8 | 9 | 10 | 11 | 12 |
|  |  | 10 cd/m² equivalent |  |  |  | 10.0 | 10.0 | 10.0 | 10.0 | 10.0 | 10.0 |
| W/sr/m² | Peak Max | 400-600 nm | 2.841E−04 | 7.958E−05 | 5.229E−04 | 1.5E−04 | 1.5E−04 | 2.5E−04 | 4.2E−04 | 3.6E−04 | 2.7E−04 |
| cd/m² | Peak Max | 400-800 nm | 1.419E−01 | 3.766E−02 | 2.549E−01 | 7.9E−02 | 1.2E−01 | 1.0E−01 | 1.7E−01 | 2.3E−01 | 1.3E−01 |

|  |  |  | Ave. | σ | Ave + 3σ | Example | | | | | |
|---|---|---|---|---|---|---|---|---|---|---|---|
|  |  |  |  |  |  | 13 | 14 | 15 | 16 | 17 | 18 |
|  |  | 10 cd/m² equivalent |  |  |  | 10.0 | 10.0 | 10.0 | 10.0 | 10.0 | 10.0 |
| W/sr/m² | Peak Max | 400-600 nm | 2.841E−04 | 7.958E−05 | 5.229E−04 | 2.5E−04 | 2.4E−04 | 2.6E−04 | 3.0E−04 | 4.6E−04 | 3.2E−04 |
| cd/m² | Peak Max | 400-800 nm | 1.419E−01 | 3.766E−02 | 2.549E−01 | 1.3E−01 | 1.4E−01 | 1.4E−01 | 1.6E−01 | 2.5E−01 | 1.8E−01 |

|  |  |  | Ave. | σ | Ave + 3σ | Example | | | | | |
|---|---|---|---|---|---|---|---|---|---|---|---|
|  |  |  |  |  |  | 19 | 20 | 21 | 22 | 23 | 24 |
|  |  | 10 cd/m² equivalent |  |  |  | 10.0 | 10.0 | 10.0 | 10.0 | 10.0 | 10.0 |
| W/sr/m² | Peak Max | 400-600 nm | 2.841E−04 | 7.958E−05 | 5.229E−04 | 3.6E−04 | 2.2E−04 | 2.3E−04 | 2.5E−04 | 2.8E−04 | 2.5E−04 |
| cd/m² | Peak Max | 400-800 nm | 1.419E−01 | 3.766E−02 | 2.549E−01 | 1.9E−01 | 1.3E−01 | 1.4E−01 | 1.4E−01 | 1.4E−01 | 1.5E−01 |

TABLE 2-3-continued 10 cd/m² equivalent: A peak value in each of the graphs on the left and right when the luminance is 10 cd/m²

|  |  |  | Ave. | σ | Ave + 3σ | Example 25 | Example 26 |
|---|---|---|---|---|---|---|---|
|  |  | 10 cd/m² equivalent |  |  |  | 10.0 | 10.0 |
| W/sr/m² | Peak Max | 400-600 nm | 2.841E−04 | 7.958E−05 | 5.229E−04 | 2.7E−04 | 3.9E−04 |
| cd/m² | Peak Max | 400-800 nm | 1.419E−01 | 3.766E−02 | 2.549E−01 | 1.5E−01 | 1.5E−01 |

TABLE 2-4

30 cd/m² equivalent: A peak value in each of the graphs on the left and right when the luminance is 30 cd/m²

|  |  |  | Ave. | σ | Ave + 3σ | Ex. 1 | Ex. 2 | Ex. 3 | Ex. 4 | Ex. 5 | Ex. 6 |
|---|---|---|---|---|---|---|---|---|---|---|---|
|  |  | 30 cd/m² equivalent |  |  |  | 30.0 | 30.0 | 30.0 | 30.0 | 30.0 | 30.0 |
| W/sr/m² | Peak Max | 400-600 nm | 8.524E−04 | 2.387E−04 | 1.569E−03 | 1.4E−03 | 8.7E−04 | 7.5E−04 | 6.5E−04 | 7.2E−04 | 7.8E−04 |
| cd/m² | Peak Max | 400-800 nm | 4.257E−01 | 1.130E−01 | 7.646E−01 | 3.0E−01 | 3.2E−01 | 3.7E−01 | 3.1E−01 | 3.5E−01 | 3.8E−01 |

|  |  |  | Ave. | σ | Ave + 3σ | Ex. 7 | Ex. 8 | Ex. 9 | Ex. 10 | Ex. 11 | Ex. 12 |
|---|---|---|---|---|---|---|---|---|---|---|---|
|  |  | 30 cd/m² equivalent |  |  |  | 30.0 | 30.0 | 30.0 | 30.0 | 30.0 | 30.0 |
| W/sr/m² | Peak Max | 400-600 nm | 8.524E−04 | 2.387E−04 | 1.569E−03 | 4.4E−04 | 4.6E−04 | 7.4E−04 | 1.3E−03 | 1.1E−03 | 8.1E−04 |
| cd/m² | Peak Max | 400-800 nm | 4.257E−01 | 1.130E−01 | 7.646E−01 | 2.4E−01 | 3.6E−01 | 3.1E−01 | 5.1E−01 | 6.8E−01 | 3.9E−01 |

|  |  |  | Ave. | σ | Ave + 3σ | Ex. 13 | Ex. 14 | Ex. 15 | Ex. 16 | Ex. 17 | Ex. 18 |
|---|---|---|---|---|---|---|---|---|---|---|---|
|  |  | 30 cd/m² equivalent |  |  |  | 30.0 | 30.0 | 30.0 | 30.0 | 30.0 | 30.0 |
| W/sr/m² | Peak Max | 400-600 nm | 8.524E−04 | 2.387E−04 | 1.569E−03 | 7.6E−04 | 7.2E−04 | 7.9E−04 | 8.9E−04 | 1.4E−03 | 9.6E−04 |
| cd/m² | Peak Max | 400-800 nm | 4.257E−01 | 1.130E−01 | 7.646E−01 | 4.0E−01 | 4.2E−01 | 4.3E−01 | 4.7E−01 | 7.5E−01 | 5.5E−01 |

|  |  |  | Ave. | σ | Ave + 3σ | Ex. 19 | Ex. 20 | Ex. 21 | Ex. 22 | Ex. 23 | Ex. 24 |
|---|---|---|---|---|---|---|---|---|---|---|---|
|  |  | 30 cd/m² equivalent |  |  |  | 30.0 | 30.0 | 30.0 | 30.0 | 30.0 | 30.0 |
| W/sr/m² | Peak Max | 400-600 nm | 8.524E−04 | 2.387E−04 | 1.569E−03 | 1.1E−03 | 6.7E−04 | 7.0E−04 | 7.5E−04 | 8.4E−04 | 7.4E−04 |
| cd/m² | Peak Max | 400-800 nm | 4.257E−01 | 1.130E−01 | 7.646E−01 | 5.6E−01 | 3.9E−01 | 4.1E−01 | 4.3E−01 | 4.2E−01 | 4.4E−01 |

|  |  |  | Ave. | σ | Ave + 3σ | Ex. 25 | Ex. 26 |
|---|---|---|---|---|---|---|---|
|  |  | 30 cd/m² equivalent |  |  |  | 30.0 | 30.0 |
| W/sr/m² | Peak Max | 400-600 nm | 8.524E−04 | 2.387E−04 | 1.569E−03 | 8.0E−04 | 1.2E−03 |
| cd/m² | Peak Max | 400-800 nm | 4.257E−01 | 1.130E−01 | 7.646E−01 | 4.4E−01 | 4.4E−01 |

As apparent from Table 2, it was found that in order to make the light-emitting element to have an emission luminance of 5 cd/m² or more, the maximum value of the emission energy amount (W/sr/m²) and the maximum value of the emission luminance (cd/m²) need to be 2.614E-04 (W/sr/m²) or more and 1.274E-01 (cd/m²) or more, respectively, and further, in order to make the light-emitting element to have an emission luminance of 10 cd/m² or more, the maximum value of the emission energy amount (W/sr/m²) and the maximum value of the emission luminance (cd/m²) need to be 5.229E-04 (W/sr/m²) or more and 2.549E-01 (cd/m²) or more, respectively, and still further, in order to make the light-emitting element to have an emission luminance of 30 cd/m² or more, the maximum value of the emission energy amount (W/sr/m²) and the maximum value of the emission luminance (cd/m²) need to be 1.569E-03 (W/sr/m²) or more and 7.646E-01 (cd/m²) or more, respectively.

The invention claimed is:

1. A light-emitting device comprising a light-emitting element including an anode, a cathode, and a light-emitting layer which is provided between the anode and the cathode and emits light in a near-infrared region by applying a current between the anode and the cathode, wherein
the light-emitting device emits visible light with a luminance of 5 cd/m² or more when a current is applied between the anode and the cathode at a current density of 300 mA/cm² or less,
the light-emitting layer is constituted by including a light-emitting material and a host material which holds the light-emitting material, and
wherein the light-emitting material contains at least one of a compound represented by the following general formula (IRD-1), a compound represented by the following general formula (IRD-2), a compound represented by the following general formula (IRD-3), and a compound represented by the following general formula (IRD-4):

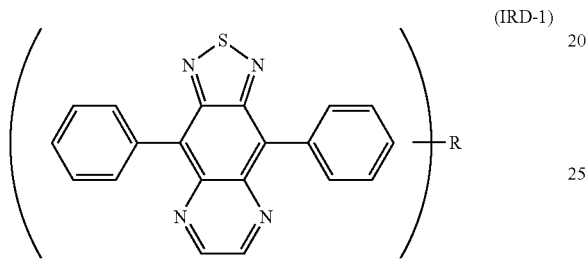
(IRD-1)

wherein each R independently represents an aryl group, an arylamino group, triarylamine, or a group containing at least one of the derivatives thereof,

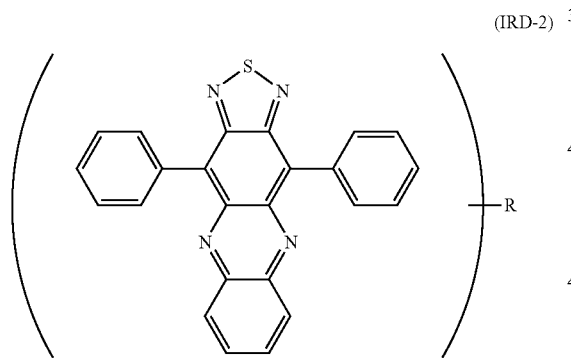
(IRD-2)

wherein each R independently represents an aryl group, an arylamino group, triarylamine, or a group containing at least one of the derivatives thereof,

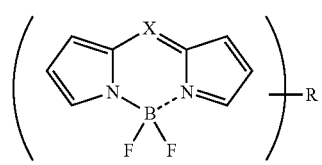
(IRD-3)

wherein X represents a carbon atom to which hydrogen is attached or a nitrogen atom, and R represents a hydrogen atom, an alkyl group, an aryl group which may have a substituent, an allyl group, an alkoxy group, or a heterocyclic group, and

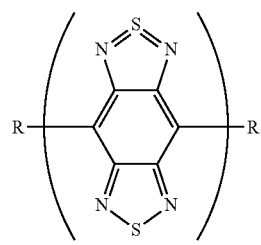
(IRD-4)

wherein each R independently represents a phenyl group, a thiophenyl group, a furyl group, or a group containing at least one of the derivatives thereof.

2. The light-emitting device according to claim 1, wherein the host material contains a compound represented by the following formula IRH-1:

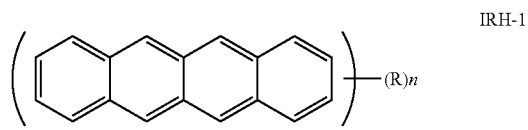
IRH-1 wherein n represents a natural number of 1 to 12, and R each independently represents a hydrogen atom, an alkyl group, an aryl group which may have a substituent, or an arylamino group.

3. The light-emitting device according to claim 1, wherein the content of the light-emitting material in the light-emitting layer is 4.0 wt % or less.

4. The light-emitting device according to claim 1, wherein the light-emitting element includes an electron transport layer which is provided between the light-emitting layer and the cathode.

5. The light-emitting device according to claim 4, wherein the electron transport layer is constituted by including a compound having an anthracene skeleton.

6. The light-emitting device according to claim 4, wherein the thickness of the electron transport layer is 20 nm or more and 200 nm or less.

7. The light-emitting device according to claim 1, wherein the thickness of the light-emitting layer is 5 nm or more and 100 nm or less.

8. An electronic apparatus, comprising the light-emitting device according to claim 1.

9. An inspection method, comprising performing an inspection by observing visible light with a luminance of 5 cd/m² or more emitted by applying a current between the anode and the cathode at a current density of 300 mA/cm² or less in the light-emitting device according to claim 1.

10. The light-emitting device according to claim 1, wherein the host material contains a compound represented by the following formula IRH-1:

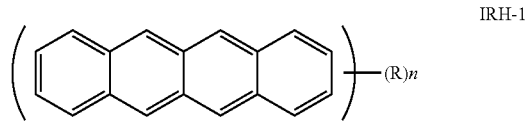
IRH-1 wherein n represents a natural number of 1 to 12, and R each independently represents a hydrogen atom, an alkyl group, an aryl group which may have a substituent, or an arylamino group.

11. The light-emitting device according to claim 10, wherein the content of the light-emitting material in the light-emitting layer is 4.0 wt % or less.

12. The light-emitting device according to claim 2, wherein the content of the light-emitting material in the light-emitting layer is 4.0 wt % or less.

13. The light-emitting device according to claim 5, wherein the thickness of the electron transport layer is 20 nm or more and 200 nm or less.

* * * * *